United States Patent
Chester et al.

(10) Patent No.: US 9,050,321 B2
(45) Date of Patent: Jun. 9, 2015

(54) RATIONALLY-DESIGNED ANTI-αβv6 INTEGRIN ANTIBODY MFEVP1 AND VARIANTS THEREOF, METHOD OF MAKING SUCH ANTIBODY AND THE USE THEREOF IN TREATING AND DIAGNOSIS OF DISEASE

(75) Inventors: Kerry Chester, London (GB); Heide Kogelberg, London (GB); John F. Marshall, London (GB)

(73) Assignee: Cancer Research Technology Limited, London (GB)

( * ) Notice: Subject to any disclaimer, the term of this patent is extended or adjusted under 35 U.S.C. 154(b) by 745 days.

(21) Appl. No.: 12/680,320

(22) PCT Filed: Sep. 26, 2008

(86) PCT No.: PCT/GB2008/003283
§ 371 (c)(1),
(2), (4) Date: Aug. 26, 2010

(87) PCT Pub. No.: WO2009/040550
PCT Pub. Date: Apr. 2, 2009

(65) Prior Publication Data
US 2011/0053254 A1     Mar. 3, 2011

(30) Foreign Application Priority Data

Sep. 26, 2007 (GB) .................................. 0718843.6

(51) Int. Cl.
| | | |
|---|---|---|
| *A61K 39/395* | (2006.01) | |
| *C07K 16/30* | (2006.01) | |
| *C07K 16/28* | (2006.01) | |
| *C07K 16/46* | (2006.01) | |
| *C12N 15/63* | (2006.01) | |
| *C12N 5/10* | (2006.01) | |

(52) U.S. Cl.
CPC ..... *A61K 39/39558* (2013.01); *A61K 39/39541* (2013.01); *C07K 16/2839* (2013.01); *C07K 16/3007* (2013.01); *C07K 2317/31* (2013.01); *C07K 2317/622* (2013.01); *C07K 2317/77* (2013.01); *C07K 2318/10* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,876,691 A * | 3/1999 | Chester et al. ............... | 424/1.49 |
| 6,774,225 B2 | 8/2004 | Yong | |
| 7,232,888 B2 | 6/2007 | Begent et al. | |
| 7,626,011 B2 | 12/2009 | Begent et al. | |
| 2005/0147614 A1 | 7/2005 | Begent et al. | |

FOREIGN PATENT DOCUMENTS

| | | |
|---|---|---|
| EP | 0120694 A2 | 3/1984 |
| EP | 0125023 A1 | 4/1984 |
| EP | 0184187 A2 | 12/1985 |
| EP | 0239400 A2 | 3/1987 |
| EP | 2188638 A | 3/1987 |
| EP | 0239400 A2 | 9/1987 |
| EP | 0733072 B1 | 4/2000 |
| WO | 9311161 | 6/1993 |
| WO | 9413804 | 6/1994 |
| WO | 9500534 | 1/1995 |
| WO | 9515341 | 6/1995 |
| WO | 9606641 | 3/1996 |
| WO | 0232404 A2 | 4/2002 |
| WO | 2005010816 A2 | 2/2005 |
| WO | 2005116226 A2 | 12/2005 |
| WO | 2007008712 A2 | 1/2007 |
| WO | 2007039728 A2 | 4/2007 |

OTHER PUBLICATIONS

Rudikoff et al., Single amino acid substitution altering antigen-binding specificity, 1982, Proceedings of the National Academy of Sciences, USA, vol. 79, p. 1979-1983.*
Panka et al., Variable region framework differences result in decreased or increased affinity of variant anti-digoxin antibodies, 1988, Proceedings of the National Academy of Sciences, USA, vol. 85, p. 3080-3084.*
Cook et al., Recombinant antibodies containing an engineered B-cell epitope capable of eliciting conformation-specific antibody responses, 1995, Vaccine, vol. 13, No. 18, p. 1770-1778.*
Wall et al., Transgenic livestock: Progress and prospects for the future, 1996, Theriogenology, vol. 45, p. 57-68.*
Houdebine et al., Production of pharmaceutical protein from transgenic animals, 1994, Journal of Biotechnology, vol. 34, p. 269-287.*
Kappell et al., Regulating gene expression in transgenic animals, 1992, Current Opinion in Biotechnology, vol. 3, p. 548-553.*
Paul, Fundamental Immunology: Third Edition, 1993.*
Bendig, Humaniziation of rodent monoclonal antibodies by CDR grafting, 1995, Methods: A companion to methods in enzymology, vol. 8, p. 83-93.*
MacCallum et al., Antibody-antigen interactions: Contact analysis and binding site topography, 1996, Journal of Molecular Biology, vol. 262, p. 732-745.*
Casset et al., A peptide mimetic of an anti-CD4 monoclonal antibody by rational design, 2003, Biochemical and Biophysical Research Communications, vol. 307, p. 198-205.*

(Continued)

*Primary Examiner* — Hong Sang
*Assistant Examiner* — Michael D Allen
(74) *Attorney, Agent, or Firm* — Patrick J. Hagan; Dann, Dorfman, Herrell and Skillman

(57) ABSTRACT

The present invention relates to antibodies that are obtained by inserting an amino acid sequence capable of binding to a target into the complementarity determining region (CDR) of a parent antibody. The antibody thus obtained has a new binding specificity. For example, the antibodies of the present invention are able to bind to the target, such as αvβ6 integrin, while retaining one or more of the useful properties of the parent antibody.

16 Claims, 18 Drawing Sheets
(3 of 18 Drawing Sheet(s) Filed in Color)

(56) References Cited

OTHER PUBLICATIONS

Johnson et al., The Kabat database and a bioinformatics example, 2004, Methods in Molecular Biology: Antibody Engineering: Methods and Protocols, vol. 248, p. 11-25.*
Baxevanis, Expert Opinion: Drug Discovery, vol. 3, No. 4, p. 441-452, 2008.*
Burgess et al., J of Cell Bio. 111:2129-2138, 1990.*
Lazar et al. Molecular and Cellular Biology 8:1247-1252, 1988.*
Ju, Proceedings of the National Academy of Sciences, U.S.A., vol. 88, p. 2658-2662, 1991.*
Baker, Immunity, vol. 13, p. 475-484, 2000.*
Huang, The Journal of Biological Chemistry, vol. 272, No. 43, p. 27155-27159, 1997.*
Dillon, Thorax, vol. 63, No. 3, p. 258, 2008.*
Lo, American Journal of Transplantation, vol. 13, Issue 12, p. 3085-3093, 2013.*
Morris, Nature, vol. 422, p. 169-173, 2003.*
Konig, J. Invest. Dermatol., vol. 99, No. 6, p. 808-812, 1992.*
Ryynanen, Biochemical and Biophysical Research Communications, vol. 180, Issue 2, p. 673-680, 1991.*
Chester, Kerry et al., "Engineering Antibodies for Clinical Applications in Cancer", Tumor Biol., 25: 91-98 (2004).
Kogelberg, Heide et al., "Engineering a Single-Chain Fv Antibody to αvBeta6 Integrin Using the Specificity-Determining Loop of a Foot-and-Mouth Disease Virus", J. Mol. Biol., 382: 385-401 (2008).
Kraft, Sabine et al., "Definition of an Unexpected Ligand Recognition Motif for αvBeta6 Integrin", J. Biol. Chem., 274 (4): 1979-1985 (1999).
Lanza, Paola et al., "Selective Interaction of a Conformationally-constrained Arg-Gly-Asp (RGD) Motif with the Integrin Receptor αvBeta3 Expressed on Human Tumor Cells", Blood Cells, Molecules and Diseases, 23(12): 230-241 (1997).
Lanza, Paola et al., "Active immunity against the CD4 receptor by using an antibody antigenized with residues 41-55 of the first extracellular domain", Proc. Natl. Acad. Sci. USA, 90: 11683-11687 (1993).
N. Ahmed et al., "Overexpression of αvβ6 integrin in serous epithelial ovarian cancer regulates extracellular matrix degradation via the plasminogen activation cascade", Carcinogenesis, 23(2): 237-244 (2002).
R.H.J. Begent et al., "Clinical evidence of efficient tumor targeting based on single-chain Fv antibody selected from a combinatorial library", Nature Medicine, 2(9): 979-984 (1996).
Mark K. Boehm et al., "Crystal structure of the anti-(carcinoembryonic antigen) single-chain Fv antibody MFE-23 and a model for antigen binding based on intermolecular contacts", Biochem. J., 346: 519-528 (2000).
Mark K. Boehm et al., "Structural models for carcinoembryonic antigen and its complex with the single-chain Fv antibody molecule MFE23", FEBS Letters, 475: 11-16 (2000).
J.M. Breuss et al., "Expression of the β6 integrin subunit in development, neoplasia and tissue repair suggests a role in epithelial remodeling", Journal of Cell Science, 108: 2241-2251 (1995).
Marcel Bruchez Jr. et al., "Semiconductor Nanocrystals as Fluorescent Biological Labels", Science, 281: 2013-2016 (1998).
Alison Burman et al., "Specificity of the VP1 GH Loop of Foot-and-Mouth Disease Virus for αv Integrins", Journal of Virology, 80(19): 9798-9810 (2006).
K.A. Chester et al., "Clinical applications of phage-derived sFvs and sFv fusion proteins", Disease Markers, 16: 53-62 (2000).
Kerry A. Chester et al., "Phage libraries for generation of clinically useful antibodies", Lancet, 343: 455-56 (1994).
Simon Chowdhury et al., "Efficient Retroviral Vector Targeting of Carcinoembryonic Antigen-Positive Tumors", Molecular Therapy, 9(1): 85-92 (2004).
Stephen P. Cooke et al., "In Vivo Tumor Delivery of a Recombinant Single-Chain Fv::Tumor Necrosis Factor: A Fusion Protein", Bioconjugate Chem., 13: 7-15 (2002).
Danielle Dicara et al., Structure-Function Analysis of Arg-Gly-Asp Helix Motifs in αvβ6 Integrin Ligands, J. Biol. Chem., 282(13): 9657-9665 (2007).
Filippo G. Giancotti et al., "Integrin-mediated adhesion and signaling in tumorigenesis", Biochimica et Biophysica Acta, 1198: 47-64 (1994).
Christilyn P. Graff et al., "Directed evolution of an anti-carcinoembryonic antigen scFv with a 4-day monovalent dissociation half-time at 37oC", Protein Engineering, Design & Selection, 17(4): 293-304 (2004).
Philipp Holliger et al., "Engineered antibody fragments and the rise of single domains", Nature Biotechnology, 23 (9): 1126-1136 (2005).
Philipp Holliger et al., "'Diabodies': Small bivalent and bispecific antibody fragments", Proc. Natl. Acad. Sci. USA, 90: 6444-6448 (1993).
Shi-Zhen Hu et al., "Minibody: A Novel Engineeered Anti-Carcinoembryonic Antigen Antibody Fragment (Single-Chain Fv-CH3) Which Exhibits Rapid, High-Level Targeting of Xenografts", Can. Res., 56: 3055-3061 (1996).
Martin J. Humphries, "The molecular basis and specificity of integrin-ligand interactions", Journal of Cell Science, 97: 585-592 (1990).
James S. Huston et al., "Protein engineering of antibody binding sites: Recovery of specific activity in an anti-digoxin single-chain Fv analogue produced in *Escherichia coli*", Proc. Natl. Acad. Sci. USA, 85: 5879-5883 (1988).
Richard O. Hynes et al., "Integrins: Bidirectional, Allosteric Signaling Machines", Cell, 110: 673-687 (2002).
Terry Jackson et al., "Structure and receptor binding", Virus Research, 91: 33-46 (2003).
Sabine Kraft et al., "Definition of an Unexpected Ligand Recognition Motif for αvβ6 Integrin", J. Biol. Chem., 274(4): 1979-1985 (1999).
Paola Lanza et al., "Selective Interaction of a Conformationally-constrained Arg-Gly-Asp (RGD) Motif with the Integrin Receptor αvβ3 Expressed on Human Tumor Cells", Blood Cells, Molecules, and Diseases, 23(12): 230-241 (1997).
Paola Lanza et al., "Active immunity against the CD4 receptor by using an antibody antigenized with residues 41-55 of the first extracellular domain", Proc. Natl. Acad. Sci. USA, 90: 11683-11687 (1993).
Derek Logan et al., "Structure of a major immunogenic site on foot-and-mouth disease virus", Nature, 362: 566-568 (1993).
Maurico G. Mateu et al., "Systematic Replacement of Amino Acid Residues within an Arg-Gly-Asp-containing Loop of Foot-and-Mouth Disease Virus and Effect on Cell Recognition", The Journal of Biological Chemistry, 271(22): 12814-12819 (1996).
Astrid Mayer et al., "Radioimmunoguided Surgery in Colorectal Cancer Using a Genetically Engineered Anti-CEA Single-Chain Fv Antibody", Clinical Cancer Research, 6: 1711-1719 (2000).
Kathryn E. McLane et al., "Transplantation of a 17-amino acid α-helical DNA-binding domain into an antibody molecule confers sequence-dependent DNA recognition", Proc. Natl. Acad. Sci. USA, 92: 5214-5218 (1995).
Gianluca Moroncini et al., "Motif-grafted antibodies containing the replicative interface of cellular PrP are specific for PrP Sc", PNAS, 101(28): 10404-10409 (2004).
John S. Munger et al., "The Integrin αvβ6 Binds and Activates Latent TGFβ1: A Mechanism for Regulating Pulmonary Inflammation and Fibrosis", Cell, 96: 319-328 (1999).
CRJ Pameijer et al., "Conversion of a tumor-binding peptide identified by phage display to a functional chimeric T cell antigen receptor", Cancer Gene Therapy, 14: 91-97 (2007).
Elena N. Peletskaya et al., "Characterization of Peptides that Bind the Tumor-Associated Thomsen-Friedenreich Antigen Selected from Bacteriophage Display Libraries", J. Mol. Biol., 270: 374-384 (1997).
Daniel M. Ramos et al., "Expression of integrin β6 enhanced invasive behavior in oral squamous cell carcinoma", Matrix Biology, 21: 297-307 (2002).
Sophia Ran et al., "Infarction of Solid Hodgkin's Tumors in Mice by Antibody-directed Targeting of Tissue Factor to Tumor Vasculature", Can. Res., 58: 4646-4653 (1998).

(56) References Cited

OTHER PUBLICATIONS

D.A. Read et al., "Mutagenesis of Single-Chain Antibody MFE 23 and its Effect on Affinity for CEA", Br. J. Cancer, 71 (57): 132 (1995).
Yoram Reiter et al., "Engineering antibody Fv fragments for cancer detection and therapy: Disulfide-stabilized Fv fragments", Nature Biotechnology, 14: 1239-1245 (1996).
Erkki Ruoslahti et al., "Integrins", J. Clin. Invest., 87: 1-5 (1991).
Surinder K. Sharma et al., "Sustained Tumor Regression of Human Colorectal Cancer Xenografts Using a Multifunctional Mannosylated Fusion Protein in Antibody-Directed Enzyme Prodrug Therapy", Clin. Can. Rev., 11: 814-825 (2005).
AJ Sheen et al., "T lymphocytes isolated from patients with advanced colorectal cancer are suitable for gene immunotherapy approaches", British Journal of Cancer, 88: 1119-1127 (2003).
Peter J. Simon et al., "Display of somatostatin-related peptides in the complementarity determining regikons of an antibody light chain", Archives of Biochemistry and Biophysics, 440: 148-157 (2005).
B. Sipos et al., "Immunohistochemical screening for $\beta6$-integrin subunit expression in adenocarcinomas using a novel monoclonal antibody reveals strong up-regulation in pancreatic ductal adenocarcinomas in vivo and in vitro", Histopathology, 45; 226-236 (2004).
Gareth J. Thomas et al., "Expression of the $\alpha v\beta 6$ Integrin Promotes Migration and Invasion in Squamous Carcinoma Cells", The Journal for Investigative Dermatology, Inc., 117(1): 67-73 (2001).
G. J. Thomas et al., "$\alpha v\beta 6$ integrin in wound healing and cancer of the oral cavity", J. Oral Pathol. Med., 35: 1-10 (2006).
Berend Tolner et al., "Production of recombinant protein in *Pichia pastoris* by fermentation", Nature Protcols, 1(2): 1006-1021 (2006).

\* cited by examiner

β6, Control

RATIONALLY-DESIGNED ANTI-αβv6 INTEGRIN ANTIBODY MFEVP1 AND VARIANTS THEREOF, METHOD OF MAKING SUCH ANTIBODY AND THE USE THEREOF IN TREATING AND DIAGNOSIS OF DISEASE

FIELD OF THE INVENTION

The present invention relates to materials and methods for modifying the binding of antibodies, and more particularly to antibodies that are obtainable by inserting an amino acid sequence capable of binding to a target into a complementarity determining region of a parent antibody so that the antibody thus obtained is capable of binding to the target. The present invention further relates to the uses of the antibodies for therapy, diagnosis or imaging and to methods of producing the antibodies.

BACKGROUND OF THE INVENTION

Integrins are a family of heterodimeric class I transmembrane receptors. Individual integrins comprise an α and β subunit in non covalent association and there are known to exist at least 18 α subunits and 8 β subunits that can form 24 different heterodimers. They are involved in numerous cell-matrix and cell-cell interactions and facilitate cell adhesion, proliferation, migration and invasion. These processes occur in several normal and pathological processes, including wound healing, inflammation and tumour growth and metastasis.

αvβ6 is an epithelial cell-restricted integrin and has been shown to be expressed in malignant but not in normal epithelium. De novo expression of this integrin has been reported in oral squamous cell carcinomas (SCC) and ovarian cancer tissues and cancer cell lines. Over-expression has been reported in adenocarcinomas of the breast, and ovarian cancer, colon carcinoma, oral squamous cell carcinoma and in gastroenteropancreatic adenocarcinomas, in particular in pancreatic ductal adenocarcinomas. It has also been shown that expression of β6 in a poorly invasive SCC cell line increased migration on fibronectin and invasion through the reconstituted basement membrane, suggesting a primary role for this integrin in oral SCC invasion and metastasis. The transcriptional activation of β6 and subsequent expression of αvβ6 has been observed during the epithelial-mesenchymal transition (EMT), which allows colon carcinoma cells to acquire a more aggressive phenotype. Moreover, analysis of colorectal carcinoma samples revealed that the elevated expression is associated with a significantly reduced survival time of patients.

WO2007/039728 (Cancer Research Technology Limited) discloses experiments in which αvβ6 peptide ligands comprising the sequence motif RGDLXXL/I, wherein LXXL/I is contained within an alpha helical structure are investigated. The use of this peptide motif arose from studies in which αvβ6 expression was involved in activation of autocrine TGF-β in post-EMT cells. The Latency Associated Protein (LAP) of the LAP-TGFβ1 complex is a known ligand for αvβ6 and binding has a role in the activation of TGF-β1. The LAP protein contains the arginine-glycine-aspartic acid (RGD) sequence, a known binding motif for most integrins. In addition, a further ligand for αvβ6 is the viral protein 1 (VP1) of the foot-and-mouth disease virus (FMDV), which also contains the RGD motif. FMDV uses αvβ6 to attach to host cells and the integrin most likely also plays a role in virus uptake into endosomes. The binding of VP1 specifically to αvβ6 is mediated via residues immediately following and including the aspartic acid of the RGD motif; the DLXXL sequence has been identified as an additional αvβ6 binding motif from its ability to inhibit αvβ6-fibronectin interactions. Peptides in which either of the two leucine residues were mutated were less good as inhibitors of FMDV C-S8c1 to recognize and infect susceptible cells. The highly related RGDLXXI motif is present in the LAP protein and would be predicted to be also involved in binding with high affinity to αvβ6.

A previous study engineered a RGD motif and three RGD repeats into the CRD3 loop of an immunoglobulin human/mouse chimeric heavy chain antibody and showed that the antibody recognized specifically the integrin αvβ6(20). Similarly, a gp120 binding antibody was increased by inserting a peptide from the CD4 receptor into the CRD3 loop (21) and a DNA-binding antibody by replacing the CDR3 loop with a sequence from a class B basic helix-loop-helix protein (22). More recently peptide sequences of the prion protein that are known epitopes for monoclonal antibodies that inhibit prion disease formation were grafted into the CDR3 loop of the heavy chain of an IgG antibody specific for the envelope glycoprotein of HIV-1 (23). The resulting Prp-IgGs bound specifically to disease-associated conformations of PrP but not to the HIV envelope.

SUMMARY OF THE INVENTION

Broadly, the present invention concerns antibodies that are obtainable by inserting an amino acid sequence that is capable of binding to a target into the complementarity determining region (CDR) of a parent antibody so that the antibody thus obtained is capable of binding to the target. Thus, this approach may be used to introduce a new binding specificity to the antibody. As the insertion is made in one of the CDRs of the parent antibody, and is preferably made in CDR H3, the insertion often has the effect of reducing or abolishing the binding of the parent antibody for the antigen to which it initially bound. The antibodies of the present invention are useful as they are able to bind to the target, such as αvβ6 integrin, while retaining one or more of the useful properties of the parent antibody, such as interacting with the immune system (e.g. recruitment of complement), a pharmacological property such as stability and/or half-life, e.g. when the antibody is administered in vivo and especially when compared to the corresponding peptide, and/or ease of production in recombinant host cells. In the present invention, the parent antibodies are based on MFE-23 antibodies and variants and derivatives thereof as discussed in more detail below.

Accordingly, in a first aspect, the present invention provides an antibody which is capable of binding to a target as obtainable by inserting an amino acid sequence capable of binding to the target into a complementarity determining region of a parent antibody, wherein the parent antibody comprises the following complementary determining regions (CDRs):

```
(a) Heavy Chain CDR 1:
                                  (SEQ ID NO: 20)
    Gly Phe Asn Ile Lys Asp Ser;
    and/or (b) Heavy Chain CDR 2:
                                  (SEQ ID NO: 21)
    Asp Pro Glu Asn Gly Asp;
    and/or
```

-continued (c) Heavy Chain CDR 3:
(SEQ ID NO: 22)
Thr Pro Thr Gly Pro Tyr Tyr Phe Asp;
and/or (d) Light Chain CDR 1:
(SEQ ID NO: 23)
(i) Ser Ser Ser Val Pro,
or (SEQ ID NO: 24)
(ii) Ser Ser Ser Val Ser;
and/or (e) Light Chain CDR 2:
(i) Ser Thr Ser,
or (ii) Leu Thr Ser;
and/or (f) Light Chain CDR 3:
(SEQ ID NO: 25)
Arg Ser Ser Tyr Pro Leu.

The CDRs identified immediately above have the following sequences, according to the standard Kabat numbering system:

(a) Heavy Chain CDR 1: Asp Ser Tyr Met His(SEQ ID NO: 53); and (b) Heavy Chain CDR 2: Trp Ile Asp Pro Glu Asn Gly Asp Thr Glu Tyr Ala Pro Lys Phe Gln Gly(SEQ ID NO; 54); and (c) Heavy Chain CDR 3: (i) Gly Thr Pro Thr Gly Pro Tyr Tyr Phe Asp Tyr (SEQ ID NO: 55), or (ii) Gly Thr Pro Thr Gly Pro Tyr Pro Phe Asp Tyr (SEQ ID NO: 56); and (d) Light Chain CDR 1: (i) Ser Ala Ser Ser Ser Val Pro Tyr Met His (SEQ ID NO: 57), or (ii) Ser Ala Ser Ser Ser Val Ser Tyr Met His (SEQ ID NO: 58); and (e) Light Chain CDR 2: (i) Ser Thr Ser Asn Leu Ala Ser (SEQ ID NO: 59), or (ii) Leu Thr Ser Asn Leu Ala Ser (SEQ ID NO: 60); and (f) Light Chain CDR 3: Gln Gln Arg Ser Ser Tyr Pro Leu Thr (SEQ ID NO: 61).

In some embodiments, the antibody may have an amino acid sequence capable of binding to the target inserted into more than one of the complementarity determining regions of the parent antibody. Additionally or alternatively, the antibody may have an amino acid sequence capable of binding to the target grafted onto a complementarity determining region of the parent antibody.

As discussed further herein, the above CDRs are derived from MFE-23 antibodies and amino acid sequence for binding to the target is preferably inserted into the heavy chain CDR3 of the parent antibody, and more preferably between amino acids Thr and Gly residues of CDR H3 of the parent antibody, i.e. between residues 98 and 99 as shown in the sequence of MFE-23 provided herein.

In another preferred embodiment, the target is inserted into the heavy chain CDR2 of the parent antibody, preferably between amino acids Glu and Asn of CDR H2 of the parent antibody, i.e. between residues 53 and 54 of the sequence of MFE-23.

In a further aspect, the present invention provides an antibody as described herein for use in therapy, diagnosis or imaging.

In a further aspect, the present invention provides the use of an antibody as described herein for the preparation of a reagent for imaging or diagnosis using a detectable group conjugated or linked to the antibody.

In a further aspect, the present invention provides the use of an antibody as described herein for the preparation of a medicament for the treatment of a condition characterised by diseased cells which express the target, for example a condition in which the cells overexpress the target and/or display the target on the cell surface and/or which is a disease mediated by the target.

Examples of such conditions are provided below and include cancer, for example by making use of the antigens expressed on the surface of cancer cells. In some embodiments, the conditions include αvβ6-mediated diseases or diseases in which cells overexpress αvβ6, such as cancer, chronic fibrosis, chronic obstructive pulmonary disease (COPD), lung emphysemia or chronic wounding skin disease.

In a further aspect, the present invention provides a method for diagnosing or imaging a condition characterised by diseased cells which express the target and/or which is a disease mediated by the target, the method comprising (a) administering to a patient suspected of having the disease an antibody as described herein which is linked to a detectable moiety and (b) detecting the detectable moiety to diagnose or image the condition.

In a further aspect, the present invention provides a method of treating a condition characterised by diseased cells which express the target and/or which is a disease mediated by the target, the method comprising administering to patient a therapeutically effective amount of an antibody as described herein.

In further aspect, the present invention provides nucleic acid sequences, expression vectors and host cells for producing antibodies according to the present invention.

Embodiments of the present invention will now be further described by way of example and not limitation with reference to the accompanying figures and tables.

BRIEF DESCRIPTION OF THE FIGURES

The application file contains at least one drawing executed in color. Copies of this application with color drawings will be provided by the Patent and Trademark Office upon request and payment of the necessary fee.

DETAILED DESCRIPTION

Antibodies

Figure 1:
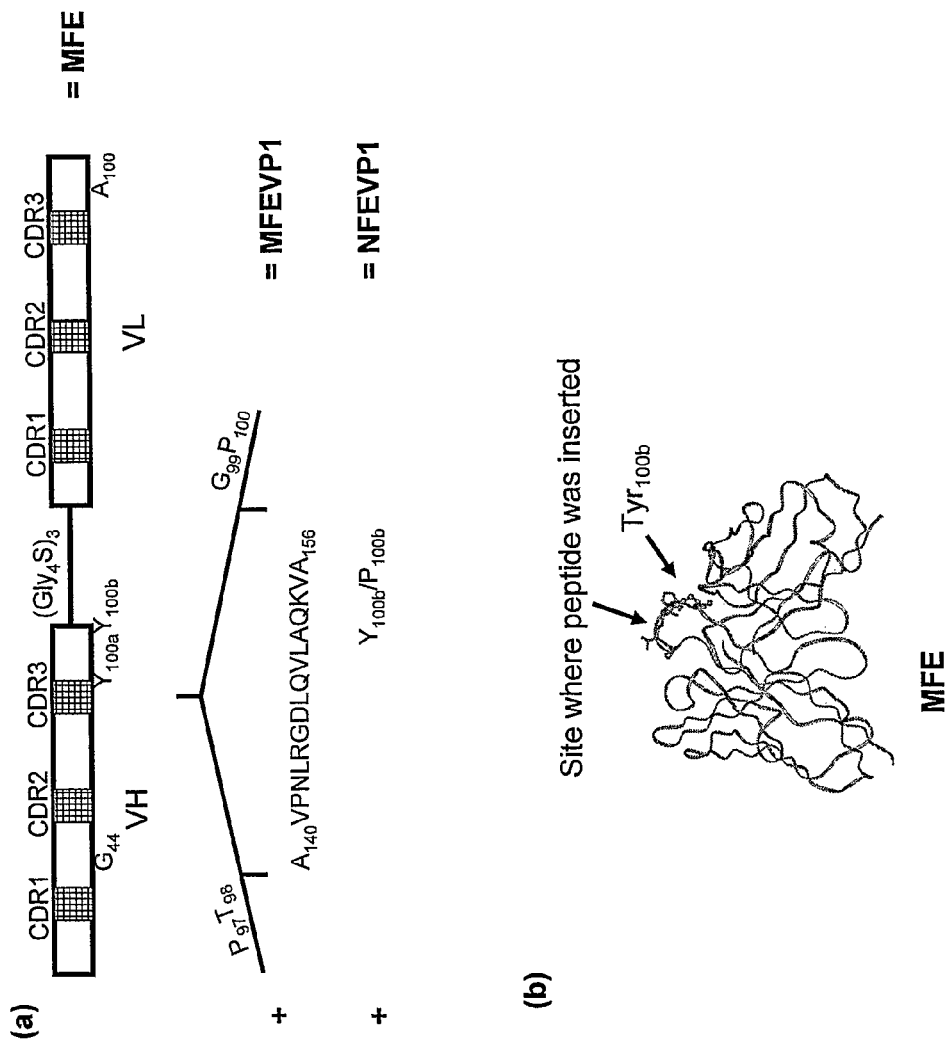
FIG. 1. Schematic presentation of the construction of MFEVP1 and NFEVP1. (A) Insertion of the RGD containing peptide sequences of VP1 ($A_{140}$ to $A_{156}$; SEQ ID NO 19) into the CDR3 loop (between T98 and G99) of the VH ch by Flow Cytometry with mouse anti-Tetra-His IgG followed by Alexa Fluor®-conjugated anti-mouse Fc. Grey solids, non-immune IgG; black lines, 10D5 (anti-αvβ6). MFEVP1 is denoted by red lines (50 μg/ml), orange lines (5 μg/ml), green lines (0.5 μg/ml) and blue lines (0.05 μg/ml). Concentrations lower than 50 μg/ml are omitted for MFE, and all A375Ppuro experiments. 50 μg/ml MFEVP1 binding to A375Pβ6 overlapped with the histograms for 5 μg/ml and 0.5 μg/ml and is not shown. Data is representative of three independent experiments with similar results. (c,d) VB6 cells were allowed to invade through LAP-coated polycarbonate filters in the presence of the proteins. Inhibition of cell migration was observed for MFEVP1, NFEVP1 (both at 50 μg/ml) and 10D5 (c) and in a concentration-dependent manner for MFEVP1 (d). W632, designated control, and 10D5 antibodies were used at 1:100 and 10 μg/ml, respectively. The data represent the mean of triplicate measurements and error bars represent the standard deviation at each data point (a,c and d).

In general, the present invention provides antibodies in which a peptide sequence capable of binding to a target, such as αvβ6 integrin, is inserted into at least one complementarity determining region of a parent antibody in order to modify the parent antibody so that it is capable of binding to the target, while retaining other useful properties of the parent antibody, such as the antibody's properties in interacting with the immune system (e.g. recruitment of complement), stability and half-life when administered in vivo, especially when compared to the corresponding peptide, and ease of production. Multiple target-binding sequences may be inserted into different complementarity determining regions of the parent antibody. Additionally or alternatively, in addition to the inserted sequence(s), a target-binding sequence may be grafted onto one or more of the complementarity determining regions of the parent antibody. The presence of multiple target binding sequences may permit the formation of dimeric or multimeric forms of the antibody. Examples of targets and the peptide sequences that are capable of binding to them are discussed in more detail below.

In particular, the present invention employs MFE-23 antibody scaffolds and variants thereof as the parent antibodies into which the targeting peptides are inserted. As used herein, MFE-23 antibodies include the following examples from this family as parent antibody scaffolds that may be used in the present invention. MFE-23 was originally a scFv isolated from a murine phage display library and selected for specific binding to carcinoembryonic antigen (CEA) (Chester et al., Lancet 343: 455-456, 1994). MFE-23 has been humanised in order to reduce the likelihood of immunogenicity (hMFE) and the humanised antibody has been affinity matured to produce the mutant scFv sm3E. A stabilised humanised form of MFE-23 is referred to as shMFE. MFE-23 antibodies, and derivatives thereof, are disclosed in WO95/15341 or EP 0733072A and U.S. Pat. No. 7,232,888, which are expressly referenced in this context for their disclosure of these antibodies, including their complete sequences including CDRs and properties. The antibodies have also undergone successful pre-clinical, and in some cases clinical, studies support its potential for use in targeted cancer therapies (e.g., radioimmunotherapy, cellular immunotherapy, gene therapy, targeted cytokine therapy) and as an imaging agent. These include Phase I studies of radiolabelled MFE-23 for use as an imaging agent, for radioimmunoguided surgery and as the tumour-targeting moiety of an antibody directed enzyme prodrug therapy.

MFE-23 antibodies comprise the following six CDRs7 as shown in SEQ ID NO: 6 of U.S. Pat. No. 7,232,888 (with the exception of CDR (d) (ii) disclosed elsewhere in the patent [and CDR (e) (i) disclosed elsewhere in the patent]):

```
(a) Heavy Chain CDR 1:
                                   (SEQ ID NO: 20)
    Gly Phe Asn Ile Lys Asp Ser;

(b) Heavy Chain CDR 2:
                                   (SEQ ID NO: 21)
    Asp Pro Glu Asn Gly Asp;

(c) Heavy Chain CDR 3:
                                   (SEQ ID NO: 22)
    Thr Pro Thr Gly Pro Tyr Tyr Phe Asp;

(d) Light Chain CDR 1:
                                   (SEQ ID NO: 23)
(i) Ser Ser Ser Val Pro,
or
                                   (SEQ ID NO: 24)
(ii) Ser Ser Ser Val Ser;

(e) Light Chain CDR 2:
(i) Ser Thr Ser,
or (ii) Leu Thr Ser;

(f) Light Chain CDR 3:
                                   (SEQ ID NO: 25)
    Arg Ser Ser Tyr Pro Leu.
```

In Light Chain CDR2, (i) is derived from the sequence of the CDR of the murine MFE-23 antibodies and (ii) is derived from the sequence of the CDR of humanised MFE-23.

Since CDR loops are the accessible regions for interaction with the epitopes of the antigen to which the parent antibody was specific, it is generally desirable in the present invention to insert the targeting peptide sequences into these regions. While any CDR of the parent MFE-23 antibodies may be suitable, it is preferred that the peptide sequence capable of binding to the target. is inserted into the CDR H3 region of the parent antibody, and preferably between residues Thr98 and Gly99. This is because the present inventors realised that in the parent MFE-23 antibodies, CDR H3 is the longest and most variable CDR and is essential for antigen binding. The site between Thr98 and Gly99 was selected as the sequence is at the end of a protruding loop structure and therefore means that the inserted targeting peptide should be available for binding to the target.

In one embodiment, the antibody of the present invention is a scFv or a diabody which comprises a linker having the sequence $(Gly_4,Ser)_n$, wherein n is between 1 and 4 (SEQ ID NOs: 26-29). A preferred example of a scFv or diabody having this general structure is represented in FIG. 1.

The insertion may also be combined with mutation of one or more amino acid residues of the CDRs or framework regions of the parent antibody to modify or otherwise improve the properties of parent antibody, for example to reduce or eliminate the binding of the parent antibody to the antigen to which it was raised or was initially capable of specifically binding or to humanise the antibody or to increase affinity for the target. However, in other embodiments, it may be useful to retain the specificity of the parent antibody so that the antibody of the present invention is bispecific. Examples of other changes made to the amino acid sequence of the parent antibody include mutation of G44 to C44 of the VH domain and A100 to C100 of the VL domain to introduce two cysteine residues to form an inter-molecular stabilising disulphide bridge in a diabody and $Y_{100b}$ to $P_{100b}$ of the VH domain to help to reduce or eliminate any remaining residual binding to CEA. Further examples of other changes to the amino acid sequence of the parent antibody include mutations to improve affinity, specificity or stability and methods for achieving this are well known in the art. For example, if affinity maturation or increased specificity is required, residues in the CDR H3 could be varied using PCR mutagenesis or site directed mutagenesis. In addition, the remaining CDRs could be varied using PCR mutagenesis, site directed mutagenesis or rational addition/replacement of peptides (Hoogenboom, (2005) and references therein). The resulting mutated genes would be cloned and expressed as scFvs in filamentous bacteriophage libraries. The libraries would be screened for phage displaying scFvs with improved binding and biological efficacy. If increased stability or yield is required the whole DNA could be varied using PCR mutagenesis, site directed mutagenesis or growth in mutator strains of bacteria (Hoogenboom, (2005) and references therein). The resulting mutated genes would be cloned and expressed as scFvs in filamentous bacteriophage libraries. The libraries would be screened for phage displaying scFvs with high expression levels and stability. In some embodiments it may also be useful to reduce the immunogenicity. Potential immunogenicity of the scFv, for example HFEVP1 or affinity matured variant, could be addressed by identification and modification of T-cell epitopes and methods for this are well known in the art. This is based on the rationale that T cell help is required in order to mount a long-lived, isotype switched and high affinity antibody response [Chester K A, at al (2005)]. The approach requires the identification of short peptides contained within the protein sequence that have a capacity to bind to the MHC class II binding groove and stimulate a subsequent T-cell response. Key residues in these peptides that contribute to T-cell epitope formation can be identified by determining whether the side chains interact with key binding pockets in the MHC class II binding groove or with the T-cell receptor (TCR). Subsequent amino acid substitutions at these key residues can inhibit T-cell epitope formation by reducing the peptide affinity for MHC class II or preventing TCR recognition of the peptide MHC complex. An experimental approach using a T-cell proliferation assays could be used as this takes into account factors that contribute to epitope formation, such as antigen processing and TCR binding. In vitro studies could be performed with peptides spanning the whole of the scFv sequence, for example, 15mer peptides overlapping by 12 amino acids. The peptides could be tested for ability to stimulate T-cells in T-cell proliferation assays. Typically, T-cells from healthy donors expressing a wide range of HLA alleles would be used in addition to T-cells obtained from any patients demonstrating an immune response to the scFv. The precise location of key residues responsible for T-cell activation could be determined by residue replacement (usually with alanine) and testing the resultant peptides in T-cell proliferation assays. In silico analysis could also be used to predict amino acid substitutions that should disrupt peptides binding to MHC class II. In the final stage, in silico modelling could be applied to predict those amino acid substitutions likely to eliminate immune reactivity to the scFv without disruption of scFv structure or loss of scFv function. The gene for the preferred variant could be manufactured by recombinant DNA technology.

In the present invention, "MFE-23 antibody" includes antibodies which comprise the CDRs of the scFv MFE-23, fragments or derivatives thereof. It also includes the CDRs when incorporated into other antibody framework as described above, e.g. to produce a complete antibody structure, a diabody or another antibody. These include antibody fragments which comprise an antigen binding domain are such as Fab, scFv, Fv, dAb, Fd and diabodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,63 A or EP 0 239 400 A.

Antibodies can be modified in a number of ways and the term "antibody" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023 A.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (WO93/11161) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

In terms of utility of these antibodies, this is primarily therapeutic with imaging/diagnosis being a secondary utility. In terms of therapeutic use, antibodies have advantages over peptides as it is generally appreciated in the art that peptides tend to have short serum half-life in vivo. In contrast, antibody therapeutics tend to possess greater stability and longer half-life. Additional advantages of preferred antibodies of the present invention include combining high affinity binding properties of the $\alpha v\beta 6$ binding peptides together with advantages of the MFE antibody scaffold, namely stability, good production yields, e.g. in *Pichia pastoris*, and for humanised versions of the MFE antibody scaffold, low predicted immunogenic potential.

Targeting Peptides

The present invention involves the insertion of amino acid sequences generally referred to herein as "targeting peptides" that are capable of binding to a target. Generally, the inserted amino acid sequences capable of binding to the target are between 8, 10 or 12 amino acids and 24 or 30 amino acids in length, and more preferably are between 12 and 20 amino acids in length. In one embodiment, the target is an antigen present on diseased cells, to which the antibodies of the present invention are capable of binding using the targeting peptide. By way of illustration, the diseased cells may be surface antigen on, for example, cancer cells. In a preferred embodiment, the targeting peptide is capable of binding to an integrin, such as $\alpha v\beta 6$ integrin which is known to be involved in normal and pathological processes such as wound healing, inflammation and tumour growth and metastasis.

More generally, the targets for the antibodies of the present invention may be targets that (i) are overexpressed or de novo expressed in diseased cells (and more specifically cancer cells) and/or (ii) are expressed in diseased cells and mediate the disease (and more specifically cancer). Thus, the present invention includes antibodies which can be used as tumour targeting antibodies, where target is overexpressed or de novo expressed in diseased cell, and/or function-modulating antibodies, e.g. whereby the target is expressed on the diseased cell and the antibody modulates the activity of the target and/or the targets ability to interact with its binding partners. In addition to $\alpha v\beta 36$ integrin, some specific examples include tumour associated antigens and/or antigens involved in mediated disease such as MUC1, 5T4, VEGFR (Hofineister V et al., 2007), Tie2, endoglin (CD105) (Hofineister V et al., 2007; Munoz R et al., 2007), uPA receptor (uPAR) (Li Y et al., 2007), PSMA (Baccala A et al., 2007, Buhler P et al., 2007) [4,5], and members of the ErbB (Her) family (Johnston J B et al., 2006).

Further targets may be identified using techniques well known in the art. These might include the following approaches.

In one approach, preferred peptides would include epitopes of the antigen-binding protein that are located on surface-exposed loops, making use of the three-dimensional structure of the antigen-binding protein. For example, in design of the MFE/shMFE/VP1 constructs we used the knowledge that the inserted 17-mer VP1 peptide is part of a long highly mobile loop that forms a self contained unit in the VP1 protein of FMDV (Logan, D., Abu-Ghazaleh, R., Blakemore, W., Curry, S., Jackson, T., King, A., Lea, S., Lewis, R., Newman, J., Parry, N., (1993) Structure of a major immunogenic site on foot-and-mouse disease virus Nature 362:566-568). It is a general feature that residues of the ligand that bind to αvβ6 are part of a surface exposed loop. In fibronectin also, which is a further ligand for αvβ6, the RGD binding motif is part of a highly mobile loop, which protrudes from the rest of the tenth type III module (Main, A. L., Harvey, T. S., Baron, M., Boyd, J., and Campbell, I. D. (1992) The three-dimensional structure of the tenth type III module of fibronectin: An insight into RGD-mediated interactions *Cell* 71:671-678).

In a second approach, preferred peptides could be rationally designed using three-dimensional structures of the ligand-antigen complex if these are available. In this case the ligand residues that are involved in binding to the cell surface antigen are known from the detail of the ligand-antigen interaction.

In a third approach, preferred peptides could be those which are potent in inhibiting antigen/antigen-binding protein interactions as shown in vitro in ELISA or cell-based assays. For example, a 17-mer peptide that contained the 17-mer VP1 peptide sequence minus the N-terminal alanine and a 20-mer peptide that contained the 17-mer peptide sequence used to create MFEVP1 were potent inhibitors of FMDV binding to purified αvβ6 and αvβ6-expressing cells (Burman, A., Clark, S., Abrescia, N. G., Fry, E. E., Stuart, D. I., and Jackson, T. (2006) Specificity of the VP1 GH Loop of Foot-and-Mouth Disease Virus for αv Integrins *J. Virol.* 80:9798-9810) and of β6-transfected fibroblast cells to LAP (Dicara, D., Rapisarda, C., Sutclifffe, J. L., Violette, S. M., Weinreb, P. H., Hart, I. R., Howard, M. J., and Marshall, J. F. (2007) Structure-function analysis of Arg-Gly-Asp helix motifs in alpha v beta 6 integrin ligands *J. Biol. Chem.* 282: 9657-9665), respectively.

In a fourth approach, preferred peptides could be those that are selected in vitro or in vivo from peptide libraries displayed on filamentous bacteriophage. This method has been used to obtain peptides with high affinity and specificity for tumour targets (Landon, L. A., Deutscher, S. L. (2003) Combinatorial Discovery of Tumor Targeting Peptides Using Phage Display. J Cell Biochem. 90:509-517). Peptide libraries consist of random cyclic and linear peptide sequences. In vitro selection is performed using purified recombinant proteins or cells that express the target protein.

For example, the 17-mer peptide VP1 peptide sequence inserted into MFE-23 to create MFEVP1 contains the DLXXL sequence, which has specificity for αvβ6, and has also been identified from screening 12-Mer peptide libraries displayed on phage using recombinant transmembrane truncated soluble receptor. (Kraft, S., Diefenbach, B., Mehta, R., Jonczyk, A., Luckenbach, G. A., and Goodman, S. L. (1999) Definition of an Unexpected Ligand Recognition Motif for αvβ6 Integrin *J. Biol. Chem.* 274:1979-1985).

In another example, a random phage library consisting of linear 12 amino acid peptides identified peptides that bound specifically to recombinant prostate-specific membrane antigen (PMSA), an attractive candidate for targeted therapy for prostate and other solid tumours (Aggarwal, S., Singh, P., Topaloglu, O., Isaacs, J. T., Denmeade, S. R. (2006) A Dimeric Peptide That Binds Selectively to Prostate-Specific Membrane Antigen and Inhibits its Enzymatic Activity *Cancer Res.* 66:9171-9177). A pIII-displayed disulphide-constrained heptamer peptide library was screened on purified extracellular PSMA to identify PSMA binding peptides.

In another example, the epidermal growth factor receptor, type 2 (ErbB-2) tyrosine kinase receptor that shows increasing promise as a target for cancer diagnosis and therapy has been used as bait. In this case, a random 6 amino acid peptide bacteriophage display library was selected against purified ErbB-2 extracellular domain to identify peptide binding sequences (Karasseva, N. G., Glinsky, V. V., Chen, N. X., Komatireddy, R., Quinn, T. P. (2002) Identification and Characterization of Peptides that Bind Human ErbB-2 Selected from a Bacteriophage Display Library *J. Protein Chem.* 21:287-296).

Peptide sequences can also be selected by display of peptide libraries on phage that bind to carbohydrate antigens, which show different composition in malignant transformations. Foe example, an in vitro phage display was employed to find peptides that bind to the Thomsen-Friedenreich (TF) tumour-associated antigen (Peletskaya, E. N., Glinsky, V. V., Glinsky, G. V., et al. (1997) Characterisation of peptides that bind the tumour-associated Thomson-Friendenreich antigen selected from bacteriophage display libraries *J. Mol. Biol.* 270:374-384).

Peptide library selection on cells was used to identify a further αvβ6 binding peptide sequence. A 20-mer peptide library fused to bacteriophage coat protein pIII selected a peptide that bound specifically to a lung adenocarcinoma cell line and was shown subseuaently to bind to αvβ6 (Elayadi, A.N., Samli, K.N., Prudkin, L., Liu, Y.-H., Bian, A., Xie, X.-J., Wistuba, I.I., Roth, J.A., McGuire, M.J., Brown, K.C. (2007). A Peptide Selected by Biopanning Identifies the Integrin αvβ6 as a Prognostic Biomarker for Nonsmall Cell Lung Cancer. *Cancer Res.* 67: 5889-5895).

Peptides that bind to tumour and tumour-associated vasculature have also been successfully selected from phage peptide libaries in vivo (Landon, L. A., Deutscher, S. L. (2003) Combinatorial Discovery of Tumor Targeting Peptides Using Phage Display. *J Cell Biochem.* 90:509-517). This approach allows for targeting of novel antigens in addition to known targets. Using as a target the RIP1-Tag2 mouse model of multistage tumorigenesis involving the pancreatic islets of Langerhans, allowed the identification of several peptides that discriminate between the vasculature of the premalignant angiogenic islets and the fully developed tumours (Joyce, J. A., Laakkonen, P., Bernasconi, M., Bergers, G., Ruoslahti, E., Hanahan, D. (2003) Stage-specific vascular markers revealed by phage display in a mouse model of pancreatic islet tumorigenesis *Cancer Cell* 4:309-403). A similar study isolated peptides selective for angiogenic progenitors and solid tumours from the skin of a transgenic mouse model involving the human papillomavirus type 16 oncogene (Hoffman, J. A., Giraudo, E., Singh, M., Zhang, L., Inoue, M., Porkka, K., Hanahan, D., Ruoslahti, E. (2003) Progressive vascular changes in a transgenic mouse model of squamous cell carcinoma *Cancer Cell* 4:383-391). Peptides specific for human vasculature and human tissue have been derived from peptide phage library selection on human tissue transplanted into SCID mice (George, A. J. T., Lee, L., Pitzalis, C. (2003) Isolating ligands specific for human vasculature using in vivo phage selection *Trends Biotech.* 21:199-203).

By way of example, the targeting peptides that may be used in accordance with the present invention include those disclosed in our earlier application, WO2007/039728. These peptides include peptides which comprise the amino acid sequence motif RGDL$X^5X^6X^7$ (SEQ ID NO: 50), wherein $X^5$, $X^6$ and $X^7$ independently represent any amino acid residue, and preferably independently selected from Glu, Ala, Leu, Met, Gln, Lys, Arg, Val, Ile, Trp, Phe, Asp, His and Thr (SEO ID NO: 51). While the peptides disclosed in WO2007/

039728 generally comprise an alpha helical structure induced by the amino acids following the RGD sequence, this is not a requirement of the peptides of the present invention, in particular as they are inserted into the CDR of a parent antibody and may not therefore be able to adopt this secondary structural feature.

Preferred examples of peptides capable of binding to •v•6 integrin include peptides which comprise amino acid sequences represented by the following general formulae, based on the peptides disclosed in WO2007/039728:

RGDLX$^5$X$^6$X$^7$ wherein
X$^5$ is selected from Glu, Ala or Gin;
X$^6$ is selected from His, Val, Thr or Glu;
X$^7$ is selected from Leu or I1e (SEQ ID NO: 52).

These peptide sequence above may be part of a longer sequences, for example having one, two, three, four, five, ten or more additional amino acids linked to the N- and/or C-terminus of the peptide, while optionally conforming to the preferred ranges of lengths of peptide sequence set out above. A particularly preferred targeting peptide sequence has the amino acid sequence AVPNLRGDLQVLAQKVA (SEQ ID NO: 19).

In some embodiments, the peptides may comprise an "alpha helical structure" as disclosed in WO2007/039728, that is a sequential group of amino acids in a peptide that interact with a particular hydrogen bonding pattern and thus define a helical structure. For example, the hydrogen bonding pattern in a standard alpha helix is between the carbonyl oxygen of residue n and the amide hydrogen of residue n+4. For the $3_{10}$-helix, this hydrogen bonding pattern is between residues n and n+3 and for a pi-helix it is between residues n and n+5. The number of residues per turn in each alpha-helix is 3.6, 3.0 and 4.4 for the standard alpha-helix, $3_{10}$-helix and pi-helix respectively, see for example WO95/00534.

Variants and Uses of the Antibodies

In one aspect, the antibodies of the present invention may be linked to a detectable moiety. The term "detectable moiety" relates to a group that, when located at the target site following administration of the antibodies of the present to a patient, may be detected, typically non-invasively from outside the body and the site of the target located. Thus, the antibodies of the present invention are useful in imaging and diagnosis. Detectable moiety are entities that are detectable by imaging techniques such as Magnetic Resonance Imaging (MRI), Magnetic Resonance Spectroscopy (MRS), Single Photon Emission Computed Tomography (SPECT) and Positron Emission Tomography (PET) and optical imaging. Preferably, imaging moieties are stable, non-toxic entities that retain their properties under in vitro and in vivo conditions. Examples of such moieties include but are not limited to radioactive moieties, for example radioactive isotopes. Suitable radioactive atoms include technetium-99m or iodine-123 for scintigraphic studies. Other readily detectable moieties include, for example, spin labels for MRI such as iodine-123 again, iodine-131, indium-111, fluorine-18, carbon-13, nitrogen-15, oxygen-17, gadolinium, manganese or iron and optical moieties which include Cy5.5 and quantum dots.

Alternatively or additionally, the antibodies of the present invention may be conjugated or linked to a therapeutically active moiety, for example a moiety that is cytotoxic.

A further class of groups that can be incorporated into the antibodies of the present invention are affinity tags that can be introduced into the antibodies to enable them to be manipulated or detected in one or more subsequent steps. A wide range of affinity tags are known in the art suitable affinity tags include members of specific binding pairs, antibodies and antigens, biotin which binds to streptavidin and avidin, poly-histidine (e.g. hexa-His or tri-His tags) or amino di- or tri-carboxylates which bind to metal ions such as Ni$^{2+}$ or Co$^{2+}$, Flag or Glu epitopes which bind to anti-Flag antibodies, S-tags which bind to streptavidin, calmodulin binding peptide which binds to calmodulin in the presence of Ca$^{2+}$; ribonuclease S which binds to aporibonuclease S; and c-Myc which recognises anti-c-Myc antibody. Examples of other affinity tags that can be used in accordance with the present invention will be apparent to those skilled in the art. Antibodies including these affinity tags can be easily purified and manipulated.

The term "therapeutically active moiety" encompasses a moiety having beneficial, prophylactic and/or therapeutic properties.

In one embodiment the therapeutically active moiety is a cytotoxic chemotherapeutic agent. Cytotoxic chemotherapeutic agents are well known in the art and include anti-cancer agents such as:

Alkylating agents including nitrogen mustards such as mechlorethamine (HN2), cyclophosphamide, ifosfamide, melphalan (L-sarcolysin) and chlorambucil; 10 ethylenimines and methylmelamines such as hexamethylmelamine, thiotepa; alkyl sulphonates such as busulfan; nitrosoureas such as carmustine (BCNU), lomustine (CCNLJ), semustine (methyl-CCN-U) and streptozoein (streptozotocin); and triazenes such as decarbazine (DTIC; dimethyltriazenoimidazolecarboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorabicin (daunomycin; rubidomycin), doxorubicin, bleomycin, plicamycin (mithramycin) and mitomycin (mitomycin Q; enzymes such as L-asparaginase; and biological response modifiers such as interferon alphe-nomes. Miscellaneous agents including platinum coordination complexes such as cisplatin (cis-DDP) and carboplatin; anthracenedione such as mitoxantrone and antbracycline; substituted urea such as hydroxyurea; methyl hydrazine derivative such as procarbazine (N-methylhydrazine, MIH); and adrenocortical suppressant such as mitotane (o, p'-DDD) and aminoglutethimide; taxol and analogues/derivatives; and hormone agonists/antagonists such as flutamide and tamoxifen.

Methods of conjugating antibodies to therapeutic agents are well known in the art.

In further embodiments, the antibodies of the present invention may be formulated using particle based delivery systems such as nanoparticles and lipid-based vesicles such as liposomes or other similar structures composed of lipids. Liposomes are a spherical vesicles comprising a phospholipid bilayer that may be used as agents to deliver materials such as drugs or genetic material. Liposomes can be composed of naturally-derived phospholipids with mixed lipid chains (egg phosphatidylethanolamine) or of pure components like DOPE (dioleolylphosphatidylethanolamine). The synthesis and use of liposomes is now well established in the art. Liposomes are generally created by sonication of phospholipids in a suitable medium such as water. Low shear rates create multilamellar liposomes having multi-layered structures. Continued high-shear sonication tends to form smaller unilamellar liposomes. Research has also been able to enable liposomes to avoid detection by the immune system, for examples by coating the liposomes with polyethylene glycol (PEG). It is also possible to incorporate species in liposomes, such as the peptides of the invention to help to target them to a delivery site, e.g. in cells or in vivo.

The use of nanoparticles as delivery agents for materials associated with or bound to the nanoparticles is known in the art. Some types of nanoparticle comprises a core, often of metal and/or semiconductor atoms, to which ligands of one or more different types may be linked, including, for example, one or more of the peptides of the present invention, see for example WO02/32404, WO2005/10816 and WO2005/116226. Other types of nanoparticle may be formed from materials such as liposomes. In some instances, the nanoparticles may be derivatised or conjugated to other ligands may be present to provide the nanoparticles with different properties or functions. In some embodiments, the nanoparticles may be quantum dots, that is nanocrystals of semiconducting materials which have the striking chemical and physical properties that differ markedly from those of the bulk solid (see Gleiter, Adv. Mater. 1992, 4, 474-481). Now that their quantum size effects are understood, fundamental and applied research on these systems has become increasingly popular. An interesting application is the use of nanocrystals as luminescent labels for biological systems, see for example Brucher et al, Science. 1998, 281, 2013-2016, Chan & Nie, Science, 1998, 281, 2016-2018, Mattousi et al, J. Am. Chem. Soc., 2000, 122, 12142-12150, and Alivisatos, Pure Appl. Chem. 2000, 72, 3-9. The quantum dots have several advantages over conventional fluorescent dyes: quantum dots emit light at a variety of precise wavelengths depending on their size and have long luminescent lifetimes.

In a further embodiment, the cytotoxic moiety is a cytotoxic peptide or polypeptide moiety by which we include any moiety which leads to cell death.

Cytotoxic peptide and polypeptide moieties are well known in the art and include, for example, ricin, abrin, *Pseudomonas* exotoxin, RNase, tissue factor and the like.

The use of ricin as a cytotoxic agent is described in Burrows & Thorpe, P.N.A.S. USA 90: 8996-9000, 1993, incorporated herein by reference, and the use of tissue factor, which leads to localised blood clotting and infarction of a tumour, has been described by Ran et al., Cancer Res. 58: 4646-4653, 1998 and Huang et al., Science 275: 25 547-550, 1997. Tsai et al., Dis. Colon Rectum 38: 1067-1074, 1995 describes the abrin A chain conjugated to a monoclonal antibody and is incorporated herein by reference.

Other ribosome inactivating proteins are described as cytotoxic agents in WO 96/06641. *Pseudomonas* exotoxin may also be used as the cytotoxic polypeptide moiety (see, for example, Aiello et al, P.N.A.S. USA 92: 10457-10461, 1995.

Certain cytokines, such as TNFα and IL-2, may also be useful as cytotoxic and/or therapeutic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the antibody of the invention are such that a dose of more than 4000 cGy, and more preferably at least 6000, 8000 or 10000 cGy, is delivered to the target site and, preferably, to the cells at the target site and their organelles, particularly the nucleus.

The radioactive atom may be attached to the binding moiety in known ways. For example, EDTA or another chelating agent may be attached to the binding moiety and used to attach $^{111}$In or $^{90}$Y. Tyrosine residues may be labelled with $^{125}$I or $^{131}$I.

In a further embodiment, the present invention provides a polypeptide is linked to viral coat protein other than FMDV to change the trophism of the virus for delivery of DNA encoding therapeutic genes.

Alternatively, any of these systems can be incorporated into a prodrug system. Such prodrug systems are well known in the art and include ADEPT systems in which an antibody according to the present invention is conjugated or conjugatable or fused to an agent capable of converting a prodrug to a cytotoxic moiety is an enzyme for use in antibody directed enzyme prodrug therapy.

In a further aspect, the present invention provides a pharmaceutical composition comprising peptide and/or nucleic acid and/or expression vector as defined above and a pharmaceutical acceptable carrier.

The term "pharmaceutically acceptable carrier" generally includes components, that are compatible with the peptide, nucleic acid or vector and are not deleterious to the recipients thereof. Typically, the carriers will be water or saline which will be sterile and pyrogen free. However, other acceptable carriers may be used. Typically, the pharmaceutical compositions or formulations of the invention are for parenteral administration, more particularly for intravenous administration.

In a further aspect, the present invention provides the use of an antibody as described herein, or nucleic acid encoding the antibody or a vector comprising the nucleic acid, for the preparation of a medicament for the treatment of a condition characterised by diseased cells which express the target, for example a condition in which the cells overexpress the target and/or display the target on the cell surface and/or which is disease that is mediated by the target.

Examples of such conditions are provided below and include cancer, for example by making use of the antigens expressed on the surface of cancer cells. In some embodiments, the conditions include αvβ6-mediated diseases or diseases in which cells overexpress αvβ6, such as cancer, chronic fibrosis, chronic obstructive pulmonary disease (COPD), lung emphysemia or chronic wounding skin disease, such as epidermolysis bullosa. As mentioned herein, these conditions also include the treatment of wound healing and inflammation.

The medicament or pharmaceutical composition of the present invention as defined above may usefully be administered to a patient who is also administered other medicaments, as it will be known to those skilled in the art. For example, in the case of cancer, the medicament or pharmaceutical composition of the present invention may be administered to a patient before, after or during administration of the other anti-tumour agent(s), for example before, after or during chemotherapy. Treatment with the antibody after chemotherapy may be particularly useful in reducing or preventing recurrence of the tumour or metastasis. For example, the anti-tumour agent can be covalently linked directly or indirectly (via liposomes/nanoparticles) to an antibody of the present invention.

In a further aspect, the present invention provides a method of imaging epithelial cells overexpressing αvβ6 in the body of an individual, the method comprising administering to the individual an effective amount of an antibody as defined herein. The method is particularly useful for the imaging of chronic fibrosis, chronic obstructive pulmonary disease (COPD), lung emphysema, chronic wounding skin disease (e.g. epidermolysis bullosa) or epithelial tumour cells. For example, the method of imaging may include linking the targeting antibody to a fluorescent probe and incorporate into a mouth-wash, chewing gum, spray or other emolument such that the antibody-probe conjugate may be visualised by its fluorescent tag.

EXAMPLES

The experimental examples set out below demonstrate that the specificity of a parent antibody can be modified by inserting a αvβ6 binding peptide sequence into the CDR of the parent antibody. In the examples, the parent antibody is a single-chain Fv antibody fragment (scFv), which consists of the variable heavy and variable light chain regions tethered by a flexible linker that retains the complete antibody's binding properties. By way of example, the scFv may be based on a MFE-23 scFv, a scFv developed by phage technology that binds with high affinity to the carcinoembryonic antigen, CEA (14). CEA is a tumour selective marker that is highly expressed on most gastrointestinal carcinomas and on a number of breast, lung and ovarian carcinomas. Iodinated MFE has been used in patients for imaging (15) and radioimmunoguided surgery in colorectal cancer (16). MFE has also shown promise for cancer therapy when used as a fusion protein with carboxypeptidase G2 in antibody-directed enzyme prodrug therapy (ADEPT) (17); (18).

In this embodiment of the present invention, a scFv against αvβ6 was produced rationally by antibody engineering by inserting the peptide binding motifs of the known αvβ6 peptide ligands, such as VP1 proteins, into the loop region of MFE. The third complementarity-determining region (CRD3) of the variable heavy chain (VH) of MFE provides the major site of interaction with CEA, as assessed by mutagenesis, and accordingly was chosen as a preferred site for such an insertion.

In the experiments set out below, the insertion of an αvβ6-binding peptide of VP1 from the FMDV strain $O_1$ BFS into the CRD3 loop of the VH domain of MFE is described. A 17-mer peptide and a 20-mer peptide corresponding to this region of VP1 have previously been shown to be potent inhibitors of FMDV binding to purified αvβ6 and αvβ6-expressing cells (24) and of β6-transfected fibroblast cells to LAP (25), respectively. The addition of a 17-mer peptide of VP1, equivalent in sequence to the inhibitory peptides, to MFE changed binding specificity of the scFv from CEA to αvβ6, as shown by ELISA, cell-binding and inhibition in a migration assay. Additional mutation of $Y_{100b}$ to $P_{100b}$ of the VH domain as in NFEVP1 eliminated all remaining residual binding to CEA.

Materials and Methods
3D Protein Visualisation

The X-ray structure of MFE (pdb code 1QOK) (26) was visualised in Insight II (Accelrys) on a Silicon Graphics workstation.

Antibodies

Murine monoclonal antibodies to αvβ3 (LM609), αvβ6 (10D5) and α5β1 (P1D6) were purchased from Chemicon International, Harrow, UK whereas those to αvβ5 (P1F6) and αvβ8(14E5) were generous gifts from Drs. Dean Sheppard and Steve Nishimura (UCSF), respectively. The secondary antibody was Alexafluor-488 conjugated rabbit anti-mouse antisera (Molecular Probes) unless otherwise stated.

Construction of Plasmids for Expression in E. coli Construction of MFE-RGD and MFE-RGE Plasmid, MFE-RGD/pUC119 and MFE-RGE/pUC119

MFE-RGD and MFE23-RGE were constructed by site-directed mutagenesis using the MFE-RGD forward (5'_CTACTGCAACGAAGGGACAGCTAGAGGTGATTT-GGCTACTTTGTTCGACTACTGGGGACAAG_3'; SEQ ID NO: 30) and MFE-RGD reverse (5'_CTTGTCCCCAG-TAGTCGAACAAAGTAGCCAAATCACCTCTAGCTGT-CCCTTCGTTGCAGTAG _3'; SEQ ID NO: 31) primers or MFE-RGE forward (5'_GAAGGGACAGCTAGAGGT-GAATTGGCTACTTTGTTCGACTACTG_3'; SEQ ID NO: 32) and MFE-RGE reverse (5'_CAGTAGTCGAACAAAG-TAGCCAATTCACCTCTAGCTGTCCCTTC _3'; SEQ ID NO: 33) respectively. The PCR reactions used the phMFE-his_119plasmid as template, which incorporated the humanised form of MFE-23 (hMFE) and a C-terminal 6xHis tag enabling purification by Immobilised Metal Ion Affinity Chromatography (IMAC).

Construction of MFE and HFE MFE VH CDR3 Loop Variant Plasmid, MFEVP1/pUC119 and HFEVP1/pUC119

MFEVP1 and HFEVP1, which contain the MFE of HFE sequences respectively, and a 17-mer αvβ6-binding peptide of VP1 in the
CRD3 loop of the heavy chain (FIG. 1), were constructed from three PCR reactions. First, the 5' end were constructed with the VH MFEVP1 (5'CATGCCATGGCCCAGGT-GAAACTG; SEQ ID NO: 34) or VH HFEVP1 (5'CATGC-CATGGCCCAAGTTAAACTGGAACAG TCC; SEQ ID NO: 35) sense primers and the MFEVP1(5'GCGCCAGCAC-CTGCAGATCACCTCGCAGATTCGGAACT-GCAGTCGGAGTCCCCTCATTA C; SEQ ID NO: 36) or HFEVP1(5'GAGCCAGCACCTGCAGATCACCTCGCA-GATTCGGAACTGCAGTTGGTGTCCCTTCGTTG C; SEQ ID NO: 37) anti-sense primers, respectively, that contained parts of the additional peptides of the αvβ6-binding motif of VP1 (shown underlined in the primes). Second, the 3' ends were constructed with the VL MFEVP1 (5' ATAGTT-TAGCGGCCGCCCGTTTCAGCTC; SEQ ID NO: 38) or VL HFEVP1 (5' ATAGTTTAGCGGCCGCAGCCTTGATTTC; SEQ ID NO: 39) anti-sense primers and the MFEVP1(5'CT-GCGAGGTGATCTGCAGGTGCTGGCGCA-GAAAGTTGCAGGGCCGTACTACTTTGACTA CTG; SEQ ID NO: 40) or HFEVP1(5'CTGCGAGGTGATCTG-CAGGTGCTGGCTCAGAAAGTTGCAGGTC-CTTACCCTTTCGACTA CTGGGGACAAGG; SEQ ID NO: 41) sense primers, respectively which contain part of the additional αvβ6-binding motif and in the case of HFEVP1 also introduced the Y100b to P100b mutation (shown bold and underlined in the primer; amino acid numbering is given with the Kabat nomenclature). The PCR reactions for MFEVP1 used the MFE/puc119 as template and those for HFEVP1the HFE/pCTCON plasmid (27) as templates. Third, the PCR products from the first two reactions, were used as templates and amplified with the VH MFEVP1 sense and VL MFEVP1 anti-sense or VH NFEVP1 sense and VL HFECP1 anti-sense primers to give the PCR product for MFEVP1 or HFEVP1 respectively. The VH sense and VL anti-sense primers introduced NcoI and NotI sites (shown in bold and underlined in the primers) into the PCR products, respectively. Thus, the third PCR products and the puCH9 plasmid were treated with these restriction enzymes and ligated to yield either MFEVP1/pUC119 or HFEVP1 plasmids. Correctness of the DNA sequences was verified by DNA sequencing.

Introduction of the VH-$Y_{100b}$ to VH-$P_{100b}$ Mutation in MFEVP1 Plasmid

The $Y_{100b}$ to $P_{100b}$ mutations of the VH domain of the MFEVP1 was introduced by site-directed mutagenesis. The Pro mutation was introduced in MFEVP1/pUC119 with 5'GTTGCAGGGCCGTACCCGTTTGACTACTGGGGC 3' (SEQ ID NO: 42) as the sense and 5'GCCCCAGTAGT-CAAACGGGTACGGCCCTGCAAC 3' (SEQ ID NO: 43) as the anti-sense primers to give NFEVP11/pUC119 (the Pro nucleotide sequence is shown in bold). DNA sequencing verified these Pro mutations.

Construction of NFEVP1/pICZαBHis and HFEVP1/pCIZαBCysHis Plasmid for, Expression in Yeast The NFEVP1/pUC119 and HFEVP1/pUC119 plasmid were digested with SfiI and NotI and cloned into an equally digested pICZαBHis or pPICZαBCysHis vectors respectively, for expression in yeast. The modified pICZαBHis and pICZαBCysHis vectors, when compared to the original pPICZαB vector (Invitrogen, Karlsruhe, Germany), do not contain the myc-tag but the His tag is present. The pPICZαBCysHis vector in addition contains a Cys immediately before the six His residues.

Expression and Purification of MFE-RGD and MFE-RGE in E. coli

The MFE-RGD/pUC119 and MFE-RGE/pUC119 plasmids were electroporated into competent E. coli TG1 cells and grown on 2xYT, containing ampicillin (100 µg/ml) and 1% glucose plates at 37° C. Single colonies were used to inoculate 10 ml of 2xYT, containing ampicillin (as above) and 1% glucose media and after 1:500 dilution were grown in 50 ml of 2xYT, ampicillin (as above) and 0.1% glucose at 37° C. until the $OD_{600nm}$ was 0.9. Protein expression and secretion into the media was induced by addition of 1 mM isopropyl-β-D-thiogalactoside (IPTG, Sigma) and grown at 30° C., O/N. The supernatant was separated from the cells by centrifugation at 4,000 rpm for 20 min.

Purification by Qiagen Ni-NTA.

MFE-RGD and MFE-RGE proteins were purified under native conditions from bacterial supernatant using the Qiagen Ni-NTA Spin Column kit broadly according to the manufacturer's instructions. Briefly, a spin column holding a nickel-containing resin was equilibrated with "Lysis Buffer" (see below) before supernatant containing the 6xHis-tagged protein was spun through and the column washed to remove non-specifically bound material. During this procedure exposed his-tags bind to the nickel resin, and are therefore retained specifically in the column. His-tagged proteins were then eluted by two spins with an imidazole buffer. The manufacturer's instructions were followed with amendments as follows: bacterial supernatant was loaded directly onto the equilibrated column (thereby avoiding the lysis steps) and this step repeated until approximately 4.8 ml bacterial supernatant had passed through each column. Buffer recipes were altered as follows: "Lysis Buffer": PBS, 300 mM sodium chloride; "Wash Buffer": PBS, 300 mM sodium chloride, 20 mM imidazole; "Elution Buffer": PBS, 300 mM sodium chloride, 250 mM imidazole. Bound protein was eluted with 2×200 µl Elution Buffer and the two fractions dialysed separately against PBS using Slide-a-lyser dialysis cassettes (Perbio Science UK Ltd, Cramlington, UK) according to the manufacturer's instructions. Dialysed protein was removed from the Slide-a-lyser and stored at −80° C.

Purification by Streamline

Hundred fifty ml of clarified supernatant was dialysed against three changes of PBS and NaCl was added to a final concentration of 1M. The proteins were purified by Streamline™ Chelating (Amersham Biosciences). The matrix was charged with 5 volumes of 0.1M $CuSO_4$ for 5 min, excess $CuSO_4$ was washed off with 5 volumes of $dH_2O$ and equilibrated with 10 volumes of binding buffer (PBS/1M NaCl). The dialysed supernatant was mixed with the 1.5 ml of charged matrix and poured into a small column. Non-specific bound proteins were washed off the column with PBS/1M NaCl followed by 40 mM Imidazole/PBS/1M NaCl. The proteins were eluted with 200 mM Imidazole/PBS/1M NaCl.

Figure 9:
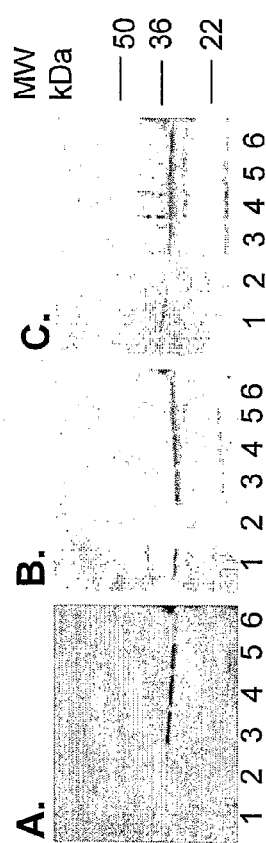
FIG. 9. IMAC purification of hMFE, hMFE23-RGD and hMFE23-RGE. Western blotting of hMFE (A), hMFE23-RGD (B) and hMFE23-RGE (C) using anti-His$_4$. Samples were applied as follows: supernatant (lane 1), PBS wash (lane 2), 40 mM imidazole wash (lane 3), 200 mM imidazole wash (lane 4), 200 mM imidazole wash after dialysis against PBS (lane 5) and EDTA wash (lane 6).

The matrix was then washed with 5 volumes of 0.1M EDTA. Each washing and elution step was done with 4.5 ml volumes. Fractions of interest were pooled and dialyzed against PBS. Protein yields in the 200 mM imidazole fraction measured after dialysis were as follows: hMFE, 0.181 mg/ml, hMFE23-RGD, 0.101 mg/ml and hMFE23-RGE, 0.108 mg/ml. Washing, eluted and dialysed samples revealed by Western Blotting are shown in FIG. 9 A-C.

Expression and Purification of MFEVP1 and NFEVP1 in E. coli

The MFEVP1/pUC119 and NFEVP1/PUC119 plasmids were electroporated into competent E. coli TG1 cells and grown on 2xYT, containing ampicillin (50 µg/ml) and 1% glucose plates at 37° C. Single colonies were used to inoculate 5 ml of 2xYT, containing ampicillin (as above) and 1% glucose media and after 1:500 dilution were grown in 2×500 ml of 2xYT, ampicillin (as above) and 0.05% glucose at 37° C. until the $OD_{600nm}$ was 0.9. Protein expression and secretion into the media was induced by addition of 1 mM isopropyl-β-D-thiogalactoside (IPTG, Sigma) and grown at 30° C., O/N. The supernatant was separated from the cells by centrifugation at 16,000 g for 25 min and was further clarified by filtration through 0.2 µm membranes (Nalgene) and subsequently dialysed three times against PBS. Purification of MFEVP1 and NFEVP1 was by immobilized metal-affinity chromatography (IMAC). Ten ml of Cu-charged Streamline™ chelating resin (GE Healthcare) were incubated with the supernatant, after addition of 1M NaCl, at RT for 1 h. The resin was collected, washed with 1M NaCl/PBS, 40 mM imidazole and bound proteins were eluted with 200 mM imidazole. The 200 mM imidazole protein containing fractions were dialysed against TBS, concentrated by an Amicon stirred cell with a YM3 membrane (Millipore) and further purified by size-exclusion chromatography. Size-exclusion chromatography was performed on Superdex75 column in Tris buffered saline, pH 7.5 (TBS) at 1.5 ml/min. MFEVP1 and NFEVP1 eluted as two peaks, representing the monomeric (67 ml) and dimeric (56 ml) forms. Their molecular weights were estimated from molecular weight standards, Ovalbumin (44 kDa), Carbonic Anhydrase (29 kDa), and Myoglobin (17 kDa) and the monomeric and dimeric forms of MFE.

Expression and Purification of NFEVP1 and HFEVP1 in P. pastoris

For expression of NFEVP1 and HFEVP1 in P. pastoris the NFEVP1/pPICZαBHis and HFEVP1/pICZαBCysHis plasmids, respectively, were linearized with PmeI and transformed into electrocompetent X33 cells (Invitrogen) by electroporation. Transformants were grown on YPDS/100 µg/ml Zeocin (Invitrogen, Karlsruhe, Germany) plates. Single colonies were screened for protein expression and for inserts by PCR with the 5'AOX and 3'AOX primers. The colony with highest protein expression was stored in 20% glycerol at −80° C. NFEVP1 and HFEVP1 were produced by fermentation and initial purification involved expanded bed adsorption immobilized metal affinity chromatography (EBA-IMAC), which also concentrates the proteins, following previously described procedures. (22;23) The 200 mM imidazole EBA-IMAC eluate fraction, containing either NFEVP1 or HFEVP1, were dialysed into PBS. To the concentrate 1M NaCl was added and this was applied to a Ni2+ charged HiTrap Chelating HP lid affinity column (GE Healthcare) for further concentration. Elution in 1 ml fractions was by 500 mM imidazole/1M NaCl/PBS. The diabody containing eluate (2 ml) was further purified by size-exclusion chromatography on a Superdex 75 column in PBS, with a flow rate of 1.5 ml/min.

SDS-Polyacrylamide Gel Electrophoresis (PAGE) and Western Blot Analysis

Proteins were analysed by SDS/PAGE using Tris/Glycine Gels (Invitrogen) and stained with Coomassie brilliant blue.

Western Blot Analysis

Proteins separated by SDS-PAGE were transferred to a PVDF membrane (Bio~Rad) at 125 mA for 90 min. For detection with specific antibodies, the membrane was blocked with 5% milk proteins (Marvel)/PBS for 2-16 h at RT. Detection was performed by incubation with mouse anti-His4 (1:1000 dilution) followed by incubation with HRP-conjugated sheep anti-mouse IgG (1:1000 dilution, GEHealthcare). Both antibodies were diluted in 1% milk proteins/PBS (w/v) and incubation was for 1 h at RT. Final staining was achieved by incubation with 0.25 mg/ml 3,3'-diaminobenzidine (DAB, Sigma) with $H_2O_2$ (1/2000). Washing steps consisted of five washes with 0.1% Tween 20/PBS (v/v) followed by three PBS washes.

Binding of MFE CDR3 VH Loop Variants and Anti-αv Antibody to Immobilized αvβ6 and αvβ3 by ELISA Ninety-six-well plates (Nunc-Immuno™ Plates, Maxi Sorp, Nalge Nunc International) were coated with 100 μl/well of 1 μg/ml of αvβ6 or 3 μg/ml of αvβ3 (Chemicon International, Harrow, UK) in Tris buffered saline (TBS), pH 7.5 at RT for 1 h or TBS as a control. The plate was washed 2 times with 0.1% Tween 20 in TBS followed by 8 washes with TBS, and 150 μl/well of 5% Marvel in TBS was added for 1 h at RT to block non-specific binding. The plate was washed as above but the TBS solutions contained 1 mM $MgCl_2$, 1 mM $MnCl_2$ and 1 mM $CaCl_2$ (TBSM), and dilutions of MFE, MFEVP1, NFEVP1 and HFEVP1 and mouse anti-αv (1:1000, Chemicon International, Harrow, UK) in 1% Marvel in TBSM were added (100 μl/well). The plate was incubated for 1 h at RT, washed, and incubated for 1 h with 100 μl/well of rabbit anti-MFE and with anti-αv for mouse anti-αv wells (1:1000), washed and incubated for 1 h with 100 μl/well of HRP-conjugated goat anti-rabbit IgG (Sigma, 1:1000 dilution) and with sheep HRP-labelled anti-mouse IgG (GE Healthcare, 1:1000 dilution) for anti-αv wells. Bound samples were detected by applying 100 μl of the substrate o-phenylenediamine dihydrochloride (OPD, Sigma) in citrate buffer pH 5.0; the reaction was stopped with 100 μl of 4M HCl and the absorbance read at 490 nm on a Dynex Technologies Plate Reader. In experiments testing the metal dependence of MFE CDR3 loop variants binding, the diluent was TBS containing 10 mM EDTA (pH 7.5) and all washing steps included 10 mM EDTA.

Binding of MFE CDR3VH Loop Variants and hMFE23-RGD, hMFE23-RGE and hMFE to Immobilized CEA by ELISA Ninety-six-well plates (as under Binding of MFE CDR3VH Loop Variants to immobilized αvβ6 by ELISA) were coated with 100 μl/well of CEA at 1 μg/ml in PBS or PBS as a control, washed with twice with PBS on an automatic plate washer (Thermo Labsystems) and blocked with 5% Marvel in PBS. MFEVP1, NFEVP1, MFE, hMFE23-RGD, hMFE23-RGE and hMFE were diluted in 1% Marvel in PBS and 100 μl added to the wells in triplicate, washed as above, incubated with rabbit anti-MFE (1:1000 dilution) for MFEVP1, NFEVP1, MFE and with mouse anti-His4 (1:1000 dilution, Qiagen Ltd.) for hMFE23-RGD, hMFE23-RGE and hMFE washed once with 0:1% Tween 20/PBS and four times with $H_2O$, and incubated with HRP-conjugated goat anti-rabbit IgG (1:1000 dilution) for MFEVP1, NFEVP1, MFE and with HRP-conjugated sheep anti-mouse IgG (1:1000 dilution, GE Healthcare) for hMFE23-RGD, hMFE23-RGE and hMFE. After washing as above with 0.1% Tween-20/PBS and $H_2O$ binding was detected with OPD and absorbance read at 490 nm (as under Binding of MFE CDR3VH loop variants to immobilized αvβ6 and αvβ3 by ELISA).

Flow Cytometric Analysis of MFE and MFE Loop Variants' Binding to LS-174T Cells

LS-174T cells were washed twice with PBS and detached with trypsin/EDTA (Cambrex). On average $5 \times 10^5$ cells were incubated with 50 μg/ml of MFEVP1, NFEVP1 and MFE and washed with PBS. Detection of binding was first by incubation with rabbit anti-MFE IgG (1:100 dilution), washing with PBS and second by incubation with 1 μg of R-Phycoerythrin (R-PE)-conjugated goat anti-rabbit IgG (Invitrogen, Karlsruhe, Germany) followed by washing with PBS. All incubation steps were carried out for 60 min at 4° C. in 100 μl PBS containing 0.1% (w/v) Bovine Serum Albumin (BSA) and 0.1% (w/v) sodium azide. In control experiments the rabbit anti-MFE IgG was omitted. Cells were fixed (IntraStain kit, DakoCytomation) and analysed by flow cytometry on a FACSCalibur™ cytometer (Becton Dickinson, Oxford, UK).

Flow Cytometric Analysis of MFEVP1 and MFE Binding to the αvβ6 Expressing Cell Line, A375Pβ6 and the Parent Cell Line, A375Ppuro A375P6 and A375Ppuro cells (generated as described previously (25)) were washed once in Dulbecco's modified Eagle's medium (DMEM) supplemented with 0.1% (w/v) Bovine Serum Albumin (BSA) and 0.1% (w/v) sodium azide (DMEM 0.1/0.1) and re-suspended in an appropriate volume. 50 μl of this suspension containing approximately $2 \times 10^5$ cells was transferred to individual wells of V-bottomed 96-well plates and mixed with 50 μl of MFEVP1, MFE and 10D5 (Chemicon International, Harrow, UK) at various concentrations. After incubation at 4° C. for 60 minutes, cells were washed two times with 150 μl DMEM 0.1/0.1. Cells were re-suspended in 50 μl mouse Tetra-His antibody (Qiagen, Crawley, UK) diluted 1:100 in DMEM 0.1/0.1 and incubated for a further 35 minutes at 4° C. Cells were then washed twice with 150 μl DMEM 0.1/0.1 as above. Alexa-488-conjugated goat anti-mouse (1:200 dilution in DMEM 0.1/0.1; Molecular Probes) was then added and cells incubated for a further thirty minutes at 4° C. Cells were washed three times as above and transferred to 5 ml centrifuge tubes (BD Falcon 352054, supplied by VWR, UK). Cells were analysed on an LSR-1 FACS flow cytometer (Becton Dickinson, Oxford, UK) using CellQuest software.

Flow cytometric analysis of anti-αvβ6, anti-αvβ8, anti-αv5, anti-αvβ3 and αvβ1 binding to the αvβ6 expressing cell line, A375Pβ6 and the parent cell line, A375Ppuro. Flow cytometric analysis of RGD-directed integrin expression—A375Ppuro and A375Pβ6puro cells were detached with trypsin/EDTA, resuspended in DMEM 0.1/0.1 to $2.10^5$ cells/50 μl and mixed with 50 μl of anti-integrin antibodies (at 10 μg/ml). After 45 minutes at 4° C. the cells were washed twice with DMEM 0.1/0.1 and bound antibodies detected with 50 μl of 1:200 dilutions of Alexafluor-488 conjugated anti-mouse antibodies for 30 minutes at 4° C. After two washed samples were analysed by flow cytometry as above. Negative controls received similar concentrations of mouse IgG (Dako).

Immunofluorescence confocal microscopy of internalisation of NFEVP1.

A375Pβ6 and A375Ppuro cells were trypsinized, re-suspended in DMEM, containing L-glutamine, supplemented with 10% heat-inactivated fetal bovine serum. Cells (~$2 \times 10^5$) were seeded in 2 ml of the above media in $24=^2$ dishes containing glass coverslips and allowed to attach for 48 hrs at 37° C. The media was removed and exchanged with DMEM containing 1% heat-inactivated fetal bovine serum and 50

μg/mL of NFEVP1 and either directly incubated at 10 min, 30 min, 1 hr and 3 hr at 37° C. or first pre-incubated at 4° C. for 1 hr, upon which the scFv was removed, and the cells were shifted to 37° C. After incubation cells on the coverslips were washed with PBS, containing 2 mM $Ca^{2+}$ and 1 mM $Mg^{2+}$, fixed in 4% paraformaldehyde/PBS for 20 min on ice, washed with PBS and incubated with 10 mM ammonium chloride for 10 min at RT, washed, permeabilized with 0.1% Triton X-100 for 5 min on ice, washed and blocked with 3% (w/v) BSA/PBS for 20 min at RT. Cells were washed, and stained with 10 μg/mL Affini Pure Rabbit anti-mouse IgG (H+L, Jackson Immune Research) in 1% (w/v) BSA/PBS, washed and stained with 10 μg/mL Alexa Fluor 546® labelled Goat anti-rabbit IgG (H+L, Molecular Probes, Invitrogen), containing Hoechst trihydrochloride (1:5000) in 1% (w/v) BSA/PBS, washed three times with PBS and one time with $H_2O$. All washes were three times with PBS if not indicated otherwise. Coverslips were mounted on slides using ProLong Gold antifade (Molecular Probes, Invitrogen). Cells were visualized with a Olympus® confocal scanning microscope (Olympus, London, UK).

Migration Assays

Haptotactic cell migration assays were performed using matrix coated polycarbonate filters (8 μm pore size, Transwell®, Becton Dickinson, Oxford, UK). The membrane undersurface was coated with LAP (0.5 μg/ml) in α-MEM for 1 hour at 37° C. and blocked with migration buffer (0.1% BSA in α-MEM) for 30 minutes at 37° C. For blocking experiments, cells were incubated with MFEVP1, NFEVP1 and 10D5 antibody (at 10 μg/ml, Chemicon International, Harrow, UK) for 60 minutes at 4° C. prior to seeding. The lower chamber was filled with 500 μl of migration buffer, following which cells were plated in the upper chamber of quadruplicate wells, at a density of $5 \times 10^4$ in 50 μl of migration buffer and incubated at 37° C. for 20 hours. Following incubation, the cells in the lower chamber (including those attached to the undersurface of the membrane) were trypsinised and counted on a Casy 1 counter (Sharfe System GmbH, Germany).

Fourier-Transform Infrared (FT-IR) Spectroscopy of NFEVP1 and MFE

FT-IR spectra were recorded using a Perkin-Elmer1750 FT-IR spectrometer equipped with a fast recovery TGS type detector. NFEVP1 at 0.47 mg/ml, MFE at 0.59 mg/ml and PBS control were dialysed with three buffer changes at 4° C. into 20 mM Phosphate buffer, pH7.5 and subsequently lyophilized. NFEVP1 and MFE were dissolved in $^2H_2O$ to a final concentration of 10 mg/ml and control at an equivalent volume. Eight μl of each protein and control were placed into the 6 μm recess on one of the two specialists-made $CaF_2$ windows (Feinoptische Werkstatt, Berlin, Germany) that was mounted inside a Beckman FH-01 CFT micro-cell. For denaturation experiments the cell was exposed to temperatures from 25° C. to 85° C. in steps of 2-5° C. using an attached waterbath. Before each spectrum acquisition samples were maintained at the desired temperature in order to stabilize the temperature inside the cell (10 min). A total of 200 scans were acquired at each temperature for the denaturation measurements, whereas for comparison of NFEVP1 and MFE secondary structural elements 1000 scans were acquired at 30° C. each. The absorbance spectra were first subtracted by their respective buffer control followed by calculation of the second derivative spectra using a 13 data point Savitsky-Golay smoothing function.

Inhibition of Cell Adhesion

The ability of modified and unmodified scFv antibodies to inhibit the αvβ6-specific adhesion of [$^{51}$Cr]-labelled 3T3136.19 fibroblast cells to LAP was performed as described previously (31).

Results

Construction, expression in E. coli and purification of scFv MFE VH loop variants, hMFE23-RGD (also known as hMFE-RGD) and hMFE23-RGE (also known as hMFE-RGE) and binding of hMFE23-RGD and hMFE23-RGE to CEA and αvβ6.

The MFE antibody has no αvβ6-binding capability. Initial attempts to confer affinity for αvβ6 using site-directed mutagenesis to delete the CDR 3 loop residues 123-128 of the VH chain of MFE, which are known to be critical for CEA binding (Boehm et al., 2000b), and replace them with the peptide sequence RGDLATL (SEQ ID NO: 44), an RXDLXXL (SEQ ID NO: 45) motif based on the sequence of TGFβ1 Latency Associated Peptide (LAP), failed. In addition, it was decided to insert one alanine residue prior to the RGD, as bioinformatic modeling suggested that this might improve the presentation of the motif by increasing its solvent accessibility. As the aspartate residue is critical to integrin binding (Humphries, 1990), an ARGELATL (SEQ ID NO: 46) recombinant was also constructed as a control. The proteins were expressed in E. coli and secreted into the supernatant. Proteins were purified from the bacterial supernatants using Nickel spin columns and visualised by SDS-PAGE followed by Western blotting and detection with an anti-4xHis monoclonal antibody (FIG. 9).

Figure 10:
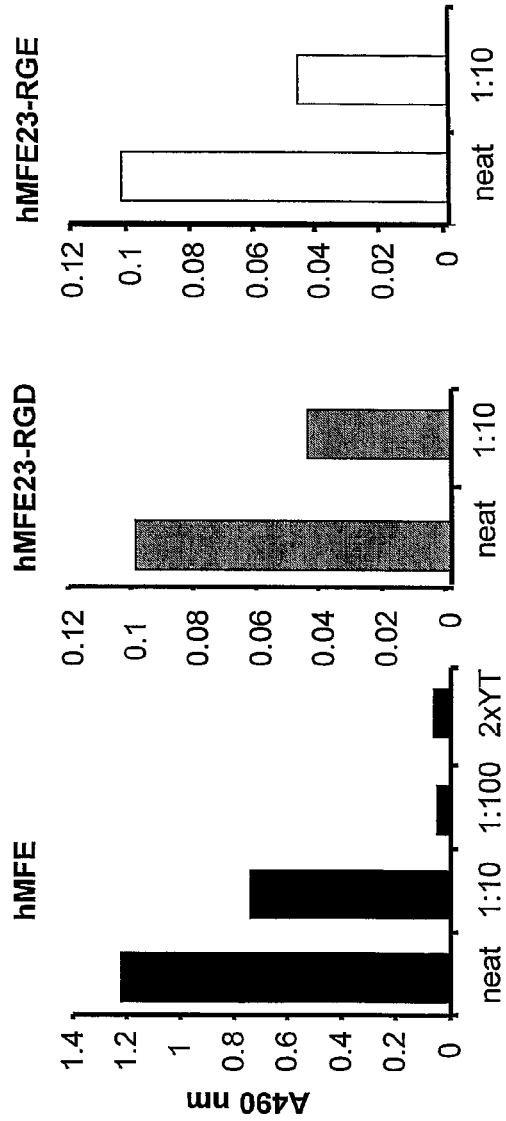
FIG. 10. Binding of hMFE, hMFE23-RGD and hMFE23-RGE to CEA. hMFE, hMFE23-RGD and hMFE23-RGE as neat supernatant, 1:10 dilution and 1:100 dilution for hMFE and 2YT were added to immobilized CEA. Binding was detected with mouse anti-His$_4$ and HRP-conjugated sheep anti-mouse IgG.
Figure 11:
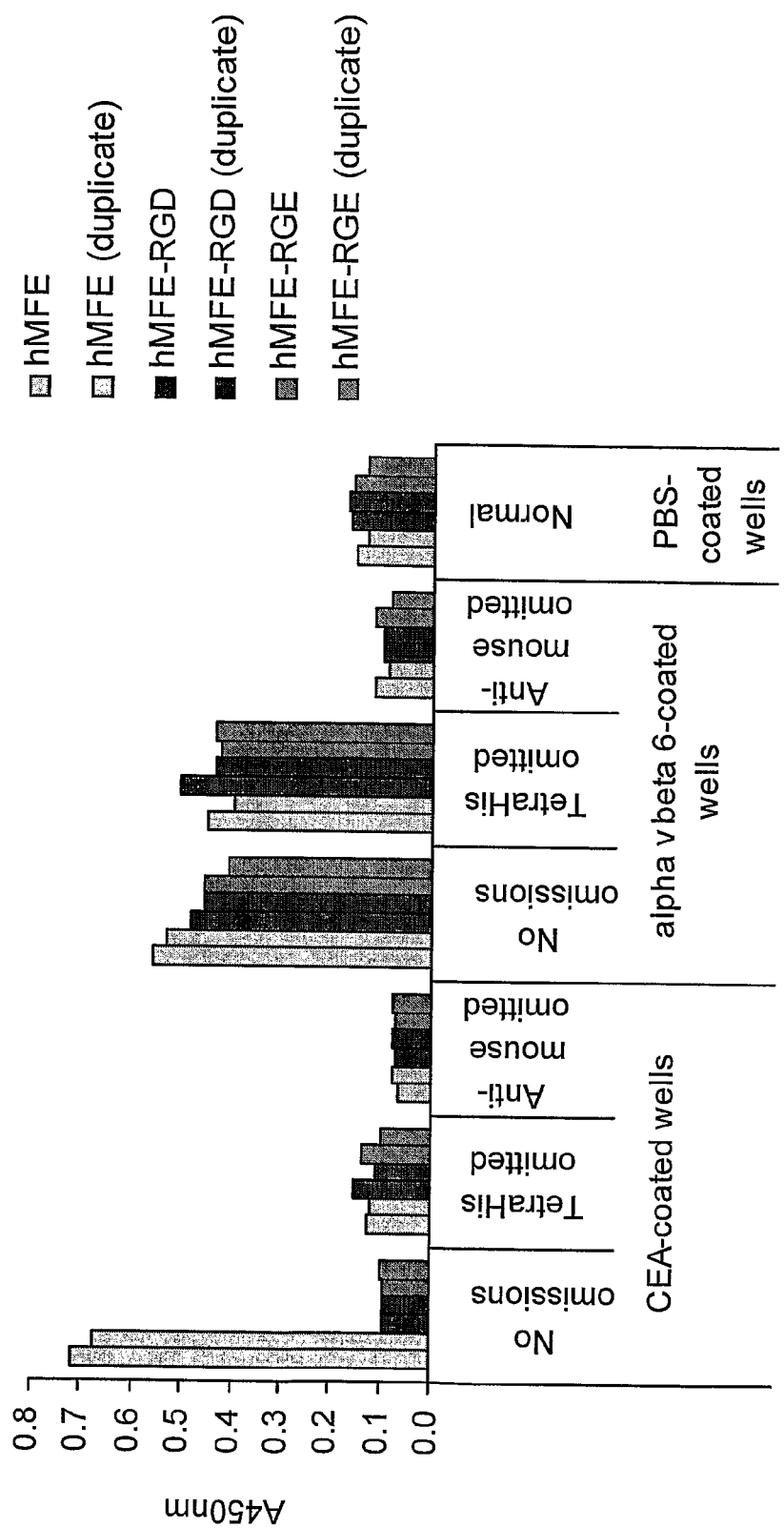
FIG. 11. Detection of His-tagged hMFE, hMFE-RGD and hMFE-RGE proteins binding to immobilised CEA, rsαvβ6 or PBS control. 96-well plates were coated with 1 μg/ml CEA, 1.5 μg/ml rsαvβ6 or PBS, and residual non-specific binding sites blocked with 1% Tween 20, 5% BSA. Purified proteins were diluted 1/50, added to the wells, and allowed to bind for one hour before washing and detection with Qiagen TetraHis (mouse anti-4×His) followed by peroxidase-conjugated anti-mouse. Bound peroxidase was visualised by the colour change reaction on addition of the TMB+ reagent (DAKO), and quantitated by the absorbance at 450 nm after the reaction had been stopped with 1N H$_2$SO$_4$. TetraHis and anti-mouse were omitted from some control wells, as shown. Data shown are the results of duplicate wells.

The parent scFv, MFE, binds to CEA so it was important to establish whether hMFE23-RGD and hMFE23-RGE would remain some of this binding activity. Results showed that hMFE23-RGD and hMFE23-RGE showed some residual binding to immoblised CEA (FIG. 10). The ability of hMFE23-RGD and hMFE23-RGE to bind αvβ6 was then investigated. Results showed that both hMFE23-RGD or hMFE23-RGE failed to show any measurable binding to immobilised αvβ6. Although there was a high level of background, the hMFE23-RGD gave no signal over and above that of the negative control hMFE23 (FIG. 11).

Construction, Expression in E. coli and the Yeast, P. pastoris, and Purification of scFv MFE VH Loop Variants, MFEVP1, NFEVP1 and shMFE(P)CDR2VP1

Figure 2:
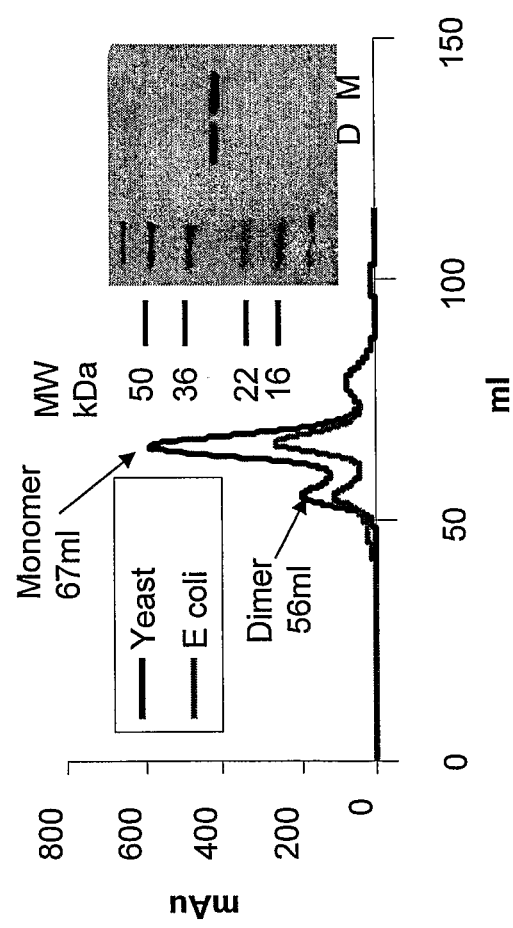
Figure 3A:
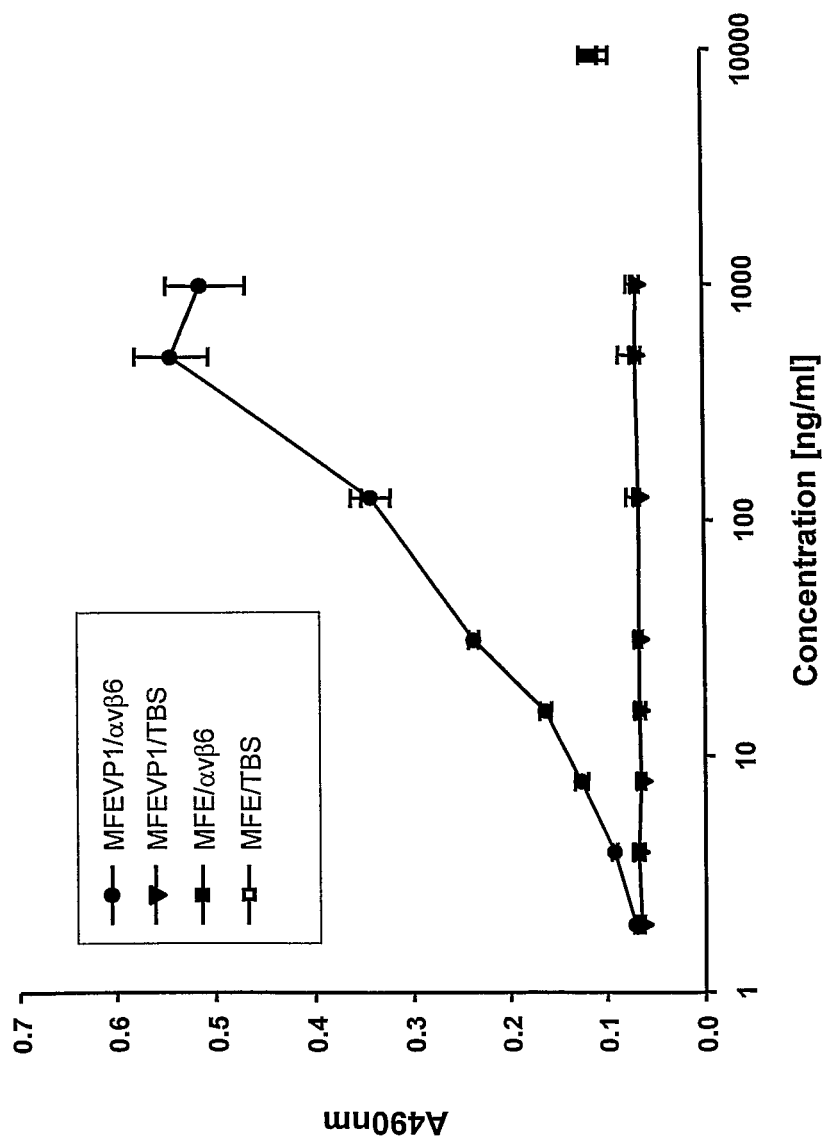
Figure 3B:
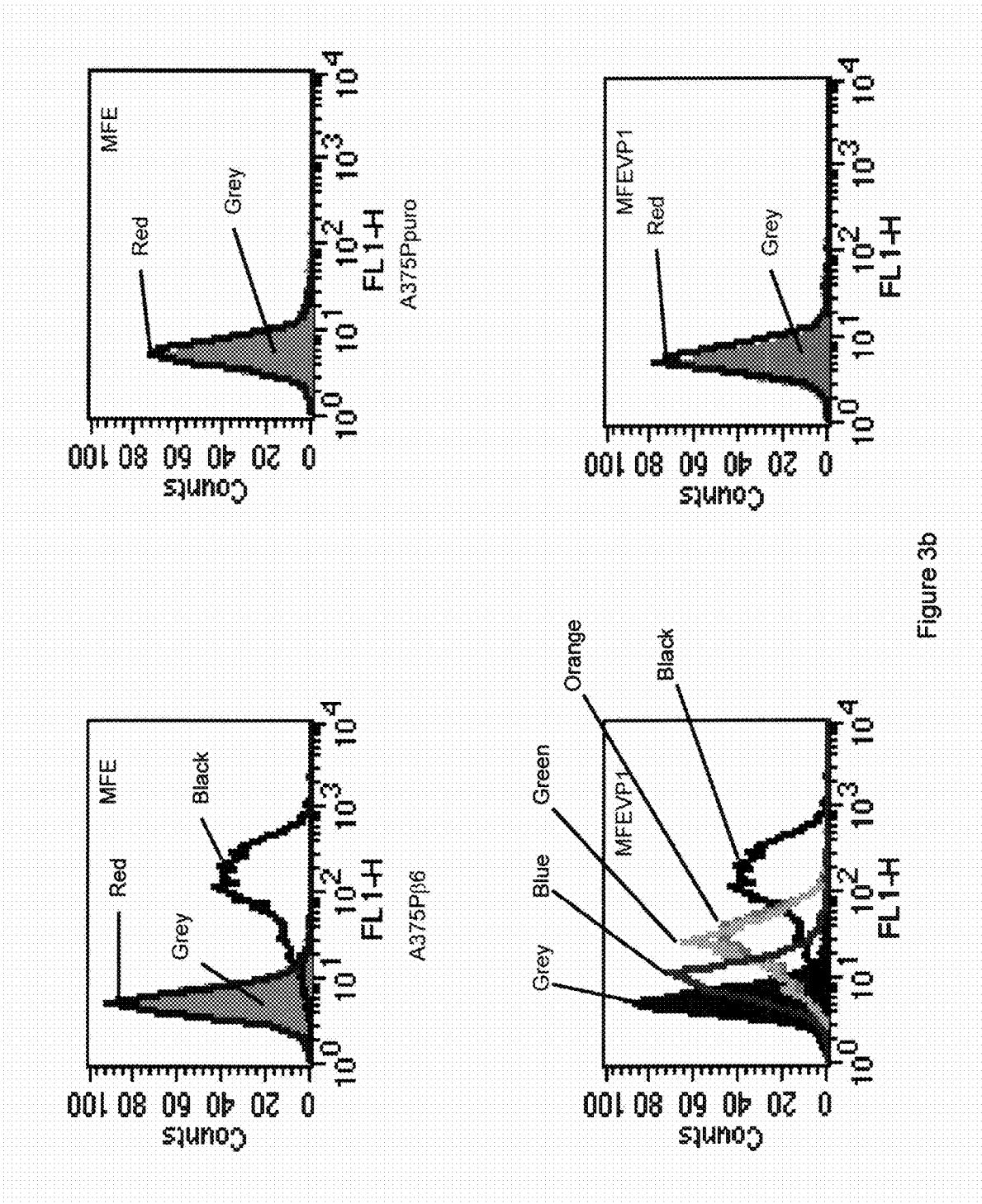
Figure 3C:
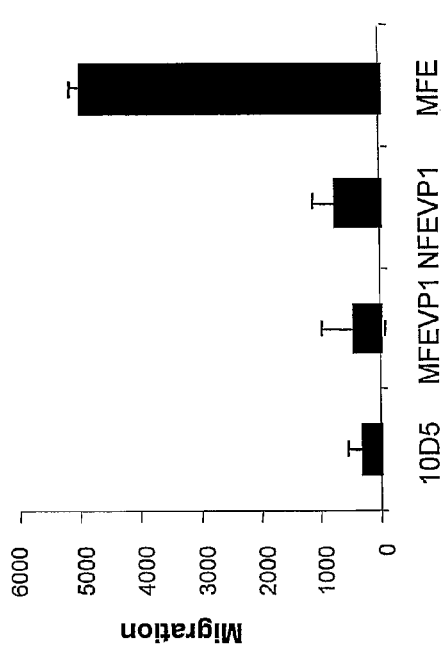
Figure 3D:
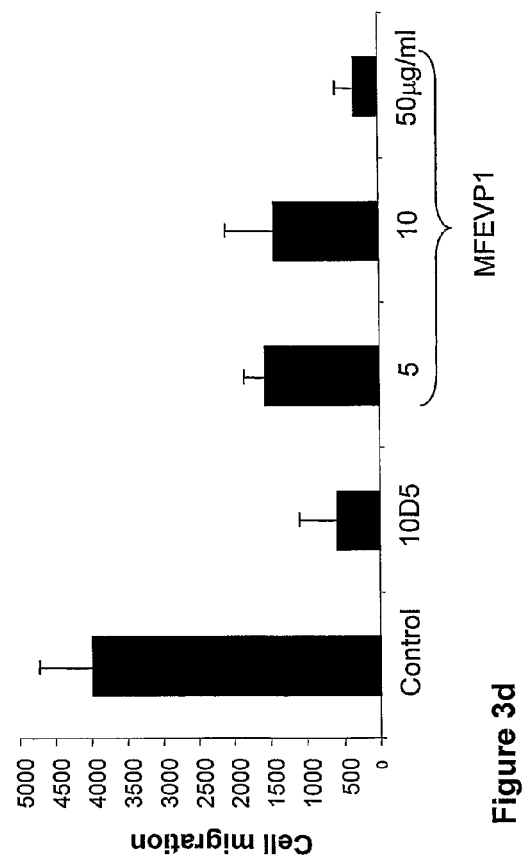
Figure 4A:
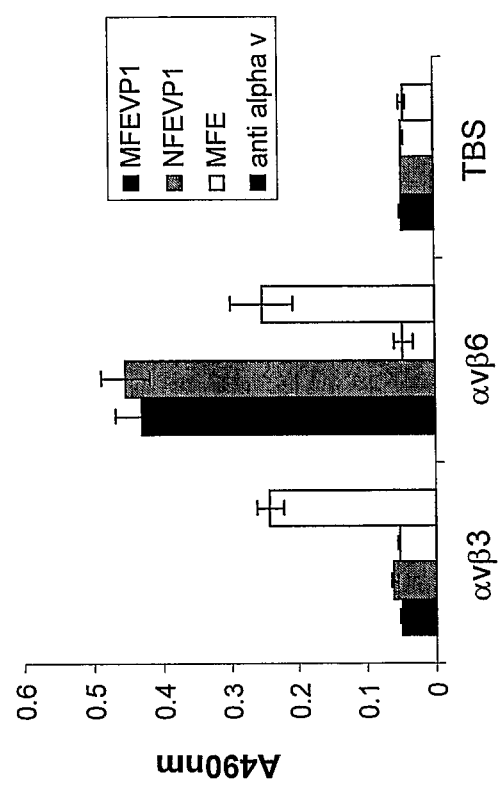
FIG. 4. MFEVP1 and NFEVP1 bound to immobilized αvβ6 and not αvβ3 by ELISA. A375Ppuro and A375Pβ6 expressed αvβ8, αvβ5, αvβ3 and α5vβ1 at similar levels. αvβ6 expression is only detected by the A375Pβ6 cells. (a) Binding of MFEVP1, NFEVP1 and MFE [all at 20 μg/m1] was detected with rabbit anti-MFE followed by goat horseradish peroxidise (HRP)-labelled anti-rabbit IgG antibodies and, to detect integrin immobilization, wells were also incubated with mouse anti-αv followed by sheep HRP-labelled anti-mouse IgG. The data represent the mean of triplicate measurements and error bars represent the standard deviation at each data point. (b) A375Ppuro and A375Pβ6 cells were incubated with MFEVP1 and NFEVP1 antibodies. Negative controls (white histograms) had secondary antibody only.
Figure 4B:
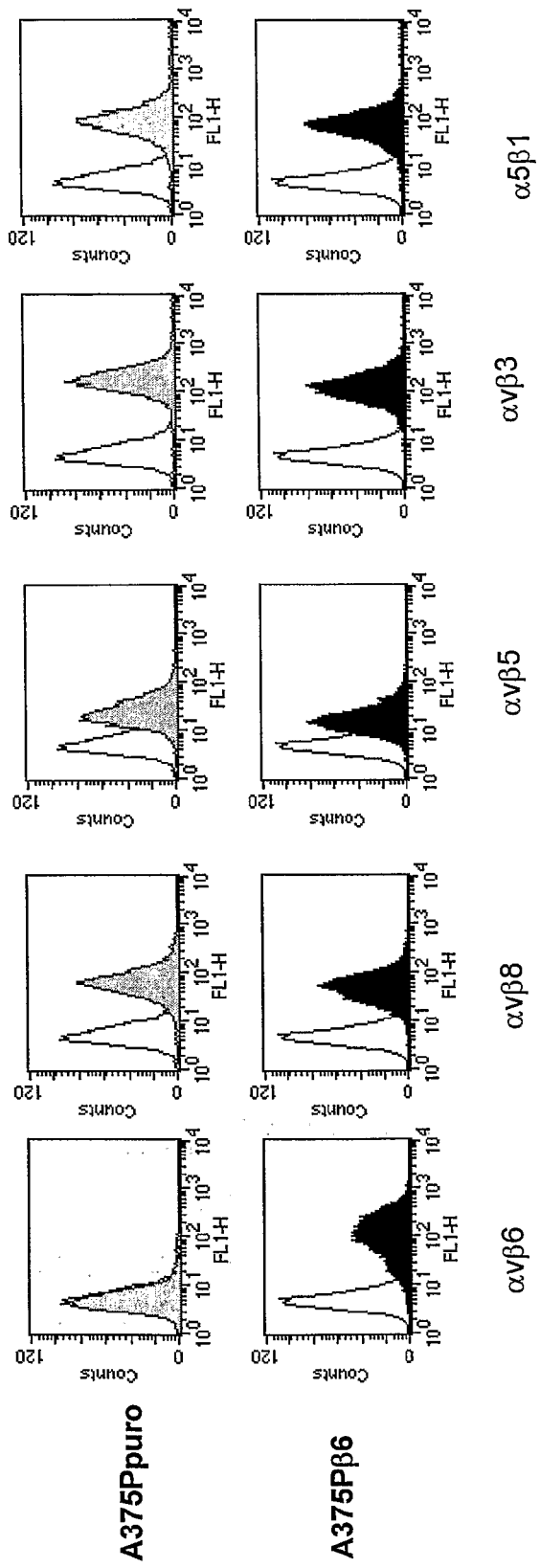
Figure 5A:
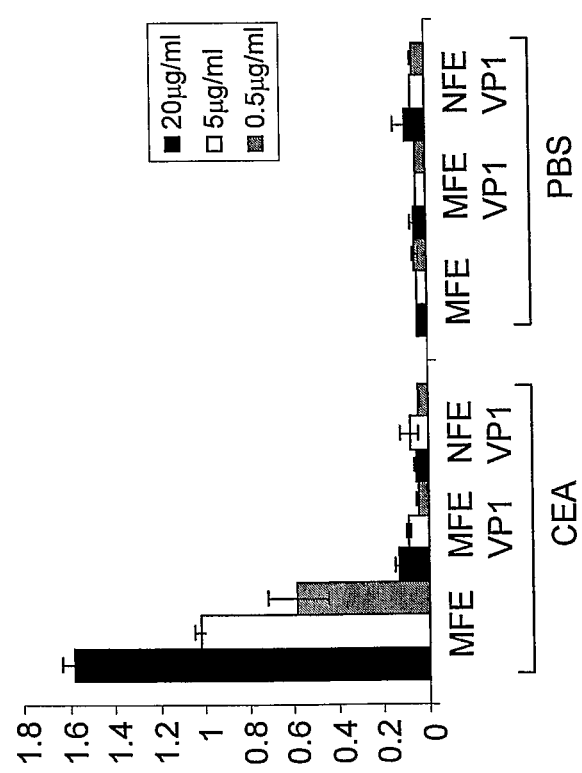
FIG. 5. MFEVP1 showed residual binding to immobilized CEA and bound to CEA-expressing LS-174T cells. CEA binding was eliminated by the $_{100b}$ to $_{P100b}$ mutation. (a) MFEVP1 and NFEVP1 (at three different concentrations) were added to immobilized CEA and PBS wells. Binding was detected with rabbit anti-MFE followed by goat horseradish peroxidise (HRP)-labelled anti-rabbit IgG. The data represent the mean of triplicate measurements and error bars represent the standard deviation at each data point. (b) CEA-expressing LS-174T cells were incubated with MFEVP1, NFEVP1 and MFE (all at 50μg/m1). Binding was detected by Flow Cytometry with rabbit anti-MFE IgG followed by R-phycoerythrin (R-PE)-labelled goat anti-rabbit IgG. The Omission Control is the MFE experiment without rabbit anti-MFE IgG. Results are representative of three independent experiments. % GateD Fluorescence Intensities ($7\times10^1$–$10^4$, as indicated) are mean values from three separate experiments of which the mean control values have been subtracted.
Figure 5B:
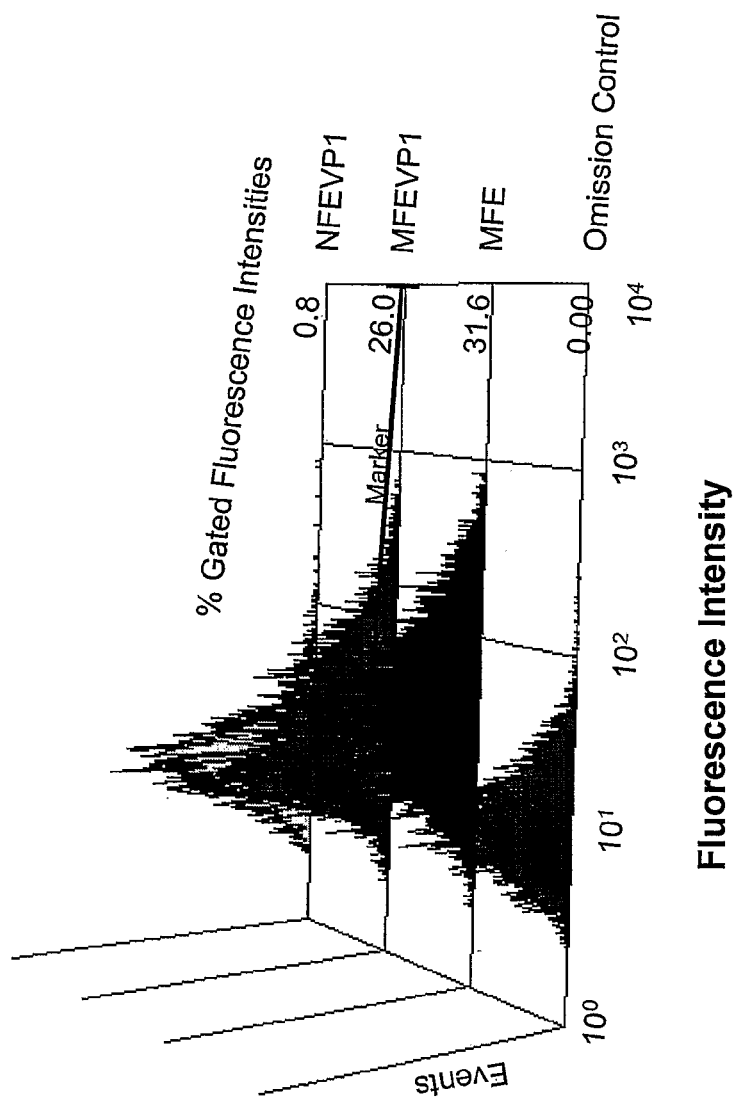
Figure 6A:
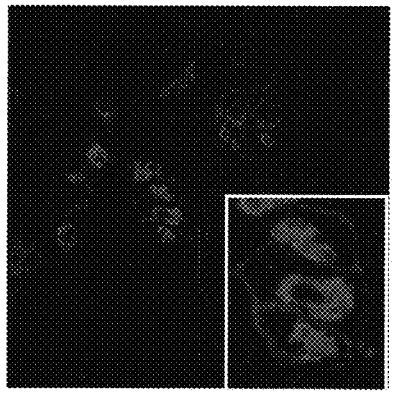
FIG. 6A-FIG. 6C. NFEVP1(P) is internalized by β6-transfected A375P cells as revealed by indirect fluorescence confocal microscopy. β6-transfected (FIG. 6A) and non-transfected(puro) (FIG. 6B) A375P cells were incubated with NFEVP1 for 1 hr at 4° C., the scFv was removed and cells were shifted to 37° C. for the times indicated. Cell surface bound and internalized NFEVP1 was detected with rabbit anti-mouse IgG followed by Alexa Fluor®546 labelled goat anti-rabbit IgG(red). In the control experiment (FIG. 6C) NFEVP1 was omitted. Blue reveals nuclear staining with Hoechst.
Figure 6A:
Figure 6A:
Figure 6A:
Figure 6A:
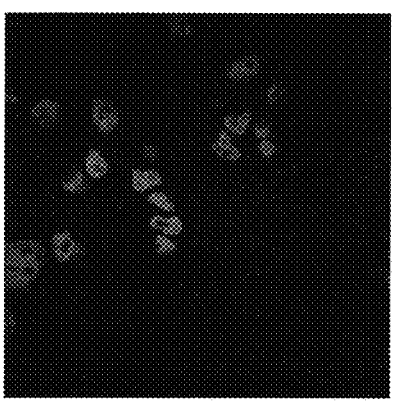
Figure 6A:
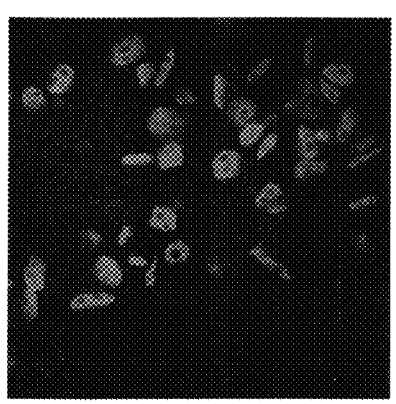
Figure 6B:
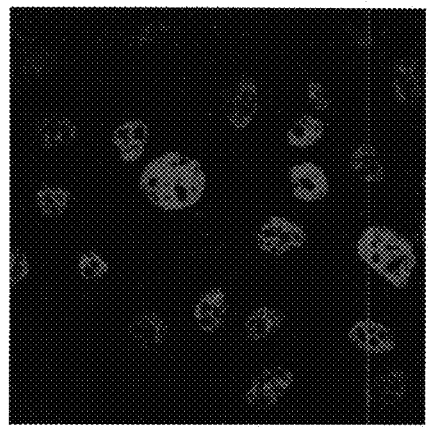
Figure 6B:
Figure 6B:
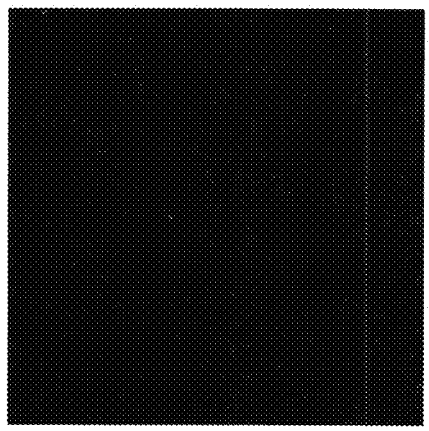
Figure 6B:
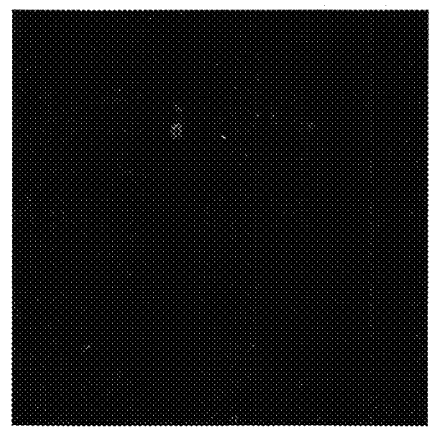
Figure 6B:
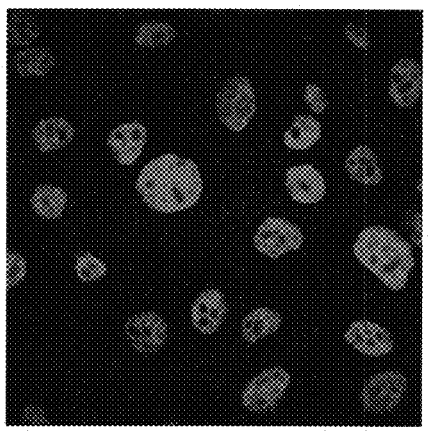
Figure 6B:
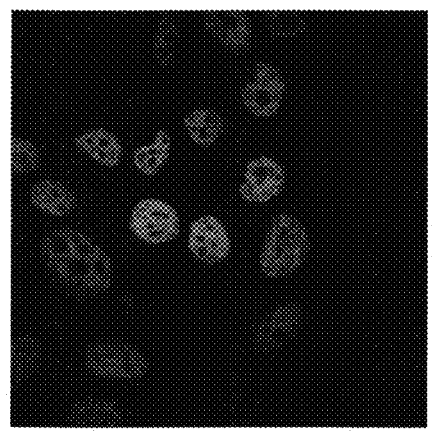
Figure 6C:
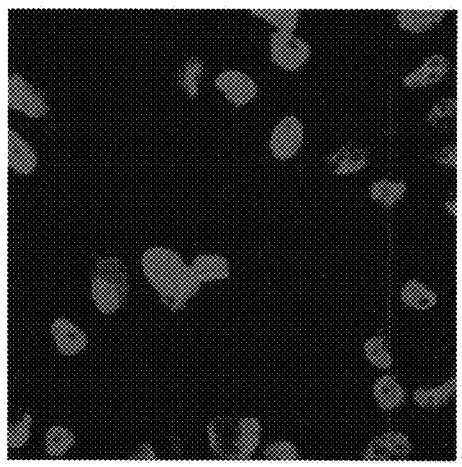
Figure 6C:
Figure 6C:
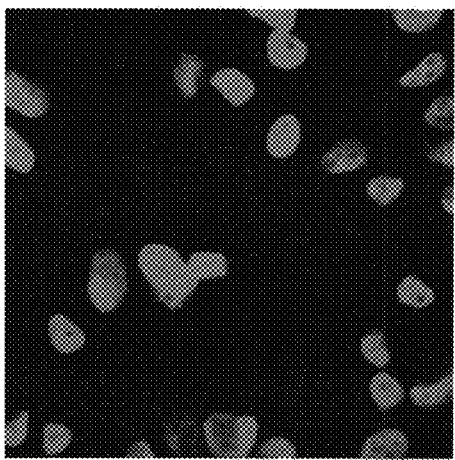

For construction of a αvβ6-binding MFE the peptide sequence from $A_{140}$ to $A_{156}$ of the viral coat protein VP1 of the Foot-and-Mouth disease virus (FMDV) was inserted at the tip of the CDR3 loop of the VH chain of MFE, between T98 and G99 (using Kabat nomenclature as shown in FIG. 1). This VH loop variant of MFE was named MFEVP1. The DNA sequence of MFEVP1 was generated by overlapping PCR as described in Material and Methods. The protein was expressed in *E. coli* and secreted into the supernatant at comparable levels and similar size to the parent molecule, MFE Initial purification and concentration of the protein was obtained by IMAC chromatography. The protein was further purified by size-exclusion chromatography (FIG. 2*a*). MFEVP1 eluted as two distinct peaks, 56 ml and 67 ml, representing the dimeric and monomeric forms, respectively. A further scFv MFE loop variant, NFEVP1, containing the αvβ6-binding sequence of VP1 and a $Y_{100b}$ to $P_{100b}$ mutation in the VH domain was constructed (see FIG. 1*a*) from MFEVP1 by site-directed mutagenesis. Expression and purification in *E. coli* of this protein was similar to MFEVP1. The DNA sequence of NFEVP1 was also cloned into a yeast vector for expression in *P. pastoris*. NFEVP1 was obtained at 56 mg/L after initial EDB-IMAC chromatography, using previously described procedures. (22, 23). NFEVP1 was concentrated and final purification was by size-exclusion chromatography (FIG. 2b). The chromatographic profile of the yeast expressed protein was virtually super imposable to that obtained from E. coli.

A further MFE VH loop variant, shMFE(P)CDR2VP1, was constructed by inserting the $A_{140}$-$A_{156}$ VP1 peptide between the DNA sequences of VH CDR2 residues E53 and N54 of the shMFE$^2$ sequence (which contains the $Y_{100b}$P mutation). This DNA sequence was cloned into a yeast vector and expressed in *P. pastoris*. The expressed protein was analysed by SDS-PAGE and Western blotting, which showed that the protein was stably expressed in yeast.

Binding of MFEVP1 and NFEVP1 to αvβ6 and Inhibition of Migration

The ability of pure monomeric forms of MFEVP1 and NFEVP1 to bind to αvβ36 was investigated. MFEVP1 showed concentration dependent binding to αvβ6 immobilized plates in ELISA when probed with anti-MFE followed by anti-rabbit labelled HRP IgG (FIG. 3*a*). In contrast, the absorbance reading for parent MFE, tested under identical conditions, was similar to background levels. In agreement with metal dependent integrin-ligand binding MFEVP1 did not bind in the presence of EDTA (data not shown).

MFEVP's ability to bind to αvβ6 when expressed on cells was also investigated. MFEVP1 showed concentration dependent binding to β6-transfected A375Pβ6 cells (a retrovirally with 136 cDNA transfected melanoma Cell line (25)) by Flow Cytometry when monitored with mouse anti-His followed by Alexa488-conjugated anti-mouse Fc (FIG. 3*b*). Observed fluorescence shifts were similar for the 5 μg/ml and 0.5 μl/ml concentrations, indicating that MFEVP1 reached almost saturation levels of binding at 0.5 μg/ml. The αvβ6-specific antibody, 10D5, was included as a positive control whereas MFE, the negative control, was not shifted beyond background levels. Neither 10D5, MFEVP1 nor MFE showed binding to the non-transfected parent cell, A375Ppuro (transfected with empty vector), confirming that the observed binding of MFEVP1 to the β6-transfected cell line was specifically to αvβ6.

The VP1-inserted scFvs' ability to functionally inhibit migration of αvβ6-expressing cells was investigated next. VB6 cells, a well characterised retrovirally with β6 cDNA transfected oral SCC cell line (27), were allowed to migrate towards the αvβ6-specifically binding ligand, LAP, which is coated underneath a Transwell filter. Addition of 50 μg/ml of MFEVP1 and the $Y_{100b}$ to $P_{100b}$ mutant, NFEVP1, to VB6 cells considerably inhibited their migration when compared to MFE (FIG. 3*c*). The function blocking αvβ6-specific 10D5 antibody added at 10 μg/ml showed similar levels of inhibition of cell migration of VB6 cells as the scFvs. The inhibition of migration was concentration dependent as shown for MFEVP1 (FIG. 3*d*).

Investigation of Binding of scFv MFE VH Loop Variants to Integrins other than αvβ6

Cross reactivity of MFEVP1 and NFEVP1 with integrins other than αvβ6 was first investigated by ELISA, using immobilized αvβ3 and αvβ6, and by cell binding studies using cells expressing a variety of integrins. Results showed that MFEVP1 and NFEVP1 did not bind to immobilized αvβ3 in ELISA when probed with rabbit anti-MFE followed by HRP-labelled anti-rabbit IgG (FIG. 4*a*) whereas binding to αvβ6 was observed. Immobilization of both integrins to the wells was confirmed with an anti-αv antibody. Selectivity of MFEVP1 and NFEVP1 for αvβ6 was also in agreement with the cell binding studies described under "Binding of scFv MFE VH loop variants to αvβ6 and inhibition of migration" (shown in FIG. 3*b*). Because both scFvs did not bind to the non-transfected A375Ppuro cell line, which express αvβ3 at similar levels to the β6-transfected A375Pβ6 cell line (FIG. 4*b*), this agrees with the ELISA results that MFEVP1 and NFEVP1 did not bind at detectable levels to αvβ3. In addition, the A375Ppuro cells also expressed αvβ8, αvβ5 and α5β1 at similar levels to those found on A375Pβ6 cells (FIG. 4*b*) which showed that MFEVP1 and NFEVP1 did also not bind at detectable levels to these integrins.

Binding of MFEVP1 and NFEVP1 to CEA

The parent scFv, MFE, binds to CEA so it was important to establish whether MFEVP1 would remain some of this binding activity. Results showed that MFEVP1 showed residual binding to immobilized CEA in ELISA in a concentration-dependent manner, although considerably below that seen for MFE (FIG. 5*a*) when revealed with rabbit anti-MFE and HRP-labelled goat anti-rabbit IgG. The $Tyr_{100b}$ to $Pro_{100b}$ mutant, NFEVP1, showed no residual binding on ELISA to immobilized CEA.

This same mutation when introduced into MFE had been shown previously to completely abolish binding to CEA (19). The ability of MFEVP1 to bind to CEA when expressed on cells was also investigated. These experiments showed that MFEVP1 bound to the human colon adenocarcinoma cell line LS174T, which is known to express high levels of CEA, when revealed by Flow Cytometry with rabbit anti-MFE followed by goat phycoerythrin-labelled anti-rabbit IgG (FIG. 5*b*). The shift in fluorescence intensity was only slightly below that of the parent molecule, MFE, as measured by gated fluorescence intensity, 53.8% for MFE and 42.5% for MFEVP1. Consistent with the ELISA results the $Tyr_{100b}$ to $Pro_{100b}$ mutant, NFEVP1, showed no binding to theses cells, the observed fluorescence intensity was equal to that of the omission control. The $Tyr_{100b}$ to $Pro_{100b}$ mutation was thus able to eliminate all residual binding of NFEVP1 to CEA as has been seen previously for the parent molecule, MFE.

Internalization of NFEVP1 into β6-Transfected A375P Cells

Having shown binding of NFEVP1 to αvβ6 on cells, we then investigated whether binding of NFEVP1 to αvβ6 on the cell surface resulted in internalization of the scFv in these cells. β6-transfected A375P cells were therefore incubated at 4° C. with NFEVP1 for 1 hr, the scFv was removed and cells were incubated at various temperatures (described under Material and Methods and shown in FIG. 6) at 37° C. After 10 minutes incubation at 37° C. the scFv was seen as a well defined thin line surrounding, at a distance, the nucleus (Hoechst staining and shown in blue) when revealed with rabbit anti-mouse IgG followed by Alexa Fluor® 546 labeled goat anti-rabbit IgG and shown in red; typifying its location in the plasma membrane. After 3 hrs incubation the scFv was diffused and speckled around the nucleus, identifying its location inside the cells. The scFv was also found inside the cells 30 minutes and 1 hrs after incubation of the cells at 37° C. (data not shown). When compared with the equivalent 10 min and 3 hr incubation experiments of NFEVP1 with the A375Ppuro cells and the control experiment where the scFv was omitted it can be concluded that the fluorescence levels were significantly above background level; experiments were recorded and depicted under identical conditions. It was assured that internalization is mediated entirely by αvβ6 and not some other mechanism by pre-incubating the scFv at 4° C. and removing it before incubation at 37° C. as Flow Cytometry results (see above) showed that NFEVP1 bound only to the β6-transfected cells and not the puro cells. However, similar results were obtained when cells were incubated without prior incubation at 4° C. and removal of the scFv (data not shown).

Fourier-Transform Infrared (FT-IR) Spectroscopy of NFEVP1.

Figure 7B:
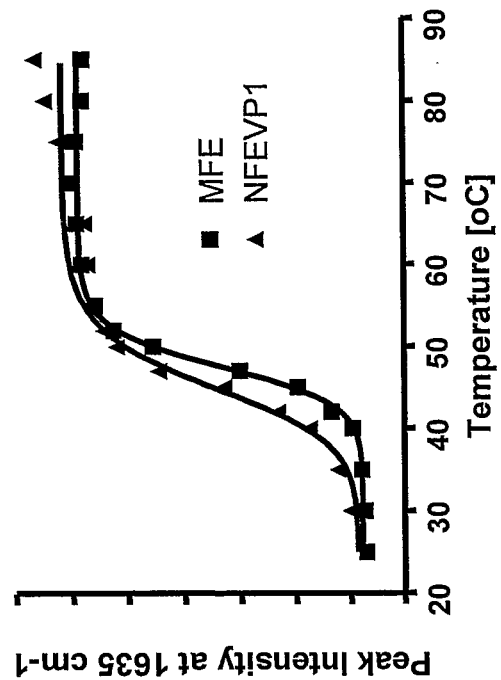
FIG. 7. NFEVP1 and MFE had very similar secondary structure elements and denaturation curves as determined by FT-IR spectroscopy. (a) Second derivative FT-IR spectra of NFEVP1 and MFE were obtained from the absorbance spectra recorded at 30° C. after buffer control subtraction. (b) For the denaturation curve both proteins were heated from 25° C. to 85° C. and the FT-IR spectra were measured. The midpoints of denaturation were obtained from fitting of the peak intensity at 1635 cm$^{-1}$ of the 2nd derivative spectra to a sigmoidal curve as 47° C. for MFE and 45° C. for NFEVP1.
Figure 7A:
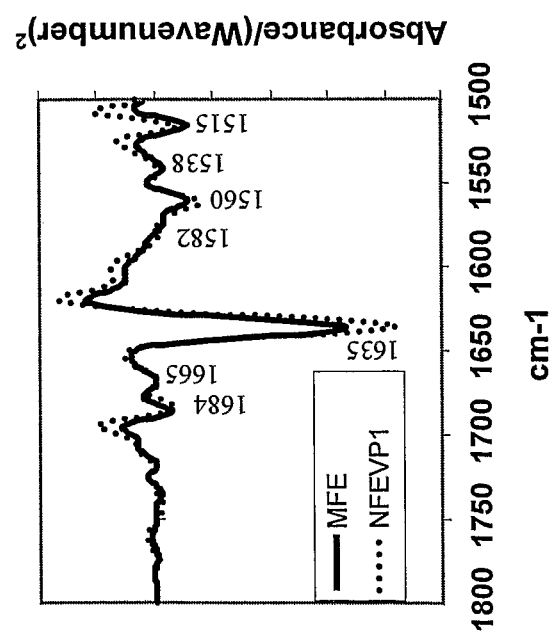

Having obtained pure, monomeric NFEVP1, identified αvβ6 binding and inhibition of migration of αvβ6 expressing cells, it was investigated whether insertion of the 17-mer VP1 peptide had affected the structure and stability of the protein when compared with the parent molecule, MFE. The $2^{nd}$ derivative FT-IR spectra of NFEVP1 and MFE were virtually super imposable. NFEVP1 showed a strong band at 1635 cm-1 in agreement with a protein whose structure consists mainly of β-sheet and shown previously in the x-ray structure of MFE (25). The secondary structural elements associated with the FT-IR bands have been assigned previously for MFE. (26) The intensity of the β-sheet band at 1635 $cm^{-1}$ was used to monitor stability of the protein; with increasing temperature this band will reduce in intensity while the protein denatures. Recording of the denaturing curve and fitting to a sigmoidal curve gave a midpoint of denaturation of 45° C. for NFEVP1 (FIG. 7b). For MFE this temperature was 47° C., identical to the previously reported value (28). Therefore, insertion of the VP1 peptide did not affect the structure of the protein and NFEVP1 had very similar stability when compared to MFE.

Expression, Purification, αvβ6-Binding and Inhibition of Cell Binding of Stabilized Humanized NFEVP1 (HFEVP1)

Figure 8A:
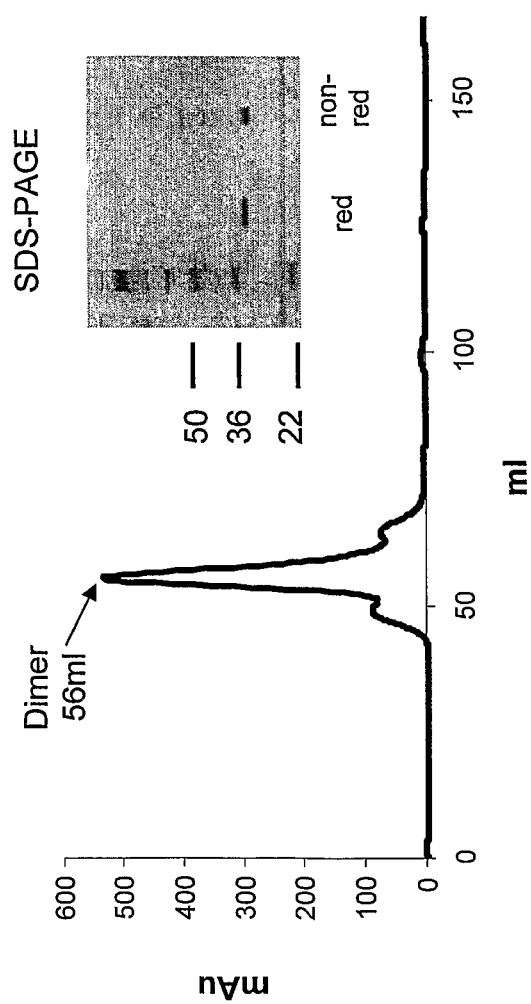
FIG. 8. HFEVP1 eluted almost exclusively as dimer on size-exclusion chromatography (Superdex 75), bound to immobilized αvβ6 in ELISA and inhibited the adhesion of αvβ6-expressing 3T3β6.19 cells to LAP. (a) *P. Pastoris* expressed HFEVP1 was applied after EBD-IMAC and Ni$^{2+}$-affinity chromatographies. Twelve percent Tri-glycine SDS-PAGE under reducing and non-reducing conditions is shown of the dimeric fraction. (b) NFEVP1, HFEVP1 and MFE were applied at 20 μg/ml to immobilized αvβ6 and control Tris buffered wells. Binding was detected with mouse anti-Tetra-His IgG followed by sheep anti-mouse horseradish peroxidase(HRP)-linked secondary antibody. The data represent the mean of triplicate measurements and error bars represent the standard deviation at each data point. (c) Radiolabelled [$^{51}$Cr]3T3β6.19 cells in various concentrations of MFE, NFEVP1, HFEVP1 or 10D5 were added to 96-well plates coated with 50 μl (0.25 μg/ml) LAP. Data show the mean and standard deviations of quadruplet wells.
Figure 8B:
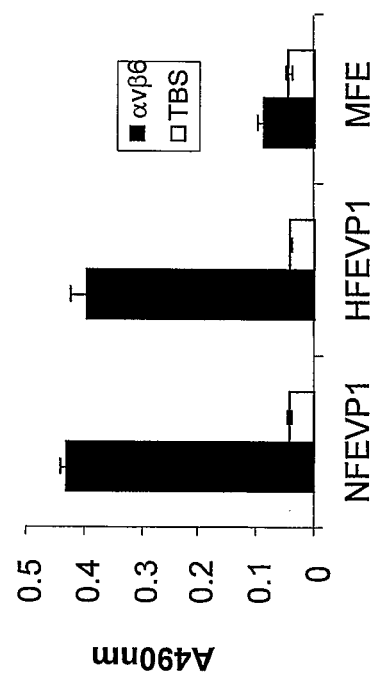
Figure 8C:
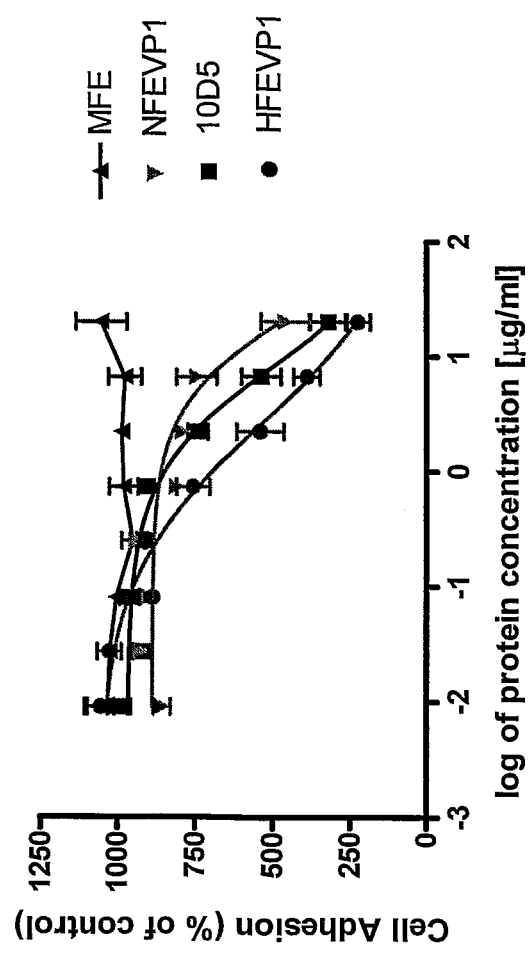

Having established that the murine scFv, MFE, can be used as a scaffold for introduction of the αvβ6-binding peptide, VP1, the same strategy was applied but using the previously described stabilized humanized MFE (HFE) (27) as a scaffold. The protein expressing vector was obtained by overlapping PCR identical to the murine analogue with the Y100b to P100b mutation in the heavy chain that eliminated CEA binding. Stabilized humanized NFEVP1 (HFEVP1) was expressed at 115 mg/L by *P. Pastoris*, determined after initial EDB-IMAC chromatography. The protein formed almost exclusively a dimer as revealed by size-exclusion chromatography (FIG. 8(*a*)). Fractions, containing dimer were separated and used for subsequent experiments. HFEVP1 bound to immobilized αvβ6 in ELISA when probed with anti-His followed by anti-mouse labelled HRP IgG (FIG. 8(*b*). HFEVP1 also inhibited the adhesion of αvβ6-expressing 3T3β6.19 cells towards LAP (FIG. 8(*c*)). HFEVP1 was the most potent inhibitor tested in the assay. IC50 values determined from the assay were 21.97 µg/ml (7640) for NFEVP1, 8.42 µg/ml (56.1 µM for 10D5 and 2.55 µg/ml (45.14 µM) for HFEVP1.

Discussion

Whole antibodies with specificity for their target have been classically obtained by hybridoma screening technology after immunization with the antigen (30). A further well established approach that selects for scFvs is phage display technology where repertoires of scFvs are displayed on the surface of filamentous bacteriophage and screened for binding to antigen (31). In addition, antibodies with binding specificities for their targets can be generated by a rational structure based approach, grafting of a target-binding sequence from a ligand into the CDR region of the antibody.

Here we describe the generation of the scFv, MFEVP1, with αvβ6binding specificity by a rational structure based approach by insertion of the binding region of the viral coat protein, VP1, of Foot-and-mouth disease virus (FMDV), serotype O, into the CDR3 loop region of the VH domain of MFE. Previous structural data of VP1 have identified the integrin-binding RGD motif on the tip of the GH loop (32; 33). A further motif, DLXXL (SEQ ID NO: 47), was identified by displaying peptide libraries on phage as crucial for αvβ6 binding (12). In VP1 this motif includes the D residue of the RGD sequence and the two L residues are arranged in a DLXXL (SEQ ID NO: 47) motif.

The resulting scFv loop variant, named MFEVP1, was expressed in *E. coli* and secreted into the media at comparable levels to the parent MFE. Purification was via the His-tag followed by size-exclusion chromatography to obtain the monomeric form.

We showed by ELISA that the monomeric scFv bound to immobilized αvβ6 and by Flow cytometry when expressed on cells. In agreement with integrin-ligand interactions the binding was metal dependent and was abolished in the presence of EDTA. Furthermore, MFEVP1 inhibited the migration of αvβ6-expressing cells towards its ligand, LAP-1.

MFEVP1 was specific for the integrin αvβ6 and did not show binding at detectable levels to immobilized αvβ3 in ELISA and to αvβ3, αvβ8, αvβ5 and α5β1 expressed on cells.

Insertion of the binding region of VP1 of FMDV of O type strain into MFE was predicted to be a promising strategy in order to develop a scFv with specificity for αvβ6 because previous studies have shown that in β6-transfected cells αvβ6 functions as the major receptor for virus attachment, whereas other epithelial expressed integrins, namely α5β1 or αvβ5, appear not to have a role (34).

MFEVP1 had the desired specificity for αvβ6, as well as residual binding to the parent target, CEA. This binding could be eliminated when the VH residues $Y_{100b}$ was mutated to $P_{100b}$, thus generating NFEVP1. Previous work has shown that binding of MFE to CEA was abolished when this mutation was introduced in MFE (19). MFE-CEA interactions were predicted from the way a MFE molecule interacts with another MFE molecule in the X-ray structure and this highlighted the importance of $Y_{100b}$ (26). This was further elaborated by a subsequent modelling study of the interaction of MFE with CEA (35).

The αvβ6-binding peptide did not affect the structure of the scFv and maintained a similar midpoint of denaturation when compared to MFE, NFEVP1, 45° C., MFE, 47° C., as determined by FT-IR spectroscopy.

A link between αvβ6 expression and carcinoma progression has been suggested due to its ability to modulate invasion, inhibit apoptosis, regulate protease expression and activate TGF-β1 (36). αvβ6 has also been highlighted as a promising cancer target due to its de novo expression on various cancerous tissues (36). A 12-mer αvβ6-binding peptide has shown promise in mediating T cell killing of αvβ6 expressing ovarian tumour targets when fused to human IgG4 hinge-Fc extracellular domain and to the cytoplasmic tail of CD3-ξ(37).

Although scFvs might not be in itself good targeting agents due to their rapid blood clearance they will allow genetic fusion to toxins, increasing the size and slower blood clearance, in particular when the toxin forms dimeric or multimeric arrangements, which will introduce avidity. Delivery of scFv-toxin fusion's would benefit from their ability to internalize. NFEVP1 was able to internalize in αvβ6-expressing A375Pβ6cells. scFvs can also be multimerically attached to drug carrying vehicles, such as liposomes and polymers. scFvs can be converted into whole antibodies for dimeric presentation, exploiting the intrinsic toxic functions, antibody-dependent cellular cytotoxicity (ADCC) and complement-dependent cytotoxicity (CDC). A construct which provides good tumour penetration, high target retention, due to its dimeric binding, and rapid blood clearance is the diabody (38). The diabody is double the size of the scFv and considerable smaller than a whole antibody. It is generated by shortening the scFv (Gly$_4$Ser)$_3$ VH-VL linker to a Gly$_4$Ser linker, which forces the VH and VL domains from different chains to pair (39).

A major problem in cancer therapy is immunogenicity of the antibody therapeutic in particular in repeated treatment. NFEVP1 is of murine origin and is likely to result in immunogenetic reactions in humans. Hence previous studies have addressed this problem by converting MFE into a humanized version. (27) Comparison of the x-ray structure of MFE with a human analogue allowed identification of 28 surface residues for humanization of MFE. (25) These residues when introduced into MFE combined with three additional mutations for stabilization identified by yeast display expression maturation produced stabilized humanized MFE (27). In this study the stabilized humanized MFE was used as a scaffold to insert the VP1 peptide and combined with the Y100b to P100b mutation gave HFEVP1. The protein was expressed almost exclusively as a dimer in *P. Pastoris* as shown by size-exclusion chromatography. HFEVP1 bound to αvβ6 in ELISA and inhibited the adhesion of αvβ6 expressing cells to LAP thus mimicking the behaviour of the murine analogue. HFEVP1 was a slightly better inhibitor than the commercially available whole antibody, 10D5; IC50 value for HFEVP1 was 2.55 µg/ml (45.14 µM) and for 10D5 was 8.42 µg/ml (56.1 µM).

In conclusion, a αvβ6-binding scFv was generated by insertion of the RGD-containing VP1 peptide of FMDV into MFE that had no binding for MFE's target, CEA, when combined with the VHY$_{100b}$ to VHP$_{100b}$ mutation. This study has shown that MFE-23 (including the humanised variants) are good scaffolds for peptide insertion to alter binding specificity of the scFv. The MFE-23 antibody (including the humanised variants) could thus be envisaged to be used to obtain binding to other tumour targeting antigens using a similar approach.

References

All publications, patent and patent applications cited herein or filed with this application, including references filed as part of an Information Disclosure Statement are incorporated by reference in their entirety.

1. Hynes, R. O. (2002) *Cell* 110, 673-687
2. Ruoslahti, E. (1991) *J. Clin. Invest* 87, 1-5
3. Giancotti, F. G. and Mainiero, F. (1994) *Biochim. Biophys. Acta* 1198, 47-64
4. Breuss, J. M., Gallo, J., DeLisser, H. M., Klimanskaya, I. V., Folkesson, H. G., Pittet, J. F., Nishimura, S. L., Aldape, K., Landers, D. V., Carpenter, W., and (1995) *J. Cell Sci.* 108 (Pt 6), 2241-2251
5. Ahmed, N., Pansino, F., Clyde, R., Murthi, P., Quinn, M. A., Rice, G. E., Agrez, M. V., Mok, S., and Baker, M. S. (2002) *Carcinogenesis* 23, 237-244
6. Arihiro, K., Kaneko, M., Fujii, S., Inai, K., and Yokosaki, Y. (2000) *Breast Cancer* 7, 19-26
7. Sipos, B., Hahn, D., Carceller, A., Piulats, J., Hedderich, J., Kalthoff, H., Goodman, S. L., Kosmahl, M. and Kloppel, G. (2004) *Histopathology* 45, 226-236
8. Ramos, D. M., But, M., Regezi, J., Schmidt, B. L., Atakilit, A., Dang, D., Ellis, D., Jordan, R., and Li, X. (2002) *Matrix Biology* 21, 297-307
9. Bates, R. C., Bellovin, D. I., Brown, C., Maynard, E., Wu, B., Kawakatsu, H., Sheppard, D., Oettgen, P., and Mercurio, A. M. (2005) *J. Clin. Invest* 115, 339-347
10. Munger, J. S., Huang, X., Kawakatsu, H., Griffiths, M. J., Dalton, S. L., Wu, J., Pittet, J. F., Kaminski, N., Garat, C., Matthay, M. A., Rifkin, D. B., and Sheppard, D. (1999) *Cell* 96, 319-328
11. Jackson, T., King, A. M., Stuart, D. I., and Fry, E. (2003) *Virus Res.* 91, 33-46
12. Kraft, S., Diefenbach, B., Mehta, R., Jonczyk, A., Luckenbach, G. A., and Goodman, S. L. (1999) *J. Biol. Chem.* 274, 1979-1985
13. Mateu, M. G., Valero, M. L., Andreu, D., and Domingo, E. (1996) *J. Biol. Chem.* 271, 12814-12819
14. Chester, K. A., Begent, R. H., Robson, L., Keep, P., Pedley, R. B., Boden, J. A., Boxer, G., Green, A., Winter, G., Cochet, O., and (1994) *Lancet* 343, 455-456
15. Begent, R. H., Verhaar, M. J., Chester, K. A., Casey, J. L., Green, A. J., Napier, M. P., Hope-Stone, L. D., Cushen, N., Keep, P. A., Johnson, C. J., Hawkins, R. E., Hilson, A. J., and Robson, L. (1996) *Nat. Med.* 2, 979-984
16. Mayer, A., Tsiompanou, E., O'Malley, D., Boxer, G. M., Bhatia, J., Flynn, A. A., Chester, K. A., Davidson, B. R., Lewis, A. A., Winslet, M. C., Dhillon, A. P., Hilson, A. J., and Begent, R. H. (2000) *Clin. Cancer Res.* 6, 1711-1719
17. Chester, K. A., Bhatia, J., Boxer, G., Cooke, S. P., Flynn, A. A., Huhalov, A., Mayer, A., Pedley, R. B., Robson, L., Sharma, S. K., Spencer, D. I., and Begent, R. H. (2000) *Dis. Markers* 16, 53-62
18. Chester, K. A., Mayer, A., Bhatia, J., Robson, L., Spencer, D. I., Cooke, S. P., Flynn, A. A., Sharma, S. K., Boxer, G., Pedley, R. B., and Begent, R. H. (2000) *Cancer Chemother. Pharmacol.* 46 Suppl, S8-12
19. Read, D. A., Chester, K. A., Keep, P. A., Begent, R. H. J., Pedersen, J. T., and Rees, A. R. (1995) *Br. J. Cancer* 71,
20. Lanza, P., Felding-Habermann, B., Ruggeri, Z. M., Zanetti, M., and Billetta, R. (1997) *Blood Cells Mol. Dis.* 23, 230-241
21. Lanza, P., Billetta, R., Antonenko, S., and Zanetti, M. (1993) *Proc. Natl. Acad. Sci. U.S.A* 90, 11683-11687
22. McLane, K. E., Burton, D. R., and Ghazal, P. (1995) *Proc. Natl. Acad. Sci. U.S.A* 92, 5214-5218
23. Moroncini, G., Kanu, N., Solforosi, L., Abalos, G., Telling, G. C., Head, M., Ironside, J., Brockes, J. P., Burton, D. R., and Williamson, R. A. (2004) *Proc. Natl. Acad. Sci. U.S.A* 101, 10404-10409
24. Burman, A., Clark, S., Abrescia, N. G., Fry, E. E., Stuart, D. I., and Jackson, T. (2006) *J. Virol.* 80, 9798-9810
25. Dicara, D., Rapisarda, C., Sutclifffe, J. L., Violette, S. M., Weinreb, P. H., Hart, I. R., Howard, M. J., and Marshall, J. F. (2007) *J. Biol. Chem.*
26. Boehm, M. K., Corper, A. L., Wan, T., Sohi, M. K., Sutton, B. J., Thornton, J. D., Keep, P. A., Chester, K. A., Begent, R. H., and Perkins, S. J. (2000) *Biochem. J.* 346 Pt 2, 519-528
27. Thomas, G. J., Lewis, M. P., Whawell, S. A., Russell, A., Sheppard, D., Hart, I. R., Speight, P. M., and Marshall, J. F. (2001) *J. Invest Dermatol.* 117, 67-73
28. Lee, Y. C., Boehm, M. K., Chester, K. A., Begent, R. H., and Perkins, S. J. (2002) *J. Mol. Biol.* 320, 107-127
29. Tolner, B., Smith, L., Begent, R. H. J., and Chester, K. A. (2006) Nat. Protocols in press,
30. Kohler, G. and Milstein, C. (1975) *Nature* 256, 495-497
31. Winter, G., Griffiths, A. D., Hawkins, R. E., and Hoogenboom, H. R. (1994) *Annu. Rev. Immunol.* 12, 433-455
32. Acharya, R., Fry, E., Stuart, D., Fox, G., Rowlands, D., and Brown, F. (1989) *Nature* 337, 709-716
33. Logan, D., Abu-Ghazaleh, R., Blakemore, W., Curry, S., Jackson, T., King, A., Lea, S., Lewis, R., Newman, J., Parry, N., and (1993) Nature 362, 566-568

34. Jackson, T., Sheppard, D., Denyer, M., Blakemore, W., and King, A. M. (2000) *J Virol.* 74, 4949-4956
35. Boehm, M. K. and Perkins, S. J. (2000) *FEES Lett.* 475, 11-16
36. Thomas, G. J., Nystrom, M. L., and Marshall, J. F. (2006) *J. Oral Pathol. Med.* 35, 1-10
37. Pameijer, C. R., Navanjo, A., Meechoovet, B., Wagner, J. R., Aguilar, B., Wright, C. L., Chang, W. C., Brown, C. E., and Jensen, M. C. (2007) *Cancer Gene Ther.* 14, 91-97
38. Holliger, P. and Hudson, P. J. (2005) *Nat. Biotechnol.* 23, 1126-1136
39. Holliger, P., Prospero, T., and Winter, G. (1993) *Proc. Natl. Acad. Sci. U.S.A* 90, 6444-6448
40. FitzGerald, K., Holliger, P., and Winter, G. (1997) *Protein Eng* 10, 1221-1225
41. Graff, C. P., Chester, K., Begent, R., and Wittrup, K. D. (2004) *Protein Eng Des Sel* 17, 293-304

Chester K A, Baker M and Mayer A (2005) Overcoming the immunological response to foreign enzymes in cancer therapy *Expert Rev. Clin. Immunol.* 1: 549-559

Hoogenboom, (2005). Selecting and screening recombinant antibody libraries. Nat Biotechnology, 23, 1105-1116

Hofmeister V, Schrama D, Becker J C, Anti-cancer therapies targeting the tumor stroma, Cancer Immunol Immunother. 2007 Jul. 27; in press Li Y, Cozzi P J, Targeting uPA/uPAR in prostate cancer. Cancer Treat Rev. 2007, 33(6):521-7.

Muñoz R, Arias Y, Ferreras J M, Rojo M A, Gayoso M J, Nocito M, Benitez J, Jiménez P, Bernabéu C, Girbés T., Targeting a marker of the tumour neovasculature using a novel anti-human CD105-immunotoxin containing the non-toxic type 2 ribosome-inactivating protein nigrin b. Cancer Lett. 2007 Oct. 18; 256(1):73-80.

Baccala A, Sercia L, Li J, Heston W, Zhou M. Expression of prostate-specific membrane antigen in tumor-associated neovasculature of renal neoplasms. Urology. 2007 August; 70(2):385-90.

Bühler P, Wolf P, Gierschner D, Schaber I, Katzenwadel A, Schultze-Seemann W, Wetterauer U, Tacke M, Swamy M, Schamel W W, Elsässer-Beile U. A bispecific diabody directed against prostate-specific membrane antigen and CD3 induces T-cell mediated lysis of prostate cancer cells. Cancer Immunol Immunother. 2007 Jun 20; in press Johnston J B, Navaratnam S, Pitz M W, Maniate J M, Wiechec E, Baust H, Gingerich J, Skliris G P, Murphy L C, Los M. Targeting the EGFR Pathway for cancer therapy. Curr Med Chem. 2006, 13:3483-3492.

---

The invention claimed is:

1. An anti-αvβ6 integrin antibody obtained by inserting the amino acid sequence consisting of AVPNLRGDLQV-LAQKVA (SEQ ID NO: 19) between adjacent amino acid residues Thr98 and Gly99 (in Kabat numbering) of CDR H3 of a parent antibody, wherein the parent antibody comprises the following complementarity determining regions (CDRs):
   (a) Heavy Chain CDR 1: Asp Ser Tyr Met His (SEQ ID NO: 53); and
   (b) Heavy Chain CDR 2: Trp Ile Asp Pro Glu Asn Gly Asp Thr Glu Tyr Ala Pro Lys Phe Gln Gly (SEQ ID NO: 54); and
   (c) Heavy Chain CDR 3: (i) Gly Thr Pro Thr Gly Pro Tyr Tyr Phe Asp Tyr (SEQ ID NO: 55), or (ii) Gly Thr Pro Thr Gly Pro Tyr Pro Phe Asp Tyr (SEQ ID NO: 56); and
   (d) Light Chain CDR 1: (i) Ser Ala Ser Ser Ser Val Pro Tyr Met His (SEQ ID NO: 57), or (ii) Ser Ala Ser Ser Ser Val Ser Tyr Met His (SEQ ID NO: 58); and
   (e) Light Chain CDR 2: (i) Ser Thr Ser Asn Leu Ala Ser (SEQ ID NO: 59), or (ii) Leu Thr Ser Asn Leu Ala Ser (SEQ ID NO: 60); and
   (f) Light Chain CDR 3: Gln Gln Arg Ser Ser Tyr Pro Leu Thr (SEQ ID NO: 61).

2. The anti-αvβ6 integrin antibody of claim 1, wherein the antibody is humanised.

3. The anti-αvβ6 integrin antibody of claim 1, wherein the antibody is a scFv or a diabody.

4. The anti-αvβ6 integrin antibody of claim 3, wherein the scFv or diabody comprises a linker having the sequence $(Gly_4Ser)_n$, wherein n is between 1 and 4 SEQ ID NOs: 26-29, respectively.

5. The anti-αvβ6 integrin antibody of claim 1, wherein the parent antibody comprises the mutations G44C in the heavy chain and/or A100C in the light chain (using Kabat nomenclature).

6. The anti-αvβ6 integrin antibody of claim 1, wherein the antibody is conjugated to a therapeutically active moiety.

7. A nucleic acid molecule that encodes an anti-αvβ6 integrin antibody of claim 1.

8. An expression vector comprising a nucleic acid molecule of claim 7, operably linked to control sequences to direct its expression.

9. An isolated host cell comprising the expression vector of claim 8.

10. The anti-αvβ6 integrin antibody of claim 1, wherein the parent antibody
comprises the amino acid sequence of residues 1 to 244 of SEQ ID NO: 2 .

11. The anti-αvβ6 integrin antibody of claim 1, wherein the antibody is conjugated to a detectable moiety.

12. The anti-αvβ6 integrin antibody of claim 1, wherein the antibody is directly or indirectly conjugated or linked to one or more of a cytotoxic moiety, an agent capable of converting a prodrug to a cytotoxic moiety, and/or a radioactive atom.

13. A method of modifying a parent antibody to an antibody capable of binding to αvβ6 integrin, wherein the parent antibody comprises the following complementarity determining regions (CDRs):
   (a) Heavy Chain CDR 1: Asp Ser Tyr Met His (SEQ ID NO: 53); and
   (b) Heavy Chain CDR 2: Trp Ile Asp Pro Glu Asn Gly Asp Thr Glu Tyr Ala Pro Lys Phe Gln Gly (SEQ ID NO: 54); and
   (c) Heavy Chain CDR 3: Gly Thr Pro Thr Gly Pro Tyr Tyr Phe Asp Tyr (SEQ ID NO: 55), or (ii) Gly Thr Pro Thr Gly Pro Tyr Pro Phe Asp Tyr (SEQ ID NO: 56); and
   (d) Light Chain CDR 1: (i) Ser Ala Ser Ser Ser Val Pro Tyr Met His (SEQ ID NO: 57), or (ii) Ser Ala Ser Ser Ser Val Ser Tyr Met His (SEQ ID NO: 58); and
   (e) Light Chain CDR 2: (i) Ser Thr Ser Asn Leu Ala Ser (SEQ ID NO: 59), or (ii) Leu Thr Ser Asn Leu Ala Ser (SEQ ID NO: 60); and
   (f) Light Chain CDR 3: Gln Gln Arg Ser Ser Tyr Pro Leu Thr (SEQ ID NO: 61); and the method comprises inserting the amino acid sequence consisting of AVPNLRGDLQVLAQKVA (SEQ ID NO: 19) between adjacent amino acid residues Thr98 and Gly99 (in Kabat numbering) of CDR H3 of the parent antibody.

14. The method of claim 13, further comprising humanizing the antibody that binds αvβ6 or the parent antibody.

15. A method of treating an αvβ6-mediated disease or a disease in which cells overexpress αvβ6, said disease being selected from the group consisting of: cancer, and chronic obstructive pulmonary disease (COPD), the method comprising administering to a patient in need thereof a therapeutically effective amount of an antibody that binds αvβ6 integrin according to claim 1.

16. The method of claim 15, wherein said disease is an epithelial cancer.

* * * * *

SEQUENCE LISTING

```
<160> NUMBER OF SEQ ID NOS: 61

<210> SEQ ID NO 1
<211> LENGTH: 761
<212> TYPE: DNA
<213> ORGANISM: Artificial sequence
<220> FEATURE:
<223> OTHER INFORMATION: Synthetic sequence: MFE-23 Cloned into pUC119
      and expressed in E. coli
<220> FEATURE:
<221> NAME/KEY: CDS
<222> LOCATION: (9)..(746)

<400> SEQUENCE: 1 ccatggcc cag gtg aaa ctg cag cag tct ggg gca gaa ctt gtg agg tca      50
         Gln Val Lys Leu Gln Gln Ser Gly Ala Glu Leu Val Arg Ser
           1               5                  10 ggg acc tca gtc aag ttg tcc tgc aca gct tct ggc ttc aac att aaa      98
Gly Thr Ser Val Lys Leu Ser Cys Thr Ala Ser Gly Phe Asn Ile Lys
 15                  20                  25                  30 gac tcc tat atg cac tgg ttg agg cag ggg cct gaa cag ggc ctg gag     146
Asp Ser Tyr Met His Trp Leu Arg Gln Gly Pro Glu Gln Gly Leu Glu
                 35                  40                  45 tgg att gga tgg att gat cct gag aat ggt gat act gaa tat gcc ccg     194
Trp Ile Gly Trp Ile Asp Pro Glu Asn Gly Asp Thr Glu Tyr Ala Pro
             50                  55                  60 aag ttc cag ggc aag gcc act ttt act aca gac aca tcc tcc aac aca     242
Lys Phe Gln Gly Lys Ala Thr Phe Thr Thr Asp Thr Ser Ser Asn Thr
 65                  70                  75 gcc tac ctg cag ctc agc agc ctg aca tct gag gac act gcc gtc tat     290
Ala Tyr Leu Gln Leu Ser Ser Leu Thr Ser Glu Asp Thr Ala Val Tyr
     80                  85                  90 tat tgt aat gag ggg act ccg act ggg ccg tac tac ttt gac tac tgg     338
Tyr Cys Asn Glu Gly Thr Pro Thr Gly Pro Tyr Tyr Phe Asp Tyr Trp
 95                 100                 105                 110 ggc caa ggg acc acg gtc acc gtc tcc tca ggt gga ggc ggt tca ggc     386
Gly Gln Gly Thr Thr Val Thr Val Ser Ser Gly Gly Gly Gly Ser Gly
                115                 120                 125
```

| | | | | | | | | | | | | | | |
|---|---|---|---|---|---|---|---|---|---|---|---|---|---|---|
| gga | ggt | ggc | tct | ggc | ggt | ggc | gga | tca | gaa | aat | gtg | ctc | acc | cag | tct | 434 |
| Gly | Gly | Gly | Ser | Gly | Gly | Gly | Gly | Ser | Glu | Asn | Val | Leu | Thr | Gln | Ser | |
| | | | 130 | | | | | 135 | | | | 140 | | | | |

```
gga ggt ggc tct ggc ggt ggc gga tca gaa aat gtg ctc acc cag tct    434
Gly Gly Gly Ser Gly Gly Gly Gly Ser Glu Asn Val Leu Thr Gln Ser
            130             135                 140 cca gca atc atg tct gca tct cca ggg gag aag gtc acc ata acc tgc    482
Pro Ala Ile Met Ser Ala Ser Pro Gly Glu Lys Val Thr Ile Thr Cys
        145             150                 155 agt gcc agc tca agt gta agt tac atg cac tgg ttc cag cag aag cca    530
Ser Ala Ser Ser Ser Val Ser Tyr Met His Trp Phe Gln Gln Lys Pro
    160             165                 170 ggc act tct ccc aaa ctc tgg att tat agc aca tcc aac ctg gct tct    578
Gly Thr Ser Pro Lys Leu Trp Ile Tyr Ser Thr Ser Asn Leu Ala Ser
175             180                 185                 190 gga gtc cct gct cgc ttc agt ggc agt gga tct ggg acc tct tac tct    626
Gly Val Pro Ala Arg Phe Ser Gly Ser Gly Ser Gly Thr Ser Tyr Ser
                195                 200                 205 ctc aca atc agc cga atg gag gct gaa gat gct gcc act tat tac tgc    674
Leu Thr Ile Ser Arg Met Glu Ala Glu Asp Ala Ala Thr Tyr Tyr Cys
            210                 215                 220 cag caa agg agt agt tac cca ctc acg ttc ggt gct ggc acc aag ctg    722
Gln Gln Arg Ser Ser Tyr Pro Leu Thr Phe Gly Ala Gly Thr Lys Leu
        225                 230                 235 gag ctg aaa cgg gcg gcc gca cat caccatcatc accat                   761
Glu Leu Lys Arg Ala Ala Ala His
    240                 245
```

<210> SEQ ID NO 2
<211> LENGTH: 246
<212> TYPE: PRT
<213> ORGANISM: Artificial sequence
<220> FEATURE:
<223> OTHER INFORMATION: Synthetic Construct

<400> SEQUENCE: 2

```
Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Asn Val Leu Thr Gln Ser Pro Ala
    130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Leu Trp Ile Tyr Ser Thr Ser Asn Leu Ala Ser Gly Val
            180                 185                 190
```

-continued

```
Pro Ala Arg Phe Ser Gly Ser Gly Ser Gly Thr Ser Tyr Ser Leu Thr
        195                 200                 205

Ile Ser Arg Met Glu Ala Glu Asp Ala Ala Thr Tyr Tyr Cys Gln Gln
    210                 215                 220

Arg Ser Ser Tyr Pro Leu Thr Phe Gly Ala Gly Thr Lys Leu Glu Leu
225                 230                 235                 240

Lys Arg Ala Ala Ala His
                245
```

<210> SEQ ID NO 3
<211> LENGTH: 21
<212> TYPE: DNA
<213> ORGANISM: Artificial sequence
<220> FEATURE:
<223> OTHER INFORMATION: Synthetic sequence: MFE-23 Cloned into pUC119
      and expressed in E. coli

<400> SEQUENCE: 3
atggtgatga tggtgatgtg c                                            21

<210> SEQ ID NO 4
<211> LENGTH: 812
<212> TYPE: DNA
<213> ORGANISM: Artificial sequence
<220> FEATURE:
<223> OTHER INFORMATION: Synthetic sequence: MFEVP1 Cloned into pUC119
      Expressed in E. coli
<220> FEATURE:
<221> NAME/KEY: CDS
<222> LOCATION: (9)..(797)

<400> SEQUENCE: 4

```
ccatggcc cag gtg aaa ctg cag cag tct ggg gca gaa ctt gtg agg tca        50
         Gln Val Lys Leu Gln Gln Ser Gly Ala Glu Leu Val Arg Ser
          1               5                  10 ggg acc tca gtc aag ttg tcc tgc aca gct tct ggc ttc aac att aaa        98
Gly Thr Ser Val Lys Leu Ser Cys Thr Ala Ser Gly Phe Asn Ile Lys
 15                  20                  25                  30 gac tcc tat atg cac tgg ttg agg cag ggg cct gaa cag ggc ctg gag      146
Asp Ser Tyr Met His Trp Leu Arg Gln Gly Pro Glu Gln Gly Leu Glu
                 35                  40                  45 tgg att gga tgg att gat cct gag aat ggt gat act gaa tat gcc ccg      194
Trp Ile Gly Trp Ile Asp Pro Glu Asn Gly Asp Thr Glu Tyr Ala Pro
         50                  55                  60 aag ttc cag ggc aag gcc act ttt act aca gac aca tcc tcc aac aca      242
Lys Phe Gln Gly Lys Ala Thr Phe Thr Thr Asp Thr Ser Ser Asn Thr
 65                  70                  75 gcc tac ctg cag ctc agc agc ctg aca tct gag gac act gcc gtc tat      290
Ala Tyr Leu Gln Leu Ser Ser Leu Thr Ser Glu Asp Thr Ala Val Tyr
             80                  85                  90 tat tgt aat gag ggg act ccg act gca gtt ccg aat ctg cga ggt gat      338
Tyr Cys Asn Glu Gly Thr Pro Thr Ala Val Pro Asn Leu Arg Gly Asp
 95                 100                 105                 110 ctg cag gtg ctg gcg cag aaa gtt gca ggg ccg tac tac ttt gac tac      386
Leu Gln Val Leu Ala Gln Lys Val Ala Gly Pro Tyr Tyr Phe Asp Tyr
                115                 120                 125 tgg ggc caa ggg acc acg gtc acc gtc tcc tca ggt gga ggc ggt tca      434
Trp Gly Gln Gly Thr Thr Val Thr Val Ser Ser Gly Gly Gly Gly Ser
            130                 135                 140 ggc gga ggt ggc tct ggc ggt ggc gga tca gaa aat gtg ctc acc cag      482
Gly Gly Gly Gly Ser Gly Gly Gly Gly Ser Glu Asn Val Leu Thr Gln
                145                 150                 155
```

```
tct cca gca atc atg tct gca tct cca ggg gag aag gtc acc ata acc        530
Ser Pro Ala Ile Met Ser Ala Ser Pro Gly Glu Lys Val Thr Ile Thr
    160             165                 170 tgc agt gcc agc tca agt gta agt tac atg cac tgg ttc cag cag aag        578
Cys Ser Ala Ser Ser Ser Val Ser Tyr Met His Trp Phe Gln Gln Lys
175             180                 185                 190 cca ggc act tct ccc aaa ctc tgg att tat agc aca tcc aac ctg gct        626
Pro Gly Thr Ser Pro Lys Leu Trp Ile Tyr Ser Thr Ser Asn Leu Ala
                195                 200                 205 tct gga gtc cct gct cgc ttc agt ggc agt gga tct ggg acc tct tac        674
Ser Gly Val Pro Ala Arg Phe Ser Gly Ser Gly Ser Gly Thr Ser Tyr
            210                 215                 220 tct ctc aca atc agc cga atg gag gct gaa gat gct gcc act tat tac        722
Ser Leu Thr Ile Ser Arg Met Glu Ala Glu Asp Ala Ala Thr Tyr Tyr
        225                 230                 235 tgc cag caa agg agt agt tac cca ctc acg ttc ggt gct ggc acc aag        770
Cys Gln Gln Arg Ser Ser Tyr Pro Leu Thr Phe Gly Ala Gly Thr Lys
    240                 245                 250 ctg gag ctg aaa cgg gcg gcc gca cat caccatcatc accat                   812
Leu Glu Leu Lys Arg Ala Ala Ala His
255                 260

<210> SEQ ID NO 5
<211> LENGTH: 263
<212> TYPE: PRT
<213> ORGANISM: Artificial sequence
<220> FEATURE:
<223> OTHER INFORMATION: Synthetic Construct

<400> SEQUENCE: 5

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Ala Val Pro Asn Leu Arg Gly Asp Leu Gln
            100                 105                 110

Val Leu Ala Gln Lys Val Ala Gly Pro Tyr Tyr Phe Asp Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Gly Ser Glu Asn Val Leu Thr Gln Ser Pro
145                 150                 155                 160

Ala Ile Met Ser Ala Ser Pro Gly Glu Lys Val Thr Ile Thr Cys Ser
                165                 170                 175

Ala Ser Ser Ser Val Ser Tyr Met His Trp Phe Gln Gln Lys Pro Gly
            180                 185                 190

Thr Ser Pro Lys Leu Trp Ile Tyr Ser Thr Ser Asn Leu Ala Ser Gly
        195                 200                 205

Val Pro Ala Arg Phe Ser Gly Ser Gly Ser Gly Thr Ser Tyr Ser Leu
    210                 215                 220
```

```
Thr Ile Ser Arg Met Glu Ala Glu Asp Ala Ala Thr Tyr Tyr Cys Gln
225                 230                 235                 240

Gln Arg Ser Ser Tyr Pro Leu Thr Phe Gly Ala Gly Thr Lys Leu Glu
                245                 250                 255

Leu Lys Arg Ala Ala Ala His
            260

<210> SEQ ID NO 6
<211> LENGTH: 144
<212> TYPE: DNA
<213> ORGANISM: Artificial sequence
<220> FEATURE:
<223> OTHER INFORMATION: Synthetic sequence: MFEVP1 Cloned into pUC119
      and expressed in E. coli

<400> SEQUENCE: 6
tggagatgca gacatgattg ctggagactg ggtgagcaca ttttctgatc cgccaccgcc      60
agagccacct ccgcctgaac cgcctccacc tgaggagacg gtgaccgtgg tcccttggcc     120
ccagtagtca aacgggtacg gccc                                            144

<210> SEQ ID NO 7
<211> LENGTH: 111
<212> TYPE: DNA
<213> ORGANISM: Artificial sequence
<220> FEATURE:
<223> OTHER INFORMATION: Synthetic sequence: MFEVP1 Cloned into pUC119
      and expressed in E. coli

<400> SEQUENCE: 7
atggtgatga tggtgatgtg cggccgcccg tttcagctcc agcttggtgc cagcaccgaa      60
cgtgagtggg taactactcc tttgctggca gtaataagtg cagcatctt c              111

<210> SEQ ID NO 8
<211> LENGTH: 812
<212> TYPE: DNA
<213> ORGANISM: Artificial sequence
<220> FEATURE:
<223> OTHER INFORMATION: Synthetic sequence: NFEVP1: Cloned in Puc119,
      expressed in E. coli and clone in Modified pPICZalphaB expressed
      in P. pastoris
<220> FEATURE:
<221> NAME/KEY: CDS
<222> LOCATION: (9)..(797)

<400> SEQUENCE: 8 ccatggcc cag gtg aaa ctg cag cag tct ggg gca gaa ctt gtg agg tca       50
         Gln Val Lys Leu Gln Gln Ser Gly Ala Glu Leu Val Arg Ser
           1               5                  10 ggg acc tca gtc aag ttg tcc tgc aca gct tct ggc ttc aac att aaa       98
Gly Thr Ser Val Lys Leu Ser Cys Thr Ala Ser Gly Phe Asn Ile Lys
 15                  20                  25                  30 gac tcc tat atg cac tgg ttg agg cag ggg cct gaa cag ggc ctg gag      146
Asp Ser Tyr Met His Trp Leu Arg Gln Gly Pro Glu Gln Gly Leu Glu
                 35                  40                  45 tgg att gga tgg att gat cct gag aat ggt gat act gaa tat gcc ccg      194
Trp Ile Gly Trp Ile Asp Pro Glu Asn Gly Asp Thr Glu Tyr Ala Pro
             50                  55                  60 aag ttc cag ggc aag gcc act ttt act aca gac aca tcc tcc aac aca      242
Lys Phe Gln Gly Lys Ala Thr Phe Thr Thr Asp Thr Ser Ser Asn Thr
         65                  70                  75 gcc tac ctg cag ctc agc agc ctg aca tct gag gac act gcc gtc tat      290
Ala Tyr Leu Gln Leu Ser Ser Leu Thr Ser Glu Asp Thr Ala Val Tyr
     80                  85                  90
```

```
tat tgt aat gag ggg act ccg act gca gtt ccg aat ctg cga ggt gat         338
Tyr Cys Asn Glu Gly Thr Pro Thr Ala Val Pro Asn Leu Arg Gly Asp
 95             100                 105                 110 ctg cag gtg ctg gcg cag aaa gtt gca ggg ccg tac ccg ttt gac tac         386
Leu Gln Val Leu Ala Gln Lys Val Ala Gly Pro Tyr Pro Phe Asp Tyr
                115                 120                 125 tgg ggc caa ggg acc acg gtc acc gtc tcc tca ggt gga ggc ggt tca         434
Trp Gly Gln Gly Thr Thr Val Thr Val Ser Ser Gly Gly Gly Gly Ser
            130                 135                 140 ggc gga ggt ggc tct ggc ggt ggc gga tca gaa aat gtg ctc acc cag         482
Gly Gly Gly Gly Ser Gly Gly Gly Gly Ser Glu Asn Val Leu Thr Gln
        145                 150                 155 tct cca gca atc atg tct gca tct cca ggg gag aag gtc acc ata acc         530
Ser Pro Ala Ile Met Ser Ala Ser Pro Gly Glu Lys Val Thr Ile Thr
    160                 165                 170 tgc agt gcc agc tca agt gta agt tac atg cac tgg ttc cag cag aag         578
Cys Ser Ala Ser Ser Ser Val Ser Tyr Met His Trp Phe Gln Gln Lys
175                 180                 185                 190 cca ggc act tct ccc aaa ctc tgg att tat agc aca tcc aac ctg gct         626
Pro Gly Thr Ser Pro Lys Leu Trp Ile Tyr Ser Thr Ser Asn Leu Ala
                195                 200                 205 tct gga gtc cct gct cgc ttc agt ggc agt gga tct ggg acc tct tac         674
Ser Gly Val Pro Ala Arg Phe Ser Gly Ser Gly Ser Gly Thr Ser Tyr
            210                 215                 220 tct ctc aca atc agc cga atg gag gct gaa gat gct gcc act tat tac         722
Ser Leu Thr Ile Ser Arg Met Glu Ala Glu Asp Ala Ala Thr Tyr Tyr
        225                 230                 235 tgc cag caa agg agt agt tac cca ctc acg ttc ggt gct ggg acc aag         770
Cys Gln Gln Arg Ser Ser Tyr Pro Leu Thr Phe Gly Ala Gly Thr Lys
    240                 245                 250 ctg gag ctg aaa cgg gcg gcc gca cat caccatcatc accat                    812
Leu Glu Leu Lys Arg Ala Ala Ala His
255                 260

<210> SEQ ID NO 9
<211> LENGTH: 263
<212> TYPE: PRT
<213> ORGANISM: Artificial sequence
<220> FEATURE:
<223> OTHER INFORMATION: Synthetic Construct

<400> SEQUENCE: 9

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Ala Val Pro Asn Leu Arg Gly Asp Leu Gln
            100                 105                 110

Val Leu Ala Gln Lys Val Ala Gly Pro Tyr Pro Phe Asp Tyr Trp Gly
        115                 120                 125
```

```
Gln Gly Thr Thr Val Thr Val Ser Ser Gly Gly Gly Ser Gly Gly
        130                 135                 140

Gly Gly Ser Gly Gly Gly Ser Glu Asn Val Leu Thr Gln Ser Pro
145                 150                 155                 160

Ala Ile Met Ser Ala Ser Pro Gly Glu Lys Val Thr Ile Thr Cys Ser
            165                 170                 175

Ala Ser Ser Ser Val Ser Tyr Met His Trp Phe Gln Lys Pro Gly
            180                 185                 190

Thr Ser Pro Lys Leu Trp Ile Tyr Ser Thr Ser Asn Leu Ala Ser Gly
        195                 200                 205

Val Pro Ala Arg Phe Ser Gly Ser Gly Ser Gly Thr Ser Tyr Ser Leu
    210                 215                 220

Thr Ile Ser Arg Met Glu Ala Glu Asp Ala Ala Thr Tyr Tyr Cys Gln
225                 230                 235                 240

Gln Arg Ser Ser Tyr Pro Leu Thr Phe Gly Ala Gly Thr Lys Leu Glu
                245                 250                 255

Leu Lys Arg Ala Ala Ala His
            260
```

```
<210> SEQ ID NO 10
<211> LENGTH: 144
<212> TYPE: DNA
<213> ORGANISM: Artificial sequence
<220> FEATURE:
<223> OTHER INFORMATION: Synthetic sequence: NFEVP1: Cloned in Puc119,
      expressed in E. coli and clone in Modified pPICZalphaB expressed
      in P. pastoris

<400> SEQUENCE: 10
tggagatgca gacatgattg ctggagactg ggtgagcaca ttttctgatc cgccaccgcc      60
agagccacct ccgcctgaac cgcctccacc tgaggagacg gtgaccgtgg tcccttggcc     120
ccagtagtca aacgggtacg gccc                                           144

<210> SEQ ID NO 11
<211> LENGTH: 111
<212> TYPE: DNA
<213> ORGANISM: Artificial sequence
<220> FEATURE:
<223> OTHER INFORMATION: Synthetic sequence: NFEVP1: Cloned in Puc119,
      expressed in E. coli and clone in Modified pPICZalphaB expressed
      in P. pastoris

<400> SEQUENCE: 11
atggtgatga tggtgatgtg cggccgcccg tttcagctcc agcttggtgc cagcaccgaa      60
cgtgagtggg taactactcc tttgctggca gtaataagtg gcagcatctt c              111

<210> SEQ ID NO 12
<211> LENGTH: 764
<212> TYPE: DNA
<213> ORGANISM: Artificial sequence
<220> FEATURE:
<223> OTHER INFORMATION: Synthetic sequence: shMFE-23 Cys Cloned into
      modified pPICZalphaB
      Expressed in P. pastoris
<220> FEATURE:
<221> NAME/KEY: CDS
<222> LOCATION: (9)..(764)

<400> SEQUENCE: 12 ccatggcc caa gtt aaa ctg gaa cag tcc ggt gct gaa gtt gtc aaa cca       50
         Gln Val Lys Leu Glu Gln Ser Gly Ala Glu Val Val Lys Pro
           1               5                  10
```

```
ggt gct tcc gtg aag ttg tcc tgt aaa gcc tct ggt ttt aac atc aag         98
Gly Ala Ser Val Lys Leu Ser Cys Lys Ala Ser Gly Phe Asn Ile Lys
 15                  20                  25                  30 gat tcg tat atg cat tgg ttg aga caa ggg cca gga caa aga ttg gaa        146
Asp Ser Tyr Met His Trp Leu Arg Gln Gly Pro Gly Gln Arg Leu Glu
                     35                  40                  45 tgg att ggc tgg att gat cca gag aat ggt gat act gag tac gct cct        194
Trp Ile Gly Trp Ile Asp Pro Glu Asn Gly Asp Thr Glu Tyr Ala Pro
                 50                  55                  60 aaa ttt cag gga aag gct act ttt act acc gac act tcc gct aat acc        242
Lys Phe Gln Gly Lys Ala Thr Phe Thr Thr Asp Thr Ser Ala Asn Thr
             65                  70                  75 gca tac ttg ggc tta tct tcc ttg aga cca gag gac act gcc gta tac        290
Ala Tyr Leu Gly Leu Ser Ser Leu Arg Pro Glu Asp Thr Ala Val Tyr
         80                  85                  90 tac tgc aac gaa ggg aca cca act ggt cct tac tat ttc gac tac tgg        338
Tyr Cys Asn Glu Gly Thr Pro Thr Gly Pro Tyr Tyr Phe Asp Tyr Trp
 95                 100                 105                 110 gga caa ggt acc tta gtt act gtc tct agc ggt ggc gga ggt tca ggc        386
Gly Gln Gly Thr Leu Val Thr Val Ser Ser Gly Gly Gly Gly Ser Gly
                    115                 120                 125 ggt gga ggg tct gga ggt ggc ggt agt gaa aat gtg ctg acc caa tct        434
Gly Gly Gly Ser Gly Gly Gly Gly Ser Glu Asn Val Leu Thr Gln Ser
                130                 135                 140 cca agc tcc atg tct gcc tct gtt ggc gat aga gta acc atc gct tgt        482
Pro Ser Ser Met Ser Ala Ser Val Gly Asp Arg Val Thr Ile Ala Cys
            145                 150                 155 agc gca tcc tct agt gtc cca tat atg cac tgg ttt caa cag aag cca        530
Ser Ala Ser Ser Ser Val Pro Tyr Met His Trp Phe Gln Gln Lys Pro
        160                 165                 170 ggt aaa agc cca aag ttg ttg att tat tcg aca tcc aac ttg gct tct        578
Gly Lys Ser Pro Lys Leu Leu Ile Tyr Ser Thr Ser Asn Leu Ala Ser
175                 180                 185                 190 gga gtg cct tca agg ttt tct ggt tcc ggc tca gga acc gat tat agt        626
Gly Val Pro Ser Arg Phe Ser Gly Ser Gly Ser Gly Thr Asp Tyr Ser
                    195                 200                 205 ttg act att agc tca gtg cag cca gag gat gct gca acc tac tat tgc        674
Leu Thr Ile Ser Ser Val Gln Pro Glu Asp Ala Ala Thr Tyr Tyr Cys
                210                 215                 220 cag caa agg tcc tca tat cca ctg act ttc ggg ggt gga acg aag ttg        722
Gln Gln Arg Ser Ser Tyr Pro Leu Thr Phe Gly Gly Gly Thr Lys Leu
            225                 230                 235 gaa atc aag gct gcg gcc gcc tgt cat cat cat cat cat cat              764
Glu Ile Lys Ala Ala Ala Ala Cys His His His His His His
        240                 245                 250

<210> SEQ ID NO 13
<211> LENGTH: 252
<212> TYPE: PRT
<213> ORGANISM: Artificial sequence
<220> FEATURE:
<223> OTHER INFORMATION: Synthetic Construct

<400> SEQUENCE: 13

Gln Val Lys Leu Glu Gln Ser Gly Ala Glu Val Val Lys Pro Gly Ala
 1               5                  10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45
```

```
Gly Trp Ile Asp Pro Glu Asn Gly Asp Thr Glu Tyr Ala Pro Lys Phe
 50                  55                  60

Gln Gly Lys Ala Thr Phe Thr Thr Asp Thr Ser Ala Asn Thr Ala Tyr
 65                  70                  75                  80

Leu Gly Leu Ser Ser Leu Arg Pro Glu Asp Thr Ala Val Tyr Tyr Cys
                 85                  90                  95

Asn Glu Gly Thr Pro Thr Gly Pro Tyr Tyr Phe Asp Tyr Trp Gly Gln
            100                 105                 110

Gly Thr Leu Val Thr Val Ser Gly Gly Gly Gly Ser Gly Gly Gly Gly
        115                 120                 125

Gly Ser Gly Gly Gly Gly Ser Glu Asn Val Leu Thr Gln Ser Pro Ser
130                 135                 140

Ser Met Ser Ala Ser Val Gly Asp Arg Val Thr Ile Ala Cys Ser Ala
145                 150                 155                 160

Ser Ser Ser Val Pro Tyr Met His Trp Phe Gln Gln Lys Pro Gly Lys
                165                 170                 175

Ser Pro Lys Leu Leu Ile Tyr Ser Thr Ser Asn Leu Ala Ser Gly Val
            180                 185                 190

Pro Ser Arg Phe Ser Gly Ser Gly Ser Gly Thr Asp Tyr Ser Leu Thr
        195                 200                 205

Ile Ser Ser Val Gln Pro Glu Asp Ala Ala Thr Tyr Tyr Cys Gln Gln
    210                 215                 220

Arg Ser Ser Tyr Pro Leu Thr Phe Gly Gly Gly Thr Lys Leu Glu Ile
225                 230                 235                 240

Lys Ala Ala Ala Ala Cys His His His His His His
                245                 250

<210> SEQ ID NO 14
<211> LENGTH: 815
<212> TYPE: DNA
<213> ORGANISM: Artificial sequence
<220> FEATURE:
<223> OTHER INFORMATION: Synthetic sequence: HFEVP1 Cys Cloned into
      modified pPICZalphaB
      Expressed in P. pastoris
<220> FEATURE:
<221> NAME/KEY: CDS
<222> LOCATION: (9)..(815)

<400> SEQUENCE: 14 ccatggcc caa gtt aaa ctg gaa cag tcc ggt gct gaa gtt gtc aaa cca      50
         Gln Val Lys Leu Glu Gln Ser Gly Ala Glu Val Val Lys Pro
          1               5                  10 ggt gct tcc gtg aag tt

| | | | | | | | | | | | | | | | | |
|---|---|---|---|---|---|---|---|---|---|---|---|---|---|---|---|---|
| tac | tgc | aac | gaa | ggg | aca | cca | act | gca | gtt | ccg | aac | ctg | cga | ggt | gat | 338 |
| Tyr | Cys | Asn | Glu | Gly | Thr | Pro | Thr | Ala | Val | Pro | Asn | Leu | Arg | Gly | Asp | |
| 95 | | | | 100 | | | | | 105 | | | | | 110 | | |
| ctg | cag | gtg | ctg | gct | cag | aaa | gtt | gca | ggt | cct | tac | cct | ttc | gac | tac | 386 |
| Leu | Gln | Val | Leu | Ala | Gln | Lys | Val | Ala | Gly | Pro | Tyr | Pro | Phe | Asp | Tyr | |
| | | | 115 | | | | | 120 | | | | | 125 | | | |
| tgg | gga | caa | ggt | acc | tta | gtt | act | gtc | tct | agc | ggt | ggc | gga | ggt | tca | 434 |
| Trp | Gly | Gln | Gly | Thr | Leu | Val | Thr | Val | Ser | Ser | Gly | Gly | Gly | Gly | Ser | |
| | | | 130 | | | | | 135 | | | | | 140 | | | |
| ggc | ggt | gga | ggg | tct | gga | ggt | ggc | ggt | agt | gaa | aat | gtg | ctg | acc | caa | 482 |
| Gly | Gly | Gly | Gly | Ser | Gly | Gly | Gly | Gly | Ser | Glu | Asn | Val | Leu | Thr | Gln | |
| | | 145 | | | | | 150 | | | | | 155 | | | | |
| tct | cca | agc | tcc | atg | tct | gct | tct | gtt | ggc | gat | aga | gta | acc | atc | gct | 530 |
| Ser | Pro | Ser | Ser | Met | Ser | Ala | Ser | Val | Gly | Asp | Arg | Val | Thr | Ile | Ala | |
| | | 160 | | | | | 165 | | | | | 170 | | | | |
| tgt | agc | gca | tcc | tct | agt | gtc | cca | tat | atg | cac | tgg | ttt | caa | cag | aag | 578 |
| Cys | Ser | Ala | Ser | Ser | Ser | Val | Pro | Tyr | Met | His | Trp | Phe | Gln | Gln | Lys | |
| 175 | | | | 180 | | | | | 185 | | | | | 190 | | |
| cca | ggt | aaa | agc | cca | aag | ttg | ttg | att | tat | tcg | aca | tcc | aac | ttg | gct | 626 |
| Pro | Gly | Lys | Ser | Pro | Lys | Leu | Leu | Ile | Tyr | Ser | Thr | Ser | Asn | Leu | Ala | |
| | | | 195 | | | | | 200 | | | | | 205 | | | |
| tct | gga | gtg | cct | tca | agg | ttt | tct | ggt | tcc | ggc | tca | gga | acc | gat | tat | 674 |
| Ser | Gly | Val | Pro | Ser | Arg | Phe | Ser | Gly | Ser | Gly | Ser | Gly | Thr | Asp | Tyr | |
| | | 210 | | | | | 215 | | | | | 220 | | | | |
| agt | ttg | act | att | agc | tca | gtg | cag | cca | gag | gat | gct | gca | acc | tac | tat | 722 |
| Ser | Leu | Thr | Ile | Ser | Ser | Val | Gln | Pro | Glu | Asp | Ala | Ala | Thr | Tyr | Tyr | |
| | | 225 | | | | | 230 | | | | | 235 | | | | |
| tgc | cag | caa | agg | tcc | tca | tat | cca | ctg | act | ttc | ggg | ggt | gga | acg | aag | 770 |
| Cys | Gln | Gln | Arg | Ser | Ser | Tyr | Pro | Leu | Thr | Phe | Gly | Gly | Gly | Thr | Lys | |
| | 240 | | | | | 245 | | | | | 250 | | | | | |
| ttg | gaa | atc | aag | gct | gcg | gcc | gcc | tgt | cat | cat | cat | cat | cat | cat | | 815 |
| Leu | Glu | Ile | Lys | Ala | Ala | Ala | Ala | Cys | His | His | His | His | His | His | | |
| 255 | | | | 260 | | | | | 265 | | | | | | | |

<210> SEQ ID NO 15
<211> LENGTH: 269
<212> TYPE: PRT
<213> ORGANISM: Artificial sequence
<220> FEATURE:
<223> OTHER INFORMATION: Synthetic Construct

<400> SEQUENCE: 15

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Ala Val Pro Asn Leu Arg Gly Asp Leu Gln
            100                 105                 110

Val Leu Ala Gln Lys Val Ala Gly Pro Tyr Pro Phe Asp Tyr Trp Gly
        115                 120                 125

```
Gln Gly Thr Leu Val Thr Val Ser Ser Gly Gly Gly Ser Gly
        130                 135                 140
Gly Gly Ser Gly Gly Gly Ser Glu Asn Val Leu Thr Gln Ser Pro
145                 150                 155                 160
Ser Ser Met Ser Ala Ser Val Gly Asp Arg Val Thr Ile Ala Cys Ser
                165                 170                 175
Ala Ser Ser Ser Val Pro Tyr Met His Trp Phe Gln Gln Lys Pro Gly
            180                 185                 190
Lys Ser Pro Lys Leu Leu Ile Tyr Ser Thr Ser Asn Leu Ala Ser Gly
        195                 200                 205
Val Pro Ser Arg Phe Ser Gly Ser Gly Ser Gly Thr Asp Tyr Ser Leu
    210                 215                 220
Thr Ile Ser Ser Val Gln Pro Glu Asp Ala Ala Thr Tyr Tyr Cys Gln
225                 230                 235                 240
Gln Arg Ser Ser Tyr Pro Leu Thr Phe Gly Gly Gly Thr Lys Leu Glu
                245                 250                 255
Ile Lys Ala Ala Ala Ala Cys His His His His His His
            260                 265
```

<210> SEQ ID NO 16
<211> LENGTH: 51
<212> TYPE: DNA
<213> ORGANISM: Artificial sequence
<220> FEATURE:
<223> OTHER INFORMATION: Synthetic sequence: HFEVP1 Cys Cloned into
      modified pPICZalphaB
      Expressed in P. pastoris

<400> SEQUENCE: 16
tgcaactttc tgagccagca cctgcagatc acctcgcaga ttcggaactg c            51

<210> SEQ ID NO 17
<211> LENGTH: 7
<212> TYPE: PRT
<213> ORGANISM: Artificial sequence
<220> FEATURE:
<223> OTHER INFORMATION: Synthetic sequence: Sequence motif
<220> FEATURE:
<221> NAME/KEY: VARIANT
<222> LOCATION: (5)..(6)
<223> OTHER INFORMATION: Xaa represents any amino acid

<400> SEQUENCE: 17

Arg Gly Asp Leu Xaa Xaa Leu
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic sequence: Sequence motif
<220> FEATURE:
<221> NAME/KEY: VARIANT
<222> LOCATION: (5)..(6)
<223> OTHER INFORMATION: Xaa represents any amino acid

<400> SEQUENCE: 18

Arg Gly Asp Leu Xaa Xaa Ile
1               5

```
<210> SEQ ID NO 19
<211> LENGTH: 17
<212> TYPE: PRT
<213> ORGANISM: Artificial sequence
<220> FEATURE:
<223> OTHER INFORMATION: Synthetic sequence: Targeting peptide

<400> SEQUENCE: 19

Ala Val Pro Asn Leu Arg Gly Asp Leu Gln Val Leu Ala Gln Lys Val
1               5                   10                  15
Ala

<210> SEQ ID NO 20
<211> LENGTH: 7
<212> TYPE: PRT
<213> ORGANISM: Artificial sequence
<220> FEATURE:
<223> OTHER INFORMATION: Synthetic sequence: Heavy chain CDR1

<400> SEQUENCE: 20

Gly Phe Asn Ile Lys Asp Ser
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic sequence: Heavy chain CDR2

<400> SEQUENCE: 21

Asp Pro Glu Asn Gly Asp
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic sequence: Heavy chain CDR3

<400> SEQUENCE: 22

Thr Pro Thr Gly Pro Tyr Tyr Phe Asp
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic sequence: Light chain CDR1

<400> SEQUENCE: 23

Ser Ser Ser Val Pro
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic sequence: Light chain CDR1

<400> SEQUENCE: 24

Ser Ser Ser Val Ser
1               5
```

```
<210> SEQ ID NO 25
<211> LENGTH: 6
<212> TYPE: PRT
<213> ORGANISM: Artificial sequence
<220> FEATURE:
<223> OTHER INFORMATION: Synthetic sequence: Light chain CDR3

<400> SEQUENCE: 25

Arg Ser Ser Tyr Pro Leu
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 26

Gly Gly Gly Gly Ser
1               5

<210> SEQ ID NO 27
<211> LENGTH: 10
<212> TYPE: PRT
<213> ORGANISM: Artificial sequence
<220> FEATURE:
<223> OTHER INFORMATION: Synthetic sequence: Linker

<400> SEQUENCE: 27

Gly Gly Gly Gly Ser Gly Gly Gly Gly Ser
1               5                   10

<210> SEQ ID NO 28
<211> LENGTH: 15
<212> TYPE: PRT
<213> ORGANISM: Artificial sequence
<220> FEATURE:
<223> OTHER INFORMATION: Synthetic sequence: Linker

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 20
<212> TYPE: PRT
<213> ORGANISM: Artificial sequence
<220> FEATURE:
<223> OTHER INFORMATION: Synthetic sequence: Linker

<400> SEQUENCE: 29

Gly Gly Gly Gly Ser Gly Gly Gly Gly Ser Gly Gly Gly Gly Ser Gly
1               5                   10                  15

Gly Gly Gly Ser
            20

<210> SEQ ID NO 30
<211> LENGTH: 62
<212> TYPE: DNA
<213> ORGANISM: Artificial sequence
<220> FEATURE:
<223> OTHER INFORMATION: Synthetic sequence: Primer
```

```
<400> SEQUENCE: 30
ctactgcaac gaagggacag ctagaggtga tttggctact tgttcgact actggggaca    60 ag                                                                   62

<210> SEQ ID NO 31
<211> LENGTH: 62
<212> TYPE: DNA
<213> ORGANISM: Artificial sequence
<220> FEATURE:
<223> OTHER INFORMATION: Synthetic sequence: Primer

<400> SEQUENCE: 31
cttgtcccca gtagtcgaac aaagtagcca atcacctct agctgtccct tcgttgcagt    60
ag                                                                   62

<210> SEQ ID NO 32
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 32
gaagggacag ctagaggtga attggctact tgttcgact actg                    44

<210> SEQ ID NO 33
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 33
cagtagtcga acaaagtagc caattcacct ctagctgtcc cttc                    44

<210> SEQ ID NO 34
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 34
catgccatgg cccaggtgaa actg                                          24

<210> SEQ ID NO 35
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 35
catgccatgg cccaagttaa actggaacag tcc                                33

<210> SEQ ID NO 36
<211> LENGTH: 60
<212> TYPE: DNA
<213> ORGANISM: Artificial sequence
<220> FEATURE:
<223> OTHER INFORMATION: Synthetic sequence: Primer

<400> SEQUENCE: 36
gcgccagcac ctgcagatca cctcgcagat tcggaactgc agtcggagtc ccctcattac   60
```

```
<210> SEQ ID NO 37
<211> LENGTH: 60
<212> TYPE: DNA
<213> ORGANISM: Artificial sequence
<220> FEATURE:
<223> OTHER INFORMATION: Synthetic sequence: Primer

<400> SEQUENCE: 37
gagccagcac ctgcagatca cctcgcagat tcggaactgc agttggtgtc ccttcgttgc      60

<210> SEQ ID NO 38
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 38
atagtttagc ggccgcccgt ttcagctc                                        28

<210> SEQ ID NO 39
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 39
atagtttagc ggccgcagcc ttgatttc                                        28

<210> SEQ ID NO 40
<211> LENGTH: 62
<212> TYPE: DNA
<213> ORGANISM: Artificial sequence
<220> FEATURE:
<223> OTHER INFORMATION: Synthetic sequence: Primer

<400> SEQUENCE: 40
ctgcgaggtg atctgcaggt gctggcgcag aaagttgcag gccgtacta ctttgactac      60 tg                                                                    62

<210> SEQ ID NO 41
<211> LENGTH: 71
<212> TYPE: DNA
<213> ORGANISM: Artificial sequence
<220> FEATURE:
<223> OTHER INFORMATION: Synthetic sequence: Primer

<400> SEQUENCE: 41
ctgcgaggtg atctgcaggt gctggctcag aaagttgcag gtccttaccc tttcgactac     60
tggggacaag g                                                          71

<210> SEQ ID NO 42
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 42
gttgcagggc cgtacccgtt tgactactgg ggc                                  33
```

```
<210> SEQ ID NO 43
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 43
gccccagtag tcaaacgggt acggccctgc aac                                    33

<210> SEQ ID NO 44
<211> LENGTH: 7
<212> TYPE: PRT
<213> ORGANISM: Artificial sequence
<220> FEATURE:
<223> OTHER INFORMATION: Synthetic sequence

<400> SEQUENCE: 44

Arg Gly Asp Leu Ala Thr Leu
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic sequence: Motif
<220> FEATURE:
<221> NAME/KEY: VARIANT
<222> LOCATION: (2)..(2)
<223> OTHER INFORMATION: Xaa represents any amino acid
<220> FEATURE:
<221> NAME/KEY: VARIANT
<222> LOCATION: (5)..(6)
<223> OTHER INFORMATION: Xaa represents any amino acid

<400> SEQUENCE: 45

Arg Xaa Asp Leu Xaa Xaa Leu
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic sequence

<400> SEQUENCE: 46

Ala Arg Gly Glu Leu Ala Thr Leu
1               5

<210> SEQ ID NO 47
<211> LENGTH: 5
<212> TYPE: PRT
<213> ORGANISM: Artificial sequence
<220> FEATURE:
<223> OTHER INFORMATION: Synthetic sequence: Sequence motif
<220> FEATURE:
<221> NAME/KEY: VARIANT
<222> LOCATION: (3)..(4)
<223> OTHER INFORMATION: Xaa represents any amino acid

<400> SEQUENCE: 47

Asp Leu Xaa Xaa Leu
1               5
```

```
<210> SEQ ID NO 48
<211> LENGTH: 4
<212> TYPE: PRT
<213> ORGANISM: Artificial sequence
<220> FEATURE:
<223> OTHER INFORMATION: Synthetic sequence: Sequence motif
<220> FEATURE:
<221> NAME/KEY: VARIANT
<222> LOCATION: (2)..(3)
<223> OTHER INFORMATION: Xaa represents any amino acid

<400> SEQUENCE: 48

Leu Xaa Xaa Leu
1

<210> SEQ ID NO 49
<211> LENGTH: 4
<212> TYPE: PRT
<213> ORGANISM: Artificial sequence
<220> FEATURE:
<223> OTHER INFORMATION: Synthetic sequence: Sequence motif
<220> FEATURE:
<221> NAME/KEY: VARIANT
<222> LOCATION: (2)..(3)
<223> OTHER INFORMATION: Xaa represents any amino acid

<400> SEQUENCE: 49

Leu Xaa Xaa Ile
1

<210> SEQ ID NO 50
<211> LENGTH: 7
<212> TYPE: PRT
<213> ORGANISM: Artificial sequence
<220> FEATURE:
<223> OTHER INFORMATION: Synthetic sequence: Motif
<220> FEATURE:
<221> NAME/KEY: VARIANT
<222> LOCATION: (5)..(7)
<223> OTHER INFORMATION: Xaa represents any amino acid

<400> SEQUENCE: 50

Arg Gly Asp Leu Xaa Xaa Xaa
1               5

<210> SEQ ID NO 51
<211> LENGTH: 7
<212> TYPE: PRT
<213> ORGANISM: Artificial sequence
<220> FEATURE:
<223> OTHER INFORMATION: Synthetic sequence: Motif
<220> FEATURE:
<221> NAME/KEY: VARIANT
<222> LOCATION: (5)..(7)
<223> OTHER INFORMATION: Xaa is Glu, Ala, Leu, Met, Gln, Lys, Arg, Val,
      Ile, Trp, Phe, Asp, His or Thr

<400> SEQUENCE: 51

Arg Gly Asp Leu Xaa Xaa Xaa
1               5

<210> SEQ ID NO 52
<211> LENGTH: 7
<212> TYPE: PRT
<213> ORGANISM: Artificial sequence
<220> FEATURE:
<223> OTHER INFORMATION: Synthetic sequence: Motif
<220> FEATURE:
<221> NAME/KEY: VARIANT
<222> LOCATION: (5)..(5)
<223> OTHER INFORMATION: Xaa is Glu, Ala, or Gln
```

```
<220> FEATURE:
<221> NAME/KEY: VARIANT
<222> LOCATION: (6)..(6)
<223> OTHER INFORMATION: Xaa is His, Val, Thr, or Glu
<220> FEATURE:
<221> NAME/KEY: VARIANT
<222> LOCATION: (7)..(7)
<223> OTHER INFORMATION: Xaa is Leu or Ile

<400> SEQUENCE: 52

Arg Gly Asp Leu Xaa Xaa Xaa
1               5

<210> SEQ ID NO 53
<211> LENGTH: 5
<212> TYPE: PRT
<213> ORGANISM: Artificial Sequence
<220> FEATURE:
<223> OTHER INFORMATION: Heavy Chain CDR1 sequence

<400> SEQUENCE: 53

Asp Ser Tyr Met His
1               5

<210> SEQ ID NO 54
<211> LENGTH: 17
<212> TYPE: PRT
<213> ORGANISM: Artificial Sequence
<220> FEATURE:
<223> OTHER INFORMATION: Heavy Chain CDR2 sequence

<400> SEQUENCE: 54

Trp Ile Asp Pro Glu Asn Gly Asp Thr Glu Tyr Ala Pro Lys Phe Gln
1               5                   10                  15

Gly

<210> SEQ ID NO 55
<211> LENGTH: 11
<212> TYPE: PRT
<213> ORGANISM: Artificial Sequence
<220> FEATURE:
<223> OTHER INFORMATION: Heavy Chain CDR3 sequence

<400> SEQUENCE: 55

Gly Thr Pro Thr Gly Pro Tyr Tyr Phe Asp Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Heavy Chain CDR3 sequence

<400> SEQUENCE: 56

Gly Thr Pro Thr Gly Pro Tyr Pro Phe Asp Tyr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Light Chain CDR1 sequence
```

```
<400> SEQUENCE: 57

Ser Ala Ser Ser Ser Val Pro Tyr Met His
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Light Chain CDR1 sequence

<400> SEQUENCE: 58

Ser Ala Ser Ser Ser Val Ser Tyr Met His
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Light Chain CDR2 sequence

<400> SEQUENCE: 59

Ser Thr Ser Asn Leu Ala Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Light Chain CDR2 sequence

<400> SEQUENCE: 60

Leu Thr Ser Asn Leu Ala Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Light Chain CDR3 sequence

<400> SEQUENCE: 61

Gln Gln Arg Ser Ser Tyr Pro Leu Thr
1               5
```